United States Patent
Rice et al.

(10) Patent No.: US 11,634,734 B2
(45) Date of Patent: *Apr. 25, 2023

(54) LIMITING YEAST-PRODUCED TREHALOSE IN FERMENTATION

(71) Applicant: Lallemand Hungary Liquidity Management LLC, Budapest (HU)

(72) Inventors: Charles F. Rice, Plainfield, NH (US); Ryan Skinner, Bethel, VT (US); Trisha Barrett, Bradford, VT (US); Aaron Argyros, Lebanon, NH (US)

(73) Assignee: Lallemand Hungary Liquidity Management LLC, Budapest (HU)

(*) Notice: Subject to any disclaimer, the term of this patent is extended or adjusted under 35 U.S.C. 154(b) by 0 days.

This patent is subject to a terminal disclaimer.

(21) Appl. No.: 17/170,529

(22) Filed: Feb. 8, 2021

(65) Prior Publication Data

US 2021/0163999 A1 Jun. 3, 2021

Related U.S. Application Data

(63) Continuation of application No. 16/776,389, filed on Jan. 29, 2020, now Pat. No. 10,947,568, which is a continuation of application No. 15/773,139, filed as application No. PCT/IB2016/056658 on Nov. 4, 2016, now Pat. No. 10,570,421.

(60) Provisional application No. 62/251,885, filed on Nov. 6, 2015.

(51) Int. Cl.
| | |
|---|---|
| *C12P 7/20* | (2006.01) |
| *C12P 7/10* | (2006.01) |
| *C12N 9/24* | (2006.01) |
| *C12N 1/18* | (2006.01) |
| *C12N 15/81* | (2006.01) |
| *C12P 19/12* | (2006.01) |

(52) U.S. Cl.
CPC ............ *C12P 7/10* (2013.01); *C12N 1/18* (2013.01); *C12N 9/2402* (2013.01); *C12N 15/81* (2013.01); *C12P 7/20* (2013.01); *C12Y 302/01028* (2013.01); *C12P 19/12* (2013.01); *Y02E 50/10* (2013.01)

(58) Field of Classification Search
CPC ........ C12N 15/81; C12N 9/2405; C12N 1/18; C12P 7/20
See application file for complete search history.

(56) References Cited

U.S. PATENT DOCUMENTS

| | | | |
|---|---|---|---|
| 10,570,421 B2* | 2/2020 | Rice | C12N 9/2402 |
| 10,947,568 B2* | 3/2021 | Rice | C12Y 302/01028 |
| 11,198,881 B2* | 12/2021 | Argyros | C12Y 302/01003 |
| 2018/0320203 A1 | 11/2018 | Rice et al. | |

FOREIGN PATENT DOCUMENTS

| | | |
|---|---|---|
| WO | 2011/153516 A2 | 12/2011 |
| WO | 2015/065871 A1 | 5/2015 |
| WO | 2015/065978 A1 | 5/2015 |
| WO | 2015/148272 A1 | 10/2015 |

OTHER PUBLICATIONS

Amaral et al., "Molecular cloning of the neutral trehalase gene from *Kluyveromyces lactis* and the distinction between neutral and acid trehalases," Arch Microbiol. Apr. 1997;167(4):202-8.

An et al., "Enhanced thermotolerance for ethanol fermentation of *Saccharomyces cerevisiae* strain by overexpression of the gene coding for trehalose-6-phosphate synthase," Biotechnol Lett. 33.7 (2011): 1367-1374.

Bell et al., "Composition and Functional Analysis of the *Saccharomyces cerevisiae* Trehalose Synthase Complex," Journal of Bio Chem. 11 (1998): 33311-33319.

Cao et al., "Expression of TPS1 gene from *Saccharomycopsis fibuligera* A11 in *Saccharomyces* sp. W0 enhances trehalose accumulation, ethanol tolerance, and ethanol production," Mol Biotechnol 56.1 (2014): 72-78.

De Virgilio et al., "Disruption of TPS2, the gene encoding the 100-kDa subunit of the trehalose-6-phosphate synthase/phosphatase complex in *Saccharomyces cerevisiae*, causes accumulation of trehalose-6-phosphate and loss of trehalose-6-phosphate phosphatase activity," Eur J Biochem. Mar. 1, 1993;212(2):315-23.

Elbein et al., "New insights on trehalose: a multifunctional molecule," Glycobiology. 13.4 (2003): 17R-27R.

Elliott et al., Synergy between trehalose and Hsp104 for thermotolerance in *Saccharomyces cerevisiae*. Genetics. Nov. 1996;144(3):923-33.

Frison et al., "The *Arabidopsis thaliana* trehalase is a plasma membrane-bound enzyme with extracellular activity," FEBS Lett. Aug. 21, 2007;581(21):4010-6.

Ge et al., "Improve carbon metabolic flux in *Saccharomyces cerevisiae* at high temperature by overexpressed TSL1 gene," J Ind Microbiol Biotechnol. 40 (2013): 345-352.

(Continued)

*Primary Examiner* — Tekchand Saidha
(74) *Attorney, Agent, or Firm* — Seed IP Law Group LLP

(57) ABSTRACT

The present disclosure relates to recombinant yeast host cells having (i) a first genetic modification for reducing the production of one or more native enzymes that function to produce glycerol or regulating glycerol synthesis and/or allowing the production of an heterologous glucoamylase and (ii) a second genetic modification for reducing the production of one or more native enzymes that function to produce trehalose or regulating trehalose synthesis and/or allowing the expression of an heterologous trehalase. The recombinant yeast host cells can be used to limit the production of (yeast-produced) trehalose (particularly extracellular trehalose) during fermentation and, in some embodiments, can increase the production of a fermentation product (such as, for example, ethanol).

17 Claims, 7 Drawing Sheets

Specification includes a Sequence Listing.

(56) References Cited

OTHER PUBLICATIONS

Giffen, New Insights into fermentation drop samples: The real story of total residual sugars. Fuel Ethanol Workshop and Expo. Minneapolis, MN. Jun. 5, 2012, 13 pages.

Guo et al., "Minimization of glycerol synthesis in industrial ethanol yeast without influencing its fermentation performance," Metabol Eng 13.1 (2011): 49-59.

Liu et al., "Expression, purification, and characterization of recombinant *Metarhizium anisopliae* acid trehalase in *Pichia pastoris*," Protein Expr Purif. Jul. 2007;54(1):66-72.

Singer et al., "Thermotolerance in *Saccharomyces cerevisiae*: the Yin and Yang of trehalose," Trends Biotechnol. 16.11 (1998): 460-468.

Thevelein et al., "Trehalose synthase: guard to the gate of glycolysis in yeast?" Trends Biochem Sci 20.1 (1995): 3-10.

Van Dijck et al., "Disruption of the *Candida albicans* TPS2 gene encoding trehalose-6-phosphate phosphatase decreases infectivity without affecting hypha formation," Infect Immun. Apr. 2002;70(4):1772-82.

Zilli et al., "Secretion of the acid trehalase encoded by the CgATH1 gene allows trehalose fermentation by *Candida glabrata*," Microbiol Res. Oct. 2015;179:12-9.

\* cited by examiner

SEQUENCE LISTING

<160> NUMBER OF SEQ ID NOS: 60

<210> SEQ ID NO 1
<211> LENGTH: 1072
<212> TYPE: PRT
<213> ORGANISM: Aspergillus fumigatus

<400> SEQUENCE: 1

| | | | | | | | | | | | | | | | |
|---|---|---|---|---|---|---|---|---|---|---|---|---|---|---|---|
| Met | Leu | Ser | Gln | Asn | Leu | Ala | Thr | Trp | Val | Ser | Leu | Leu | Ala | Cys | Leu |
| 1 | | | | 5 | | | | | 10 | | | | | 15 | |
| Pro | Ala | Ala | Ile | Gly | Leu | Pro | Asn | Asn | Asn | Asp | Arg | Val | Ala | Arg | Ser |
| | | | 20 | | | | | 25 | | | | | 30 | | |
| Leu | Lys | Arg | His | Gly | Gly | His | Gly | His | Lys | Gln | Val | Asp | Thr | Asn | Ser |
| | | | 35 | | | | 40 | | | | | 45 | | | |
| Ser | His | Val | Tyr | Lys | Thr | Arg | Phe | Pro | Gly | Val | Thr | Trp | Asp | Asp | Asp |
| | 50 | | | | | 55 | | | | | 60 | | | | |
| His | Trp | Leu | Leu | Ser | Thr | Thr | Thr | Leu | Asp | Gln | Gly | His | Tyr | Gln | Ser |
| 65 | | | | | 70 | | | | | 75 | | | | | 80 |
| Arg | Gly | Ser | Ile | Ala | Asn | Gly | Tyr | Leu | Gly | Ile | Asn | Val | Ala | Ser | Val |
| | | | | 85 | | | | | 90 | | | | | 95 | |
| Gly | Pro | Phe | Phe | Glu | Leu | Asp | Val | Pro | Val | Ser | Gly | Asp | Val | Ile | Asn |
| | | | 100 | | | | | 105 | | | | | 110 | | |
| Gly | Trp | Pro | Leu | Tyr | Ser | Arg | Arg | Gln | Thr | Phe | Ala | Thr | Ile | Ala | Gly |
| | | | | 115 | | | | | 120 | | | | | 125 | |
| Phe | Phe | Asp | Tyr | Gln | Pro | Thr | Thr | Asn | Gly | Ser | Asn | Phe | Pro | Trp | Leu |
| | | | 130 | | | | | 135 | | | | | 140 | | |
| Asn | Gln | Tyr | Gly | Gly | Glu | Ser | Val | Ile | Ser | Gly | Ile | Pro | His | Trp | Ser |
| 145 | | | | | 150 | | | | | 155 | | | | | 160 |
| Gly | Leu | Ile | Leu | Asp | Leu | Gly | Asp | Gly | Asn | Tyr | Leu | Asp | Ala | Thr | Val |
| | | | | 165 | | | | | 170 | | | | | 175 | |
| Asp | Asn | Lys | Thr | Ile | Thr | Asp | Phe | Arg | Ser | Thr | Tyr | Asp | Phe | Lys | Ser |
| | | | 180 | | | | | 185 | | | | | 190 | | |
| Gly | Val | Leu | Ser | Trp | Ser | Tyr | Thr | Trp | Thr | Pro | Lys | Cys | Asn | Lys | Gly |
| | | | | 195 | | | | | 200 | | | | | 205 | |
| Ser | Phe | Asn | Ile | Thr | Tyr | Arg | Leu | Phe | Ala | His | Lys | Leu | His | Val | Asn |
| | | | 210 | | | | | 215 | | | | | 220 | | |
| Gln | Ala | Val | Val | Asp | Met | Glu | Ile | Thr | Pro | Ser | Gln | Gly | Ser | Glu | Ala |
| 225 | | | | | 230 | | | | | 235 | | | | | 240 |
| Thr | Val | Val | Asn | Val | Ile | Asp | Gly | Phe | Ser | Ala | Val | Arg | Thr | Asp | Phe |
| | | | | 245 | | | | | 250 | | | | | 255 | |
| Val | Glu | Ser | Gly | Gln | Asp | Asn | Gly | Ala | Leu | Phe | Ser | Ala | Val | Arg | Pro |
| | | | 260 | | | | | 265 | | | | | 270 | | |
| Trp | Gly | Ile | Ser | Asn | Val | Thr | Ala | Tyr | Val | Tyr | Thr | Asn | Leu | Thr | Ala |
| | | | | 275 | | | | | 280 | | | | | 285 | |
| Ser | Ala | Gly | Val | Asp | Leu | Thr | Ser | Arg | Ala | Leu | Val | Asn | Asp | Lys | Pro |
| | | | 290 | | | | | 295 | | | | | 300 | | |
| Tyr | Val | His | Ser | Asn | Glu | Ser | Ser | Ile | Ala | Gln | Ala | Val | Asp | Val | Lys |
| 305 | | | | | 310 | | | | | 315 | | | | | 320 |
| Phe | Arg | Ala | Asn | Glu | Thr | Val | Arg | Ile | Thr | Lys | Phe | Val | Gly | Ala | Ala |
| | | | | 325 | | | | | 330 | | | | | 335 | |
| Ser | Ser | Asp | Ala | Phe | Pro | Asn | Pro | Gln | Gln | Thr | Ala | Lys | Gln | Ala | Val |
| | | | 340 | | | | | 345 | | | | | 350 | | |
| Ser | Ala | Ala | Met | Gly | Ala | Gly | Tyr | Met | Gly | Ser | Leu | Gln | Ser | His | Val |
| | | | | 355 | | | | | 360 | | | | | 365 | |

-continued

```
Glu Glu Trp Ala Ser Ile Leu Leu Asp Gly Ser Val Asp Ser Phe Val
    370                 375                 380
Asp Pro Ala Thr Gly Lys Leu Pro Asp Asp His Ile Leu Asn Ser
385                 390                 395                 400
Gln Ile Ile Ala Val Ala Asn Thr Tyr Leu Leu Gln Asn Thr Val
                405                 410                 415
Gly Lys Asn Ala Ile Lys Ala Val Ser Gly Ala Pro Val Asn Val Asp
                420                 425                 430
Ser Ile Ser Val Gly Gly Leu Thr Ser Asp Ser Tyr Ala Gly Leu Val
            435                 440                 445
Phe Trp Asp Ala Asp Val Trp Met Gln Pro Gly Leu Val Ala Ser His
    450                 455                 460
Pro Glu Ala Ala Gln Arg Val Thr Asn Tyr Arg Thr Lys Leu Tyr Pro
465                 470                 475                 480
Gln Ala Leu Glu Asn Ile Asn Thr Ala Phe Thr Ser Ser Lys Asn Arg
                485                 490                 495
Thr Thr Phe Ser Pro Ser Ala Ala Ile Tyr Pro Trp Thr Ser Gly Arg
                500                 505                 510
Phe Gly Asn Cys Thr Gly Thr Gly Pro Cys Trp Asp Tyr Gln Tyr His
            515                 520                 525
Leu Asn Gly Asp Ile Gly Leu Ser Leu Met Tyr Gln Trp Ile Ala Ser
    530                 535                 540
Gly Asp Thr Lys Thr Phe Arg Glu Gln His Phe Pro Ile Tyr Asp Ser
545                 550                 555                 560
Val Ala Thr Met Tyr Ser Asn Ile Val Gln Arg Asn Gly Ser Ser Trp
                565                 570                 575
Thr Leu Thr Asn Met Thr Asp Pro Asp Glu Tyr Ala Asn His Ile Asp
                580                 585                 590
Ala Gly Gly Phe Thr Met Pro Leu Ile Ser Glu Thr Leu Ser Tyr Ala
            595                 600                 605
Asn Ser Phe Arg Lys Gln Phe Gly Leu Glu Gln Asn Glu Thr Trp Thr
    610                 615                 620
Glu Ile Ser Glu Asn Val Leu Leu Ile Arg Glu Asp Gly Val Thr Leu
625                 630                 635                 640
Glu Tyr Thr Thr Met Asn Gly Thr Ala Val Val Lys Gln Ala Asp Ile
                645                 650                 655
Val Leu Val Thr Tyr Pro Leu Val Tyr Asp Asn Asn Tyr Thr Ala Gln
                660                 665                 670
His Ala Leu Asn Asp Leu Asp Tyr Tyr Ala Asn Gln Gln Ser Pro Asp
            675                 680                 685
Gly Pro Ala Met Thr Trp Ala Ile Phe Ala Ile Thr Ala Asn Asp Val
    690                 695                 700
Ser Pro Ser Gly Cys Ser Ala Tyr Thr Tyr His Gln Asp Ser Tyr Asp
705                 710                 715                 720
Pro Tyr Met Arg Ala Pro Phe Tyr Gln Leu Ser Glu Gln Met Ile Asp
                725                 730                 735
Asp Ala Gly Ile Asn Gly Gly Thr His Pro Ala Tyr Pro Phe Leu Thr
                740                 745                 750
Gly His Gly Gly Ala Asn Gln Val Leu Met Gly Tyr Leu Gly Leu
            755                 760                 765
Arg Leu Leu Pro Asp Asp Ala Ile His Ile Asp Pro Asn Leu Pro Pro
    770                 775                 780
Gln Val Ser Asn Leu Lys Tyr Arg Thr Phe Tyr Trp Arg Gly Trp Pro
```

```
            785                 790                 795                 800
        Ile Ser Ser Ser Asn Arg Thr His Thr Thr Ile Ser Arg Ala Ala
                        805                 810                 815

Asn Leu Ala Pro Leu Asp Thr Ala Asp Ser Arg Phe Ala Asn Ala Ser
                    820                 825                 830

Ile Pro Val Leu Val Gly Asp Pro Ser Asn Ser Thr Ala Tyr Arg Leu
                    835                 840                 845

Pro Val Thr Ala Pro Leu Val Val Pro Asn Arg Gln Ile Gly Phe Asn
            850                 855                 860

Asn Thr Ile Pro Gly Asn Met Val Gln Cys Arg Pro Val Tyr Ser Pro
        865                 870                 875                 880

Asn Asp Tyr Ala Pro Gly Gln Phe Pro Ile Ala Ala Val Asp Gly Ala
                        885                 890                 895

Thr Ser Thr Lys Trp Arg Pro Ser Thr Ala Asn Met Ser Ser Leu Thr
                        900                 905                 910

Val Ala Leu Ala Asp Val Glu Ile Asn Ser Lys Val Ser Gly Phe His
                    915                 920                 925

Phe Asn Trp Trp Gln Ala Pro Pro Val Asn Ala Thr Val Ile Phe His
                    930                 935                 940

Asp Glu Met Leu Glu Asp Pro Val Ala Ala Met Ser Ser Ser His Gly
        945                 950                 955                 960

Asn Ser Arg Tyr Arg Val Val Thr Thr Leu Thr Asn Ile Glu Gln Ser
                        965                 970                 975

Gln Pro Tyr Asp Ala Gln Ser Thr Asp Asn Glu Val Val Leu Asn
                    980                 985                 990

Thr Gly Asn Thr Thr Asp Val Ser Leu Ser Gln Thr Val His Thr Ser
                    995                 1000                1005

Arg Tyr Ala Thr Leu Leu Ile Ser Gly Asn Gln Ala Gly Gly Glu
            1010                1015                1020

Glu Gly Ala Thr Val Ala Glu Trp Ala Ile Leu Gly Glu Ser Lys
            1025                1030                1035

Gly Ser Ser Ser Gly His Gly Asn Asn Lys Arg Arg Leu Asp Val
            1040                1045                1050

Arg Ala Ala Ala Ala Leu Ser Ala Leu Asn Asp Arg Arg Tyr Arg
            1055                1060                1065

Gln Phe Asn Ala
            1070

<210> SEQ ID NO 2
<211> LENGTH: 1054
<212> TYPE: PRT
<213> ORGANISM: Aspergillus nidulans

<400> SEQUENCE: 2

Met Arg Phe Lys Ser Val Phe Thr Leu Leu Pro Leu Leu Ala Gln Leu
        1               5                   10                  15

Pro Ser Gly Gly Ala Ser Leu Pro Asn Asn His Gly Arg Val Glu Asn
                    20                  25                  30

Cys Val Arg Asn His Asp Gly Ile His Lys Phe Arg His Ser Asn Asn
                35                  40                  45

Thr Tyr Gln Ser Met Phe Pro Gly Val Thr Trp Asp Glu Asp Gln Trp
            50                  55                  60

Val Leu Thr Thr Ser Ser Leu Asp Gln Gly His Tyr Gln Ser Arg Gly
        65                  70                  75                  80
```

```
Ser Val Ala Asn Gly Tyr Ile Gly Ile Ser Val Ser Val Gly Pro
                 85                  90                  95

Phe Phe Glu Leu Asp Leu Pro Val Ala Gly Asp Val Ile Asn Gly Trp
            100                 105                 110

Pro Leu Tyr Ser Arg Arg Gln Ser Phe Ala Thr Ile Ser Gly Phe Phe
        115                 120                 125

Asp Ile Gln Ala Glu Thr Asn Gly Ser Asn Phe Pro Trp Met Asn Gln
130                 135                 140

Tyr Gly Gly Glu Ser Val Ile Ser Gly Val Pro His Trp Ser Gly Leu
145                 150                 155                 160

Ile Leu Asp Leu Gly Asp Asp Tyr Leu Asp Ser Thr Val Asp Asn
                165                 170                 175

Val Thr Leu Ser Asp Phe Lys Ser Ser Tyr Asp Phe Lys Ala Gly Val
            180                 185                 190

Leu Ser Trp Ser Tyr Thr Trp Thr Pro Ala Gly Asp Lys Gly Ser Tyr
        195                 200                 205

Ala Ile Thr Tyr Arg Leu Phe Ala Asn Lys Leu Asn Val Asn Gln Ala
    210                 215                 220

Val Val Asp Met Glu Ile Thr Pro Ser Gln Asp Gly His Ala Thr Ile
225                 230                 235                 240

Val Asn Val Leu Asp Gly Tyr Ser Ala Val Arg Thr Asp Phe Val Glu
                245                 250                 255

Ser Gln Glu Asp Asp Gly Ala Ile Tyr Ser Ala Val Arg Pro Trp Gly
            260                 265                 270

Ile Pro Asp Val Ser Ala Tyr Phe Tyr Ala Asn Ile Thr Gly Ser Lys
        275                 280                 285

His Val Asp Leu Ser Ser Arg Arg Leu Ile His Gly Lys Pro Tyr Val
    290                 295                 300

Ser Ala Asn Glu Ser Ser Ile Ala Gln Ala Ala Asp Val Asn Phe Val
305                 310                 315                 320

Ala Asn Glu Lys Val Arg Ile Thr Lys Phe Val Gly Ala Ala Ser Thr
                325                 330                 335

Asp Ala Phe Pro Asp Pro Gln Ala Thr Ala Lys Arg Ala Val Ser Glu
            340                 345                 350

Ala Leu Asp Ala Gly Tyr Gln Arg Ser Leu Arg Ser His Val Gln Glu
        355                 360                 365

Trp Ala Ser Ile Met His Glu Asp Ser Val Asp Arg Tyr Val Asn Pro
    370                 375                 380

Thr Thr Gly Lys Leu Pro Asp Asp Asn Ile Ile Asn Ser Ala Ile
385                 390                 395                 400

Ile Ala Val Ala Asn Thr Tyr Tyr Leu Leu Gln Asn Thr Val Gly Lys
                405                 410                 415

Asn Ala Ile Arg Ala Ala Gln Asp Ala Pro Leu Asn Val Asn Ser Phe
            420                 425                 430

Ser Val Gly Gly Leu Val Ser Asp Ser Tyr Ala Gly Leu Val Phe Trp
        435                 440                 445

Asp Ala Asp Val Trp Met Gln Pro Gly Leu Val Ala Ser His Pro Glu
    450                 455                 460

Ala Ala Gln Ala Val Thr Asn Tyr Arg Thr Lys Leu Tyr Pro Gln Ala
465                 470                 475                 480

Lys Lys Asn Ile Glu Thr Thr Tyr Thr Gly Ser Lys Asn Ala Thr Tyr
                485                 490                 495

Ile Asp Pro Ser Ala Ala Ile Tyr Pro Trp Thr Ser Gly Arg Phe Gly
```

```
                  500                 505                 510
Asn Cys Thr Gly Thr Gly Ala Cys Trp Asp Tyr Gln Tyr His Leu Asn
            515                 520                 525
Gly Asp Ile Gly Leu Ser Leu Ile Tyr Gln Trp Val Val Ser Gly Asp
            530                 535                 540
Thr Asn Thr Phe Arg Glu Lys His Phe Pro Ile Tyr Asp Ser Val Ala
545                 550                 555                 560
Ala Leu Tyr Gly Ser Ile Val Glu Arg Asn Gly Ser Tyr Trp Thr Leu
            565                 570                 575
Thr Asn Met Thr Asp Pro Asp Glu Tyr Ala Asn His Ile Asp Ala Gly
            580                 585                 590
Gly Phe Thr Met Pro Met Ile Ser Glu Thr Leu Glu Tyr Ala Asn Gln
            595                 600                 605
Phe Arg Gln Gln Phe Gly Leu Glu Pro Asn Glu Thr Trp Thr Glu Ile
            610                 615                 620
Ser Glu Asn Val Leu Val Leu Arg Glu Asn Gly Val Thr Leu Glu Tyr
625                 630                 635                 640
Thr Thr Met Asn Gly Thr Ala Ala Val Lys Gln Ala Asp Ile Val Leu
            645                 650                 655
Val Thr Tyr Pro Leu Val Tyr Asp Asn Tyr Thr Ala Glu Thr Ala Leu
            660                 665                 670
Thr Asp Leu Asp Tyr Tyr Ala Asn Arg Gln Ser Ala Asp Gly Pro Ala
            675                 680                 685
Met Thr Trp Ala Ile Phe Ser Ile Ala Ala Gly Ala Val Ser Pro Ser
            690                 695                 700
Gly Cys Ser Ala Tyr Thr Tyr His Gln Tyr Ser Tyr Ala Pro Tyr Ala
705                 710                 715                 720
Arg Ala Pro Phe Phe Gln Leu Ser Glu Gln Met Leu Asp Asn Ala Ser
            725                 730                 735
Ile Asn Gly Gly Thr His Pro Ala Tyr Pro Phe Leu Thr Gly His Gly
            740                 745                 750
Gly Ala Asn Gln Val Val Leu Phe Gly Tyr Leu Gly Leu Arg Leu Leu
            755                 760                 765
Pro Asp Asp Ala Ile His Ile Glu Pro Asn Leu Pro Pro Gln Ile Pro
            770                 775                 780
Tyr Val Lys Tyr Arg Thr Phe Tyr Trp Arg Gly Trp Pro Ile Ser Ala
785                 790                 795                 800
Gln Ser Asn Tyr Thr His Thr Val Leu Gln Arg Ser Gln Ser Ala Pro
            805                 810                 815
Leu Asp Thr Ala Asp Arg Arg Phe Ala Asn Thr Ser Ile Pro Val Phe
            820                 825                 830
Val Gly Leu Ala Asp Asn Ala Thr Leu His His Leu Pro Pro His Gly
            835                 840                 845
Pro Leu Thr Val Arg Asn Arg Glu Ile Gly Thr Ile Asn Thr Ile Glu
            850                 855                 860
Asp Asn Leu Ile Gln Cys Ser Pro Val Ser Ser Thr Asp Ala Phe Glu
865                 870                 875                 880
Gln Gly Gln Phe Pro Ile Ser Val Asp Gly Ala Thr Ser Thr Arg
            885                 890                 895
Trp Gln Pro Ser Ser Ser Asn Ala Ser Ala Val Thr Val Asn Leu Gly
            900                 905                 910
Ser Thr Thr Gly Arg Ser Val Gln Thr Val Ala Ser Gly Phe His Phe
            915                 920                 925
```

-continued

```
Asp Trp Ala Ala Ala Pro Pro Val Asn Ala Ser Val Ile Phe His Asp
            930                 935                 940

Thr Pro Leu Ser Asp Pro Val Ala Ala Leu Ser Ser Pro Gly Pro His
945                 950                 955                 960

Val Arg Ile Val Ala Asn Leu Thr Asn Ile Glu Gln Ser Gly Pro Tyr
                965                 970                 975

Asp Pro Glu Ala Thr Asp Leu Asn Glu Ile Lys Ile Pro Val Gly Asn
                980                 985                 990

Thr Thr Arg Ile Glu Leu Ala Gln Glu Val Pro Val Gly Arg Tyr Ala
            995                1000                1005

Thr Leu Val Ile Ser Gly Asn Gln Ala Leu Ala Gln Ala Asp Gly
   1010                1015                1020

Glu Asp His Val Gly Ala Thr Val Ala Glu Trp Ala Ile Leu Gly
   1025                1030                1035

Pro Lys Ser Gly Ser Pro Arg Arg Ile Gln Pro Val Pro Leu
   1040                1045                1050

Leu
```

<210> SEQ ID NO 3
<211> LENGTH: 515
<212> TYPE: PRT
<213> ORGANISM: Saccharomycopsis fibuligera

<400> SEQUENCE: 3

```
Met Ile Arg Leu Thr Val Phe Leu Thr Ala Val Phe Ala Ala Val Ala
1               5                  10                  15

Ser Cys Val Pro Val Glu Leu Asp Lys Arg Asn Thr Gly His Phe Gln
            20                  25                  30

Ala Tyr Ser Gly Tyr Thr Val Ala Arg Ser Asn Phe Thr Gln Trp Ile
        35                  40                  45

His Glu Gln Pro Ala Val Ser Trp Tyr Tyr Leu Leu Gln Asn Ile Asp
    50                  55                  60

Tyr Pro Glu Gly Gln Phe Lys Ser Ala Lys Pro Gly Val Val Val Ala
65                  70                  75                  80

Ser Pro Ser Thr Ser Glu Pro Asp Tyr Phe Tyr Gln Trp Thr Arg Asp
                85                  90                  95

Thr Ala Ile Thr Phe Leu Ser Leu Ile Ala Glu Val Glu Asp His Ser
            100                 105                 110

Phe Ser Asn Thr Thr Leu Ala Lys Val Val Glu Tyr Tyr Ile Ser Asn
        115                 120                 125

Thr Tyr Thr Leu Gln Arg Val Ser Asn Pro Ser Gly Asn Phe Asp Ser
    130                 135                 140

Pro Asn His Asp Gly Leu Gly Glu Pro Lys Phe Asn Val Asp Asp Thr
145                 150                 155                 160

Ala Tyr Thr Ala Ser Trp Gly Arg Pro Gln Asn Asp Gly Pro Ala Leu
                165                 170                 175

Arg Ala Tyr Ala Ile Ser Arg Tyr Leu Asn Ala Val Ala Lys His Asn
            180                 185                 190

Asn Gly Lys Leu Leu Leu Ala Gly Gln Asn Gly Ile Pro Tyr Ser Ser
        195                 200                 205

Ala Ser Asp Ile Tyr Trp Lys Ile Ile Lys Pro Asp Leu Gln His Val
    210                 215                 220

Ser Thr His Trp Ser Thr Ser Gly Phe Asp Leu Trp Glu Glu Asn Gln
225                 230                 235                 240
```

```
Gly Thr His Phe Phe Thr Ala Leu Val Gln Leu Lys Ala Leu Ser Tyr
            245                 250                 255

Gly Ile Pro Leu Ser Lys Thr Tyr Asn Asp Pro Gly Phe Thr Ser Trp
                260                 265                 270

Leu Glu Lys Gln Lys Asp Ala Leu Asn Ser Tyr Ile Asn Ser Ser Gly
            275                 280                 285

Phe Val Asn Ser Gly Lys Lys His Ile Val Glu Ser Pro Gln Leu Ser
        290                 295                 300

Ser Arg Gly Gly Leu Asp Ser Ala Thr Tyr Ile Ala Ala Leu Ile Thr
305                 310                 315                 320

His Asp Ile Gly Asp Asp Thr Tyr Thr Pro Phe Asn Val Asp Asn
            325                 330                 335

Ser Tyr Val Leu Asn Ser Leu Tyr Tyr Leu Val Asp Asn Lys Asn
            340                 345                 350

Arg Tyr Lys Ile Asn Gly Asn Tyr Lys Ala Gly Ala Val Gly Arg
            355                 360                 365

Tyr Pro Glu Asp Val Tyr Asn Gly Val Gly Thr Ser Glu Gly Asn Pro
    370                 375                 380

Trp Gln Leu Ala Thr Ala Tyr Ala Gly Gln Thr Phe Tyr Thr Leu Ala
385                 390                 395                 400

Tyr Asn Ser Leu Lys Asn Lys Asn Leu Val Ile Glu Lys Leu Asn
                405                 410                 415

Tyr Asp Leu Tyr Asn Ser Phe Ile Ala Asp Leu Ser Lys Ile Asp Ser
            420                 425                 430

Ser Tyr Ala Ser Lys Asp Ser Leu Thr Leu Thr Tyr Gly Ser Asp Asn
            435                 440                 445

Tyr Lys Asn Val Ile Lys Ser Leu Leu Gln Phe Gly Asp Ser Phe Leu
    450                 455                 460

Lys Val Leu Leu Asp His Ile Asp Asp Asn Gly Gln Leu Thr Glu Glu
465                 470                 475                 480

Ile Asn Arg Tyr Thr Gly Phe Gln Ala Gly Ala Val Ser Leu Thr Trp
                485                 490                 495

Ser Ser Gly Ser Leu Leu Ser Ala Asn Arg Ala Arg Asn Lys Leu Ile
            500                 505                 510

Glu Leu Leu
        515

<210> SEQ ID NO 4
<211> LENGTH: 757
<212> TYPE: PRT
<213> ORGANISM: Bacillus amyloliquefaciens

<400> SEQUENCE: 4

Met Ile Asn Gln Arg Leu Phe Glu Ile Asp Glu Trp Lys Ile Lys Thr
1               5                   10                  15

Asn Thr Phe Gln Lys Glu Tyr Ile Arg Leu Gln Glu Ser Leu Thr Ser
                20                  25                  30

Leu Ala Asn Gly Tyr Met Gly Ile Arg Gly Asn Phe Glu Glu Gly Tyr
            35                  40                  45

Ser Gly Gly Ser His Gln Gly Thr Tyr Ile Ala Gly Val Trp Phe Pro
        50                  55                  60

Asp Lys Thr Arg Val Gly Trp Trp Lys Asn Gly Tyr Pro Asp Tyr Phe
65                  70                  75                  80

Gly Lys Val Ile Asn Ala Met Asn Phe Ile Gly Ile Asp Val Tyr Val
```

```
            85                  90                  95
Asp Gly Glu Lys Val Asp Leu Tyr Gln Asn Arg Leu Glu Ser Phe Glu
            100                 105                 110

Leu Glu Leu His Met Lys Glu Gly Ile Leu Arg Arg Ser Ala Val Val
            115                 120                 125

Arg Ile Gln Asp Lys Thr Val Arg Ile Lys Ser Glu Arg Phe Leu Ser
            130                 135                 140

Leu Ala Ala Lys Glu Leu Cys Ala Ile His Tyr Glu Ala Glu Cys Leu
145                 150                 155                 160

Thr Gly Asp Ala Val Ile Thr Leu Val Pro Tyr Leu Asp Gly Asn Val
            165                 170                 175

Val Asn Glu Asp Ser Asn Tyr Gln Glu Arg Phe Trp Gln Glu Lys Glu
            180                 185                 190

Thr Gly Ala Asp Tyr Arg Arg Gly His Ile Thr Ala Lys Thr Leu Asp
            195                 200                 205

Asn Pro Phe Gly Thr Pro Arg Phe Thr Val Ser Ala Leu Met Glu Asn
            210                 215                 220

Leu Thr Glu Gly Tyr Val Ser Gln Ser Phe Gln Thr Ser Gly Met Tyr
225                 230                 235                 240

Ala Glu Asn Arg Phe Ser Tyr Gln Asn Lys Ala Ser Leu Lys Lys Phe
            245                 250                 255

Ile Val Val Thr Thr Ser Arg Asp Val Gln Glu Ala Glu Leu Thr Ser
            260                 265                 270

Lys Gly Glu Glu Leu Leu Ala Ala Ile Leu Lys Gln Gly Tyr Glu Glu
            275                 280                 285

Ala Arg Gln Gln His Ile Ala Lys Trp Lys Glu Arg Trp Ala Lys Ala
            290                 295                 300

Asp Ile Glu Ile Lys Gly Asp Glu Glu Leu Gln Gln Gly Ile Arg Tyr
305                 310                 315                 320

Asn Ile Phe Gln Leu Phe Ser Thr Tyr Tyr Gly Ala Asp Ala Arg Leu
            325                 330                 335

Asn Ile Gly Pro Lys Gly Phe Thr Gly Glu Lys Tyr Gly Gly Ala Ala
            340                 345                 350

Tyr Trp Asp Thr Glu Ala Tyr Ala Val Pro Met Tyr Leu Ala Thr Ala
            355                 360                 365

Glu Pro Glu Val Thr Lys Asn Leu Leu Leu Tyr Arg Tyr His His Leu
            370                 375                 380

Glu Ala Ala Lys Arg Asn Ala Ala Lys Leu Gly Met Lys Gly Ala Leu
385                 390                 395                 400

Tyr Pro Met Val Thr Phe Thr Gly Asp Glu Cys His Asn Glu Trp Glu
            405                 410                 415

Ile Thr Phe Glu Glu Ile His Arg Asn Gly Ala Ile Cys Tyr Ala Ile
            420                 425                 430

Cys Asn Tyr Val Gln Tyr Thr Gly Asp Arg Ala Tyr Met Glu Glu Tyr
            435                 440                 445

Gly Ile Asp Val Leu Val Glu Ile Ser Arg Phe Trp Ala Gly Arg Val
            450                 455                 460

His Phe Ser Lys Arg Lys Asn Lys Tyr Met Ile His Gly Val Thr Gly
465                 470                 475                 480

Pro Asn Glu Tyr Glu Asn Asn Val Asn Asn Trp Tyr Thr Asn Val
            485                 490                 495

Ile Ala Ala Trp Thr Leu Asp Tyr Thr Leu Gln Ser Leu Glu Arg Ile
            500                 505                 510
```

-continued

Ser Ala Glu Lys Arg Arg Leu Leu Asp Val Gln Glu Glu Leu Lys
        515                 520                 525

Val Trp Arg Glu Ile Ile Arg His Met Tyr Tyr Pro Tyr Ser Glu Glu
530                 535                 540

Leu Gln Ile Phe Val Gln His Asp Thr Phe Leu Asp Lys Asp Leu Gln
545                 550                 555                 560

Ser Val Asp Glu Leu Asp Pro Ala Glu Arg Pro Leu Tyr Gln Asn Trp
                565                 570                 575

Ser Trp Asp Lys Ile Leu Arg Ser Gly Phe Ile Lys Gln Ala Asp Val
            580                 585                 590

Leu Gln Gly Ile Tyr Leu Phe Pro Asp Arg Phe Ser Ile Asp Glu Lys
        595                 600                 605

Arg Arg Asn Tyr Glu Phe Tyr Glu Pro Met Thr Val His Glu Ser Ser
    610                 615                 620

Leu Ser Pro Ser Ile His Ala Val Leu Ala Ala Glu Leu Arg Met Glu
625                 630                 635                 640

Lys Lys Ala Leu Glu Leu Tyr Lys Arg Thr Ala Arg Leu Asp Leu Asp
                645                 650                 655

Asn Tyr Asn Arg Asp Thr Glu Glu Gly Leu His Ile Thr Ser Met Thr
            660                 665                 670

Gly Ser Trp Leu Ala Ile Val Gln Gly Phe Ala Gly Met Arg Thr Leu
        675                 680                 685

Lys Gly Thr Leu Ser Phe Thr Pro Phe Leu Pro Asn Glu Trp Asp Gly
    690                 695                 700

Tyr Ser Phe His Ile Asn Tyr Arg Asn Arg Leu Ile Lys Val Thr Val
705                 710                 715                 720

Glu Glu Arg Arg Ala Ile Phe Glu Leu Val Lys Gly Glu Pro Val Ser
                725                 730                 735

Ile Thr Val Tyr Gly Glu Pro Met Val Leu Asn Glu Arg Cys Glu Arg
            740                 745                 750

Arg Met Pro Asp Glu
        755

<210> SEQ ID NO 5
<211> LENGTH: 1100
<212> TYPE: PRT
<213> ORGANISM: Debaryomyces hansenii

<400> SEQUENCE: 5

Met Glu Tyr Asp Ser Ile Gly Glu Arg Phe Lys His Arg Thr Ile Ser
1               5                   10                  15

Lys Ile Asp Tyr Cys Asn Ile Phe Ile His Lys Phe Cys Lys Arg Gln
            20                  25                  30

Ile Val Ile Lys Thr Met Val Val Leu Asn Phe Ile Leu Ile Phe Val
        35                  40                  45

Leu Tyr Leu Tyr Tyr His Gly Ile Thr Tyr Ala Leu Pro Phe Thr Ile
    50                  55                  60

Lys Asp Ile Asp Ile Asp Asp Ser Phe Asn Asp Ser Thr Val Ser Phe
65                  70                  75                  80

Glu Thr Ile Glu Asn Asn Lys Lys Gln Leu Gly Ser Leu Ile Asn Ser
                85                  90                  95

Arg Glu Asn Lys Glu Ile Phe Leu Gln Leu Gln Asn Ser Gly Ser Ala
            100                 105                 110

Tyr Tyr Asp Pro Thr Ser Asn Thr Val Gly Thr Ala Glu Phe Pro Thr

```
            115                 120                 125
Tyr Asn Gln Tyr Gln Arg Gln Ala Tyr Val Ser Asn Gly Tyr Ile Gly
            130                 135                 140

Ser Arg Ile Pro Asn Leu Gly Gln Gly Phe Thr Phe Asp Gln Leu Ser
145                 150                 155                 160

Asp Ser Pro Asp Ala Val Glu Asp Leu Ser Asn Gly Trp Pro Leu
                165                 170                 175

Phe Asn Glu Arg Phe Ser Gly Ser Phe Ile Gly Gly Phe Tyr Asp Ile
                180                 185                 190

Gln Lys Asn Thr Thr Glu Thr Asn Phe Pro Glu Leu Ile Glu Lys Gly
            195                 200                 205

Tyr Glu Ser Ile Leu Ser Ala Val Pro Gln Trp Thr Thr Leu Thr Leu
            210                 215                 220

Ser Thr Val Lys Asn Gly Lys Thr Leu Ser Leu Asp Pro Ser Leu Ser
225                 230                 235                 240

Arg Asp Ser Gln Gly Asp Ile Ser Asn Tyr Ala Gln Asn Leu Ser Leu
                245                 250                 255

Ser Asn Gly Ile Val Thr Thr Glu Phe Thr Trp Leu Glu Ser Ile Gln
                260                 265                 270

Val His Phe Glu Val Val Ala His Arg Ser Asn Ile Asn Leu Gly Ile
            275                 280                 285

Val Asn Leu Arg Ile Val Asn Leu Asp Asn Ser Thr Val Asp Leu Lys
290                 295                 300

Val Glu Asp Lys Leu Asp Phe Ala Ser Thr Gln Arg Cys Gln Leu Ser
305                 310                 315                 320

Glu Val Gly Ser Asp Glu Gly Ile Phe Ile His Phe Gln Pro Asn
                325                 330                 335

Glu Ile Asp Tyr Val Asn Gly Ala Ile Tyr Ser Thr Leu Gln Tyr Asp
                340                 345                 350

Glu Met Ser Ser Asn Ala Ile Ser Arg Gly Ser Thr Asn Asp Thr Ser
            355                 360                 365

Thr Gln Lys Leu Asp Ile Ser Val Glu Pro Ser Lys Ser Phe Lys Ile
            370                 375                 380

Ser Lys Leu Val Gly Ile Val Ser Ser Asp Leu Asp Pro Glu Lys Tyr
385                 390                 395                 400

Lys Ser His Asn Thr Val Asn Asp Phe Ala Lys Glu Val Ala Thr Lys
                405                 410                 415

Gln Lys Asp Ser Val Ser Lys Leu Ile Lys Ser His Lys Val Gly Trp
                420                 425                 430

Ala Arg Thr Phe Glu Ser Ser Asn Ser Ile Thr Phe Ser Gly Asp Pro
            435                 440                 445

Leu Leu Thr Leu Ala Ser Arg Ala Ser Ile Tyr His Leu Asn Ala Asn
            450                 455                 460

Thr Arg Pro Gly Ala Gln Gly Val Thr Ala Ala Leu Pro Val Gly Gly
465                 470                 475                 480

Leu Ser Ser Asp Ser Tyr Gly Gly Met Val Phe Trp Asp Thr Asp Leu
                485                 490                 495

Trp Met Leu Asn Gly Leu Leu Pro Phe Asn Pro Asp His Ala Lys Ser
            500                 505                 510

Ile Val Asn Tyr Arg Ile His Thr His Glu Gln Ala Ile Lys Asn Val
            515                 520                 525

Pro Asn Asn Glu Ser Gly Ala Val Tyr Ser Trp Thr Ser Gly Arg Phe
            530                 535                 540
```

```
Gly Asn Cys Thr Ser Thr Gly Pro Cys Leu Asp Tyr Glu Tyr His Ile
545                 550                 555                 560

Asn Val Ala Val Ala Met Ala Ala Trp Glu Val Tyr Leu Ser Gly Ala
                565                 570                 575

Ala Asp Asp Asp Tyr Leu Asp Ser Val Ala Tyr Pro Leu Ile Asn Asp
            580                 585                 590

Ala Ala Thr Phe Leu Ala Asp Tyr Val Lys Tyr Asn Glu Ser Leu Ala
            595                 600                 605

Gln Tyr Val Ser His Asn Met Thr Asp Pro Asp Glu Tyr Ala Asn His
        610                 615                 620

Val Asp Asn Ala Ala Tyr Thr Asn Ala Gly Ile Ser Leu Leu Met Lys
625                 630                 635                 640

Trp Ala Ile Thr Ile Ser Asn His Leu Gly Lys Pro Val Pro Ser Lys
                645                 650                 655

Tyr Thr Asp Ile Ala Gly Ser Met His Ile Pro Thr Ser Asp Asn His
            660                 665                 670

Asp Asn Ile Thr Leu Glu Tyr Thr Gly Met Asn Ser Ser Val Gly Ile
        675                 680                 685

Lys Gln Ala Asp Val Ile Met Met Thr Tyr Pro Leu Gly Asn Glu Leu
690                 695                 700

Ile Ser Asp Asp Gln Ala Tyr Thr Asn Met Glu Phe Tyr Ser Met Lys
705                 710                 715                 720

Gln Val Ser Tyr Gly Pro Ala Met Thr Phe Pro Ile Phe Ser Ile Val
                725                 730                 735

Ala Ser Asn Leu Ser Pro Ser Gly Cys Ala Ser Gln Ser Tyr Leu His
            740                 745                 750

Lys Ala Val Gln Pro Phe Leu Arg Gly Pro Phe Ala Gln Phe Ser Glu
        755                 760                 765

Gln Asn Asn Asp Asn Phe Leu Thr Asn Gly Gly Thr His Pro Ala Phe
770                 775                 780

Pro Phe Met Thr Ala His Gly Gly Phe Leu Gln Ala Ile Leu Gln Gly
785                 790                 795                 800

Leu Thr Gly Leu Arg Phe Asp Phe Asp Leu Asp Asp Arg Asn Lys Leu
                805                 810                 815

Ser Arg Met Leu Thr Leu Asp Pro Ile Ser Leu Pro Cys Leu Gly Asn
            820                 825                 830

Gly Val Gln Phe Asp Ser Ile Lys Tyr Met Asn Gln Ser Ile Ser Leu
        835                 840                 845

Ala Ile Asn Glu Thr Ser Phe Ile Ile Lys His Asn Gly Pro Ile Ala
850                 855                 860

Gly Gly Asp Ser Asp Ser Ile Arg Ile Ser Leu Ala Lys Arg Asn Pro
865                 870                 875                 880

Lys Ser Gly Val Tyr Thr Leu Asp Lys Gly Glu Glu Leu Val Phe Pro
                885                 890                 895

Leu Phe Val Pro Thr Ala Gly Ser Gln Leu Ser Val Ser Glu Cys Ala
            900                 905                 910

Ser Ala Lys Phe Ile Asn Ile Thr Glu Ser Ala Tyr Gly Asp Ala Thr
        915                 920                 925

Val Leu Val Asn Asp Gly Asp Asn Thr Thr His Trp Gln Leu Lys Tyr
930                 935                 940

Asn Asp Thr Thr Ala Lys Ile Leu Val Asp Leu Lys Gln Ser Arg Asn
945                 950                 955                 960
```

```
Leu Thr Ser Gly Ala Ile Asn Trp Gly Asp Arg Pro Lys Ser Trp
            965                 970                 975

Ser Leu Leu Ala Phe Gly Ser Glu Glu Gln Ser Lys Ile Asn Asp Leu
        980                 985                 990

Asn Asp Val Ile Asp Phe Leu Ser Lys Val Asn Phe Gly Asn Asp Leu
        995                 1000                1005

Tyr Lys Lys Tyr Gln Phe Ile Asp Ala Gly Thr Ile Tyr Asp Gln
    1010                1015                1020

Asp Asp Val Phe Thr Thr Ile Val Ser Glu Glu Val Asp Ile Ser
    1025                1030                1035

Ala Pro Phe Asp Pro Lys Asp Tyr Ala Glu Val Lys Ile Pro Leu
    1040                1045                1050

Arg His Asn Thr Thr Ser Phe Asn Ile Glu Gln Gly Leu Gly Ala
    1055                1060                1065

Arg Phe Leu Leu Ile Glu Val Thr Asp Ile His Asp Thr Glu Pro
    1070                1075                1080

Ile Asp Asp Glu Thr Gly Gly Ala Lys Leu Tyr Glu Val Glu Phe
    1085                1090                1095

Phe Glu
    1100

<210> SEQ ID NO 6
<211> LENGTH: 1072
<212> TYPE: PRT
<213> ORGANISM: Aspergillus niger

<400> SEQUENCE: 6

Met Gln Val Lys Phe Leu Ala Thr Leu Leu Pro Leu Leu His Leu
1               5                   10                  15

Pro Ala Ala Val Asp Gly Leu Pro Gly Lys Asn Ala Arg Ile Ser Ala
            20                  25                  30

Ser Leu Lys Arg His Ala Gly Arg Asp Val Pro Gln Thr Ala Leu Asn
        35                  40                  45

Ser Thr Asn Val Tyr Gln Thr Lys Phe Ser Gly Val Thr Trp Asp Glu
    50                  55                  60

Asp His Trp Leu Leu Thr Thr Thr Pro Asp Gln Gly His Tyr Gln
65                  70                  75                  80

Ser Arg Gly Ser Val Ala Asn Gly Tyr Leu Gly Ile Asn Val Ala Asn
            85                  90                  95

Ile Gly Pro Phe Phe Glu Leu Asp Glu Pro Val Asn Gly Asp Val Ile
        100                 105                 110

Asn Gly Trp Pro Leu Tyr Ser Arg Arg Gln Ser Phe Ala Thr Ile Ser
        115                 120                 125

Gly Phe Trp Asp Arg Gln Ala His Thr Asn Gly Ser Asn Phe Pro Trp
    130                 135                 140

Leu Ser Gln Tyr Gly Asp Asp Ser Val Ile Ser Gly Val Pro His Trp
145                 150                 155                 160

Ser Gly Leu Ile Leu Asp Leu Gly Asp Asp Thr Tyr Leu Asp Ala Thr
            165                 170                 175

Val Asp Asn Arg Thr Ile Ser Asn Phe Lys Ser Thr Tyr Asp Phe Lys
        180                 185                 190

Ser Gly Val Leu Ser Trp Ser Tyr Thr Trp Thr Pro Gln Gly Asn Lys
        195                 200                 205

Gly Ser Tyr Ala Ile Thr Tyr Arg Leu Phe Ala His Lys Leu Tyr Val
    210                 215                 220
```

```
Asn Arg Ala Val Val Asp Met Glu Ile Thr Pro Leu Thr Asn Gly Asn
225                 230                 235                 240

Ala Thr Val Val Asn Val Leu Asp Gly Tyr Ala Ala Val Arg Thr Asp
            245                 250                 255

Phe Val Ala Ser Gly Gln Glu Gly Ala Ile Phe Ser Ala Val Arg
        260                 265                 270

Pro Trp Gly Val Asn Asn Val Thr Ala Tyr Val Tyr Ala Thr Leu Asp
        275                 280                 285

Gly Ser Asp Ser Val Asp Leu Ser Ser Arg Arg Ile Val Thr Asp Lys
        290                 295                 300

Pro Tyr Val Ser Thr Asn Ser Ser Val Ala Gln Ala Val Asp Val
305                 310                 315                 320

Met Phe Thr Ala Asn Glu Thr Val Arg Ile Thr Lys Phe Val Gly Gly
            325                 330                 335

Ala Thr Thr Asp Tyr Phe Leu Ala Thr Gln Glu Thr Ala Lys Ala Ala
            340                 345                 350

Cys Leu Ala Gly Leu Ala Asp Gly Tyr Val Lys Ser Leu Gln Ser His
            355                 360                 365

Val Gly Glu Trp Ala Thr Ile Met His Asp His Ser Val Asp Arg Phe
        370                 375                 380

Thr Asp Pro Ala Thr Gly Lys Leu Pro Glu Asp Ser His Ile Val Asp
385                 390                 395                 400

Ser Ala Ile Ile Ala Val Thr Asn Thr Tyr Tyr Leu Leu Gln Asn Thr
                405                 410                 415

Ala Gly Thr Asn Ala Ile Val Ala Ala Gly Gly Ile Pro Val Asn Val
            420                 425                 430

Asp Ser Cys Ala Pro Gly Gly Leu Thr Ser Asp Ser Tyr Gly Gly Gln
            435                 440                 445

Ile Phe Trp Asp Ala Asp Leu Trp Met Gln Pro Gly Leu Val Ala Ser
        450                 455                 460

His Pro Glu Ser Ala Gln Arg Phe Thr Asn Tyr Arg Ile Ala Leu His
465                 470                 475                 480

Tyr Gln Ala Gln Ala Asn Ile Glu Thr Ala Phe Thr Gly Ser Lys Asn
            485                 490                 495

Gln Thr Ser Phe Ser Ser Ser Ala Ala Ile Tyr Pro Trp Thr Ser Gly
        500                 505                 510

Arg Phe Gly Asn Cys Thr Ala Thr Gly Pro Cys Trp Asp Tyr Gln Tyr
        515                 520                 525

His Leu Asn Gly Asp Ile Gly Leu Ala Met Ile Asn Gln Trp Val Ala
        530                 535                 540

Ser Gly Asp Thr Ala Trp Phe Lys Asn Tyr Leu Phe Pro Ile Tyr Asp
545                 550                 555                 560

Ala Ala Ala Thr Leu Tyr Ser Glu Leu Val Glu Arg Asn Gly Ser Ser
            565                 570                 575

Trp Thr Leu Thr Asn Met Thr Asp Pro Asp Glu Tyr Ala Asn Ser Ile
            580                 585                 590

Asn Ala Gly Gly Tyr Thr Met Pro Leu Ile Ala Glu Thr Leu Gln Asn
        595                 600                 605

Ala Asn Lys Leu Arg Lys Gln Phe Gly Leu Glu Pro Asn Glu Thr Trp
        610                 615                 620

Asp Glu Ile Ala Glu Asp Val Leu Ile Leu Arg Glu Asn Gly Val Thr
625                 630                 635                 640
```

-continued

Leu Glu Tyr Thr Ser Met Asn Gly Ser Ala Val Val Lys Gln Ala Asp
            645                 650                 655

Ile Val Leu Asn Thr Phe Pro Leu Thr Tyr Glu Ser Asp Asn Tyr Thr
        660                 665                 670

Ala Thr Asn Ser Leu Thr Asp Leu Asp Tyr Tyr Ala Asn Lys Gln Ser
    675                 680                 685

Ala Asp Gly Pro Ala Met Thr Tyr Ala Ile Phe Ala Ile Val Ala Ser
690                 695                 700

Asp Val Ser Pro Ser Gly Cys Ser Ala Phe Thr Tyr His Gln Tyr Ser
705                 710                 715                 720

Tyr Ala Pro Tyr Ala Arg Gly Pro Trp Tyr Gln Leu Ser Glu Gln Met
                725                 730                 735

Ile Asp Asp Ala Ser Ile Asn Gly Gly Thr His Pro Ala Phe Pro Phe
            740                 745                 750

Leu Thr Gly His Gly Gly Ala Asn Gln Val Ala Leu Tyr Gly Tyr Leu
        755                 760                 765

Gly Leu Arg Leu His Pro Asp Asp Thr Ile Tyr Ile Asp Pro Asn Leu
    770                 775                 780

Pro Pro Gln Ile Pro His Ile Thr Tyr Arg Thr Phe Tyr Trp His Gly
785                 790                 795                 800

Trp Pro Ile Ser Ala Trp Ser Asn Tyr Thr His Thr Ile Gln Arg
                805                 810                 815

Asp Ser Ser Leu Ala Pro Leu Ala Ser Ala Asp Leu Leu Phe Ser Asn
            820                 825                 830

Val Ser Ile Lys Val Gln Val Gly Gln Ser Thr Ala Ser Ala Asp Glu
        835                 840                 845

Ala Thr Ile Tyr Tyr Leu Pro Leu Ser Gly Ala Leu Thr Val Pro Asn
    850                 855                 860

Arg Met Ile Gly Ser Val Asn Thr Thr Pro Gly Asn Gln Val Gln Cys
865                 870                 875                 880

His Pro Val Tyr Ser Pro Asp Ala Tyr Glu Pro Gly Gln Phe Pro Ile
                885                 890                 895

Ser Ala Val Asp Gly Ala Thr Ser Thr Lys Trp Gln Pro Ser Thr Ser
            900                 905                 910

Asp Leu Thr Ser Leu Thr Val Thr Leu Ser Thr Thr Ala Glu Ala Gly
        915                 920                 925

Ala Glu Glu Val Ser Gly Phe Tyr Phe Asp Trp Ser Gln Ala Pro Pro
    930                 935                 940

Glu Asn Leu Thr Val Ile Phe His Asp Ser Pro Ile Gly Asn Pro Ser
945                 950                 955                 960

Thr Val Phe Ala Ala Gly Ser Asn Ser Thr Gly Tyr Arg Val Ile
                965                 970                 975

Thr Ser Met Ser Asn Ile Val Gln Ser Lys Pro Tyr Asn Ala Ile Ser
            980                 985                 990

Ala Glu Glu Leu Asn Val Val Ser  Ile Pro Thr Ala Asn  Thr Thr Thr
        995                  1000                1005

Ile Thr Leu Asp Ala Pro Val  Gln Lys Ala Arg Tyr  Ala Thr Leu
    1010                 1015                1020

Leu Ile Ala Gly Asn Gln Ala  Asn Glu Thr Ala Gly  Ala Thr Val
    1025                 1030                1035

Ala Glu Trp Val Ile Leu Gly  Gln Asn Ser Thr Ser  Ser Ser Ser
    1040                 1045                1050

Ala Gln Ala Lys Arg Lys Met  Ser Ala Arg Ser Lys  Ala Thr Leu

-continued

```
            1055                1060                1065

Ala Gln   Leu Ser
     1070

<210> SEQ ID NO 7
<211> LENGTH: 1079
<212> TYPE: PRT
<213> ORGANISM: Trichoderma reesei

<400> SEQUENCE: 7

Met Arg Ser Thr Val Thr Ser Ala Ala Leu Leu Ser Leu Leu Gln
1               5                   10                  15

Leu Val Ser Pro Val His Gly Thr Thr Leu Val Asp Arg Val Thr Lys
            20                  25                  30

Cys Leu Ser Arg His Asp Gly Ser Asp Ala Glu Ser His Phe Ser Lys
            35                  40                      45

Asn Val Tyr Lys Thr Asp Phe Ala Gly Val Thr Trp Asp Glu Asp Asn
        50                  55                  60

Trp Leu Leu Ser Thr Thr Gln Leu Lys Gln Gly Ala Phe Glu Ala Arg
65                  70                  75                  80

Gly Ser Val Ala Asn Gly Tyr Leu Gly Ile Asn Val Ala Ser Val Gly
                85                  90                  95

Pro Phe Phe Glu Val Asp Thr Glu Glu Asp Gly Asp Val Ile Ser Gly
            100                 105                 110

Trp Pro Leu Phe Ser Arg Arg Gln Ser Phe Ala Thr Val Ala Gly Phe
        115                 120                 125

Trp Asp Ala Gln Pro Gln Met Asn Gly Thr Asn Phe Pro Trp Leu Ser
130                 135                 140

Gln Tyr Gly Ser Asp Thr Ala Ile Ser Gly Ile Pro His Trp Ser Gly
145                 150                 155                 160

Leu Val Leu Asp Leu Gly Gly Gly Thr Tyr Leu Asp Ala Thr Val Ser
                165                 170                 175

Asn Lys Thr Ile Ser His Phe Arg Ser Thr Tyr Asp Tyr Lys Ala Gly
            180                 185                 190

Val Leu Ser Trp Ser Tyr Lys Trp Thr Pro Lys Gly Asn Lys Gly Ser
        195                 200                 205

Phe Asp Ile Ser Tyr Arg Leu Phe Ala Asn Lys Leu His Val Asn Gln
210                 215                 220

Ala Val Val Asp Met Gln Val Thr Ala Ser Lys Asn Val Gln Ala Ser
225                 230                 235                 240

Ile Val Asn Val Leu Asp Gly Phe Ala Ala Val Arg Thr Asp Phe Val
                245                 250                 255

Glu Ser Gly Glu Asp Gly Ser Ala Ile Phe Ala Ala Val Arg Pro Asn
            260                 265                 270

Gly Val Ala Asn Val Thr Ala Tyr Val Tyr Ala Asp Ile Thr Gly Ser
        275                 280                 285

Gly Gly Val Asn Leu Ser Ser Arg Lys Ile Val His Asn Lys Pro Tyr
290                 295                 300

Val His Ala Asn Ala Ser Ser Ile Ala Gln Ala Val Pro Val Lys Phe
305                 310                 315                 320

Ala Ala Gly Arg Thr Val Arg Val Thr Lys Phe Val Gly Ala Ala Ser
                325                 330                 335

Ser Asp Ala Phe Lys Asn Pro Lys Gln Val Ala Lys Lys Ala Ala Ala
            340                 345                 350
```

-continued

Ala Gly Leu Ser Asn Gly Tyr Thr Lys Ser Leu Lys Ala His Val Glu
        355                 360                 365

Glu Trp Ala Thr Val Met Pro Glu Ser Ser Val Asp Ser Phe Ala Asp
370                 375                 380

Pro Lys Thr Gly Lys Leu Pro Ala Asp Ser His Ile Val Asp Ser Ala
385                 390                 395                 400

Ile Ile Ala Val Thr Asn Thr Tyr Leu Leu Gln Asn Thr Val Gly
                405                 410                 415

Lys Asn Gly Ile Lys Ala Val Asp Gly Ala Pro Val Asn Val Asp Ser
            420                 425                 430

Ile Ser Val Gly Gly Leu Thr Ser Asp Ser Tyr Ala Gly Gln Ile Phe
            435                 440                 445

Trp Asp Ala Asp Leu Trp Met Gln Pro Gly Leu Val Ala Ala His Pro
        450                 455                 460

Glu Ala Ala Glu Arg Ile Thr Asn Tyr Arg Leu Ala Arg Tyr Gly Gln
465                 470                 475                 480

Ala Lys Glu Asn Val Lys Thr Ala Tyr Ala Gly Ser Gln Asn Glu Thr
                485                 490                 495

Phe Phe Ser Ala Ser Ala Ala Val Phe Pro Trp Thr Ser Gly Arg Tyr
            500                 505                 510

Gly Asn Cys Thr Ala Thr Gly Pro Cys Trp Asp Tyr Glu Tyr His Leu
        515                 520                 525

Asn Gly Asp Ile Gly Ile Ser Leu Val Asn Gln Trp Val Val Asn Gly
        530                 535                 540

Asp Thr Lys Asp Phe Glu Lys Asn Leu Phe Pro Val Tyr Asp Ser Val
545                 550                 555                 560

Ala Gln Leu Tyr Gly Asn Leu Leu Arg Pro Asn Lys Thr Ser Trp Thr
                565                 570                 575

Leu Thr Asn Met Thr Asp Pro Asp Glu Tyr Ala Asn His Val Asp Ala
            580                 585                 590

Gly Gly Tyr Thr Met Pro Leu Ile Ala Glu Thr Leu Gln Lys Ala Asn
        595                 600                 605

Ser Phe Arg Gln Gln Phe Gly Ile Glu Gln Asn Lys Thr Trp Asn Asp
610                 615                 620

Met Ala Ser Asn Val Leu Val Leu Arg Glu Asn Gly Val Thr Leu Glu
625                 630                 635                 640

Phe Thr Ala Met Asn Gly Thr Ala Val Val Lys Gln Ala Asp Val Ile
                645                 650                 655

Met Leu Thr Tyr Pro Leu Ser Tyr Gly Thr Asn Tyr Ser Ala Gln Asp
            660                 665                 670

Ala Leu Asn Asp Leu Asp Tyr Tyr Ala Asn Lys Gln Ser Pro Asp Gly
        675                 680                 685

Pro Ala Met Thr Tyr Ala Phe Phe Ser Ile Val Ala Asn Glu Ile Ser
690                 695                 700

Pro Ser Gly Cys Ser Ala Tyr Thr Tyr Ala Gln Asn Ala Phe Lys Pro
705                 710                 715                 720

Tyr Val Arg Ala Pro Phe Tyr Gln Ile Ser Glu Gln Leu Ile Asp Asp
                725                 730                 735

Ala Ser Val Asn Gly Gly Thr His Pro Ala Tyr Pro Phe Leu Thr Gly
            740                 745                 750

His Gly Gly Ala His Gln Val Val Leu Phe Gly Tyr Leu Gly Leu Arg
        755                 760                 765

Leu Val Pro Asp Asp Val Ile His Ile Glu Pro Asn Leu Pro Pro Gln

```
              770                 775                 780
Ile Pro Tyr Leu Arg Tyr Arg Thr Phe Tyr Trp Arg Gly Trp Pro Ile
785                 790                 795                 800

Ser Ala Trp Ser Asn Tyr Thr His Thr Thr Leu Ser Arg Ala Ala Gly
                805                 810                 815

Val Ala Ala Leu Glu Gly Ala Asp Gln Arg Phe Ala Arg Lys Pro Ile
                820                 825                 830

Thr Ile His Ala Gly Pro Glu Gln Asp Pro Thr Ala Tyr Arg Leu Pro
                835                 840                 845

Val Lys Gly Ser Val Val Ile Pro Asn Lys Gln Ile Gly Ser Gln Gln
                850                 855                 860

Thr Tyr Ala Gly Asn Leu Val Gln Cys His Ala Ala Ser Ser Pro Asn
865                 870                 875                 880

Asp Tyr Val Pro Gly Gln Phe Pro Ile Ala Ala Val Asp Gly Ala Thr
                885                 890                 895

Ser Thr Lys Trp Gln Pro Ala Ser Ala Asp Lys Val Ser Ser Ile Thr
                900                 905                 910

Val Ser Leu Asp Lys Glu Asp Val Gly Ser Leu Val Ser Gly Phe His
                915                 920                 925

Phe Asp Trp Ala Gln Ala Pro Pro Val Asn Ala Thr Val Ile Phe His
                930                 935                 940

Asp Glu Ala Leu Ala Asp Pro Ala Thr Ala Leu Ala Ser Ala His Lys
945                 950                 955                 960

His Asn Ser Lys Tyr Thr Thr Val Thr Ser Leu Thr Asn Ile Glu Leu
                965                 970                 975

Ser Asp Pro Tyr Val Ser Thr Lys Asp Leu Asn Ala Ile Ala Ile Pro
                980                 985                 990

Ile Gly Asn Thr Thr Asn Val Thr  Leu Ser His Pro Val  Ala Ala Ser
                995                 1000                1005

Arg Tyr  Ala Ser Leu Leu Ile  Val Gly Asn Gln Gly  Leu Asp Pro
     1010                1015                1020

Val Asp  Val Lys Ala Lys Asn  Gly Thr Gly Ala Thr  Val Ala Glu
     1025                1030                1035

Trp Ala  Ile Phe Gly His Gly  Lys Glu His Ser Gly  Lys Pro Ser
     1040                1045                1050

Ser His  Ser Lys Arg Arg Leu  Asn Val Arg Thr Ala  Ala Thr Leu
     1055                1060                1065

Ser Asn  Pro Arg Ser Phe Met  Arg Arg Arg Leu
     1070                1075

<210> SEQ ID NO 8
<211> LENGTH: 1147
<212> TYPE: PRT
<213> ORGANISM: Kluyveromyces lactis

<400> SEQUENCE: 8

Met Leu Ile Val Pro Phe Ile Leu Phe Ser Val Ala Ile Leu Ala Pro
1               5                   10                  15

Ile Tyr Phe Tyr Leu Thr Lys Pro Leu Pro Leu Gln His Thr His Phe
                20                  25                  30

Gly Ser Phe Val Cys Ala Glu Asp Thr Leu Phe Cys Pro Glu Ser Gln
                35                  40                  45

Arg Lys Ala Ser Glu Lys Met Tyr Ser Leu Leu Lys Asp His Glu Asn
                50                  55                  60
```

-continued

```
Thr Phe Tyr Asp Glu Glu Gln Gln Ile Leu Gly Asn Leu Leu Leu Ser
 65                  70                  75                  80

Glu Asn Thr Phe Ser Arg Gln Pro Tyr Val Ala Asn Gly Tyr Ile Gly
                 85                  90                  95

Ser Arg Ile Pro Asn Leu Gly Phe Gly Tyr Ala Leu Asp Thr Ile Asn
            100                 105                 110

Val Trp Val Asn Asp Ser Ser Ile Pro Gly Ala Leu Asp Asn Gly Trp
        115                 120                 125

Pro Leu Arg Asn Gln Arg Phe Ala Gly Ala Phe Ile Ser Asp Phe Tyr
    130                 135                 140

Cys Leu Gln Glu Lys Leu Asn Ser Thr Asn Phe Pro Glu Leu Asp Asp
145                 150                 155                 160

Asp Gly Tyr Ser Thr Val Ile Ser Thr Ile Pro Gln Trp Thr Asp Leu
                165                 170                 175

Ser Ile Leu Lys His Thr Thr Thr Gly Gln Ile Glu Tyr Ile Asn Pro
            180                 185                 190

Thr Asp Val Lys Leu Asp Lys Ile Thr Asn Tyr Met Gln Asn Leu Ser
        195                 200                 205

Leu Gln Asp Gly Ile Val Thr Thr Thr Phe Val Tyr Asp Lys Gln Leu
    210                 215                 220

Leu Val Thr Thr Lys Val Val Ala His Arg Lys Ile Tyr Pro Leu Gly
225                 230                 235                 240

Val Val Thr Leu Glu Leu Ser Leu Phe Asp Asn Ser Asp Thr Ser
                245                 250                 255

Ala Asp Asn Glu Asn Glu Tyr Val Glu Leu Glu Ile Cys Asp Ser Leu
            260                 265                 270

Asn Phe Ser Thr Ser His Arg Thr Val Leu Asn Asp Tyr Gly Tyr Asp
        275                 280                 285

Gln Asn Asn Glu Gly Ile Phe Met Val Val Glu Pro Glu Asn Val Pro
    290                 295                 300

Tyr Ser Asn Ala Ser Leu Phe Ser Tyr Phe Asp Ile Pro Ser Arg Asp
305                 310                 315                 320

Thr Leu Thr Leu Ser Lys Tyr Ser Asp Ser Ile Ser Gln Cys Thr Thr
                325                 330                 335

Gln Ile Leu Lys Ala Asn Ser Thr Phe Val Ala His Lys Tyr Ile Gly
            340                 345                 350

Ile Ile Ser Ser Glu Tyr Asp Asn Lys Gln Pro Asp Asn Ser Asn
        355                 360                 365

Gly Thr Ser Asn Glu Ala Leu Lys Met Ser Asn Leu Glu Arg Ala Thr
    370                 375                 380

Ser Ile Val Leu Asp Asn Lys Gly Asn Tyr Asp Ser Leu Ile Gln Ser
385                 390                 395                 400

His Lys Asn Ala Trp Lys Arg Ile Tyr Lys Asp Ala Ser Ile Glu Ile
                405                 410                 415

Pro Ser Asp Gly Leu Leu Glu Met Thr Ala Lys Ser Ser Ile Tyr His
            420                 425                 430

Leu Leu Ala Asn Thr Arg Ser His Asn Val Ser Glu Asp Arg Gly Leu
        435                 440                 445

Pro Ile Gly Val Ser Gly Leu Ser Ser Asp Ser Tyr Gly Gly Met Val
    450                 455                 460

Phe Trp Asp Ser Asp Leu Trp Ile Leu Pro Ala Leu Leu Pro Phe Phe
465                 470                 475                 480

Pro Asn Ala Ala Arg Gln Ile Asn Asn Tyr Arg Asn Ala Ser Leu His
```

```
                485                 490                 495
Gln Ala Lys Leu Asn Ala Glu Lys Tyr Gly Tyr Asp Gly Ala Leu Tyr
            500                 505                 510
Pro Trp Thr Ser Gly Arg Tyr Ala Asn Cys Thr Ser Thr Gly Pro Cys
            515                 520                 525
Val Asp Tyr Glu Tyr His Ile Asn Val Asp Ile Ala Leu Ser Ser Phe
            530                 535                 540
Ala Ile Tyr Met Asn Gly Asp Glu Asp Glu Arg Ser Glu Tyr
545                 550                 555                 560
Leu Arg Tyr Thr Thr Trp Pro Phe Val Glu Asn Ala Ala Lys Met Phe
                565                 570                 575
Ala Gln Tyr Val Lys Trp Asn Asp Thr Met Gln Gln Tyr Thr Thr His
            580                 585                 590
Asn Leu Thr Asp Pro Asp Glu Tyr Ala Asn Phe Val Asp Asn Ala Ala
            595                 600                 605
Phe Thr Asn Ala Gly Ile Gln Ser Val Met Val Trp Ala His Asp Ile
        610                 615                 620
Ala Arg His Leu Gly Ile Asp Pro Asp Pro Gln Trp Leu Glu Ile Ala
625                 630                 635                 640
Asp Asn Ile His Ile Pro Ile Ser Glu Thr Asn Ile Thr Leu Glu Tyr
                645                 650                 655
Ser Gly Met Asn Ser Ser Val Glu Ile Lys Gln Ala Asp Val Val Leu
            660                 665                 670
Met Ile Tyr Pro Leu Ser Tyr Ile Thr Asp Gln Ser Ile Leu Asn Asn
        675                 680                 685
Ala Ile Lys Asn Leu Tyr Tyr Tyr Ser Glu Arg Gln Ser Ala Ser Gly
        690                 695                 700
Pro Ala Met Thr Tyr Pro Val Phe Val Ala Gly Ala Ala Ser Leu Leu
705                 710                 715                 720
Asn Tyr Gly Ser Ser Ser Gln Ser Tyr Leu Tyr Lys Ser Val Val Pro
            725                 730                 735
Tyr Leu Arg Ser Pro Phe Ala Gln Phe Ser Glu Gln Ser Asp Asp Asn
            740                 745                 750
Phe Leu Thr Asn Gly Leu Thr Gln Pro Ala Phe Pro Phe Leu Thr Ala
        755                 760                 765
Asn Gly Gly Phe Leu Gln Ser Ile Leu Phe Gly Leu Thr Gly Leu Arg
        770                 775                 780
Tyr Ser Tyr Glu Val Asp Glu Asp Thr Gly Lys Ile His Arg Leu Leu
785                 790                 795                 800
Lys Phe Asn Pro Ile Gln Leu Pro Leu Leu Pro Gly Gly Ile Arg Ile
            805                 810                 815
Asn Asn Phe Lys Tyr Met Gly Gln Val Leu Asp Val Leu Ile Thr Asp
        820                 825                 830
Thr Glu Gly Ile Ile Ile His Lys Asn Gly Thr Lys Glu Ile Arg Ile
        835                 840                 845
Lys Val Pro Asp Arg Thr Leu Ile Pro Asp Val Asp Val Lys Tyr Ser
        850                 855                 860
Glu Glu Thr Asp Pro Ile Lys Gln Ile Leu His Gly Arg Arg Ser Val
865                 870                 875                 880
Pro Thr Gly Lys Asn Tyr Phe Thr Ile Gln Pro Gly Asp Val Phe Lys
                885                 890                 895
Thr Pro Leu Tyr Ile Pro Lys Lys Asn Leu Glu Gly Asn Leu Val Glu
            900                 905                 910
```

```
Ala Lys Gln Ile Thr Asn Leu Thr Ala Gly Val Pro Gly Asp Val Ala
        915                 920                 925

Val Ser Val Ile Asp Gly Asn Asn Phe Thr His Trp Gln Pro Ala Tyr
    930                 935                 940

Lys Asn Leu Pro Ala Arg Leu Leu Ile Asp Met Gly Asn Asn Phe Thr
945                 950                 955                 960

Gln Glu Ile Lys Ser Gly Lys Ile Ile Trp Gly Ser Arg Pro Ala Lys
                965                 970                 975

Thr Phe Ser Leu Ser Ile Leu Pro Gln Thr Glu Glu Val Phe Lys Asn
                980                 985                 990

Leu Thr His Ile Leu Ser Asn Val Asn Gln Tyr Cys Asn Lys Thr Gly
            995                1000               1005

Asp Glu Cys Val Arg Asp Leu Glu Arg Thr Glu Lys Gly Phe Asp
        1010                1015                1020

Ala Ala Ile Glu Asp Val Phe Asp Trp Tyr Gly Ile Asp Pro Asp
        1025                1030                1035

Ser Ile Ile Ser Thr His Pro Glu Leu Lys Asp Met Lys Thr Lys
        1040                1045                1050

Phe Val Lys Ile Leu Asp His Tyr Lys Val Thr Pro Ser Glu Pro
        1055                1060                1065

Tyr Pro Trp Arg Val Tyr Asn Glu Ser Gln Ile Val Leu Leu Pro
        1070                1075                1080

Gly Asn Glu Thr Asp Phe Asp Ile Asp Tyr Ser Lys Val Ala Glu
        1085                1090                1095

Met Asn Pro Glu Asn Val Asp Ile Asp Phe Arg Gly Asn Gln Thr
        1100                1105                1110

Asp Trp Arg Lys Gly Arg Phe Ile Val Leu Thr Val His Asp Thr
        1115                1120                1125

Tyr Asp Asp Asp Asp Glu Lys Gly Ala Thr Ile Lys Glu Phe
        1130                1135                1140

Ala Leu Phe Pro
        1145

<210> SEQ ID NO 9
<211> LENGTH: 735
<212> TYPE: PRT
<213> ORGANISM: Schizosaccharomyces pombe

<400> SEQUENCE: 9

Met Pro Ser Lys Phe Ser Ser Lys Tyr Val Thr Glu Ala Ile Ser
1               5                   10                  15

Asn Asp Asp Asp Asn Pro Phe Ala Thr Ala Lys Ser Tyr Tyr Ser Lys
                20                  25                  30

Asp Thr Asp Leu Ser Thr Arg Val Ser Ala Gly Arg Pro Arg Thr Leu
            35                  40                  45

Ser Thr Ser Met Glu Ala Ser Ala Pro Thr Ile Pro Glu Leu Lys
        50                  55                  60

Asn Leu Arg Arg Arg Gly Ser Leu Asp Glu His Lys Gln Pro Arg Lys
65                  70                  75                  80

Phe Leu Val Asp Val Asp Lys Thr Leu Asn Ala Leu Leu Glu Ser Glu
                85                  90                  95

Asp Thr Asp Arg Asn Met Gln Ile Thr Ile Glu Asp Thr Gly Pro Lys
            100                 105                 110

Val Val Ser Leu Gly Ser Ala Ser Ser Gly Gly Tyr Arg Leu Tyr Glu
```

-continued

```
            115                 120                 125
Leu Arg Gly Thr Tyr Gln Leu Ser Asn Leu Leu Gln Glu Leu Thr Leu
        130                 135                 140
Ala Lys Asp Tyr Gly Arg Arg Tyr Ile Leu Leu Asp Glu Arg Arg Leu
145                 150                 155                 160
Asn Glu Asn Pro Val Asn Arg Leu Ser Arg Leu Ile Lys Gly Thr Phe
                165                 170                 175
Trp Asp Ala Leu Thr Arg Arg Ile Asp Ala Ser Val Leu Asp Val Ile
                180                 185                 190
Cys Arg Asp Thr Lys Asp Arg Ser Gly Ser His Val Asn Arg Ile Tyr
                195                 200                 205
Val Pro Lys Ala Glu Gln Glu Met Tyr Glu Tyr Val Arg Ala Ala
    210                 215                 220
Lys Glu Arg Pro Tyr Leu Asn Leu Gln Val Tyr Leu Pro Glu Glu
225                 230                 235                 240
Ile Thr Pro Glu Trp Val Arg Asp Val Asn Asp Lys Pro Gly Leu Leu
                245                 250                 255
Ala Leu Ala Met Glu Lys Tyr Gln Asp Asp Glu Gly Asn Thr His Leu
                260                 265                 270
Arg Gly Val Pro Phe Val Val Pro Gly Gly Arg Phe Asn Glu Leu Tyr
        275                 280                 285
Gly Trp Asp Ser Tyr Phe Glu Ser Leu Gly Leu Leu Val Asp Asp Arg
        290                 295                 300
Val Asp Leu Ala Lys Gly Met Val Glu Asn Phe Ile Phe Glu Ile Thr
305                 310                 315                 320
Tyr Tyr Gly Lys Ile Leu Asn Ala Asn Arg Thr Tyr Tyr Leu Leu Arg
                325                 330                 335
Ser Gln Pro Pro Phe Leu Thr Asp Met Ala Leu Arg Val Tyr Glu Arg
                340                 345                 350
Ile Lys Asn Glu Glu Gly Ser Leu Asp Phe Leu His Arg Ala Phe Ser
                355                 360                 365
Ala Thr Ile Lys Glu Tyr His Thr Val Trp Thr Ala Thr Pro Arg Leu
        370                 375                 380
Asp Pro Lys Thr Gly Leu Ser Arg Tyr Arg Pro Gly Gly Leu Gly Ile
385                 390                 395                 400
Pro Pro Glu Thr Glu Ala Ser His Phe Glu His Leu Leu Arg Pro Tyr
                405                 410                 415
Met Glu Lys Tyr His Met Thr Leu Glu Glu Phe Thr His Ala Tyr Asn
                420                 425                 430
Tyr Gln Gln Ile His Glu Pro Ala Leu Asp Glu Tyr Phe Val His Asp
        435                 440                 445
Arg Ala Val Arg Glu Ser Gly His Asp Thr Thr Tyr Arg Leu Glu Lys
        450                 455                 460
Val Cys Ala Asp Leu Ala Thr Val Asp Leu Asn Ser Leu Leu Tyr Lys
465                 470                 475                 480
Tyr Glu Thr Asp Ile Ser His Val Ile Leu Glu Tyr Phe Asp Lys
                485                 490                 495
Phe Val Leu Pro Asn Gly Thr Ile Glu Thr Ser Ala Ile Trp Asp Arg
                500                 505                 510
Arg Ala Arg Ala Arg Arg Ala Ala Met Glu Lys Tyr Leu Trp Ser Glu
        515                 520                 525
Ala Asp Ser Met Trp Tyr Asp Tyr Asn Thr Lys Leu Glu Thr Lys Ser
        530                 535                 540
```

```
Thr Tyr Glu Ser Ala Thr Ala Phe Trp Ala Leu Trp Ala Gly Val Ala
545                 550                 555                 560

Thr Pro Arg Gln Ala Ala Lys Phe Val Asp Val Ser Leu Pro Lys Phe
                565                 570                 575

Glu Val Ala Gly Gly Ile Val Ala Gly Thr Lys Arg Ser Leu Gly Lys
                580                 585                 590

Val Gly Leu Asp Asn Pro Ser Arg Gln Trp Asp Tyr Pro Asn Gly Trp
            595                 600                 605

Ser Pro Gln Gln Ile Leu Ala Trp Tyr Gly Leu Ile Arg Tyr Gly Tyr
        610                 615                 620

Glu Glu Glu Thr Arg Arg Leu Val Tyr Arg Trp Leu Tyr Thr Ile Thr
625                 630                 635                 640

Lys Ser Phe Val Asp Phe Asn Gly Ile Val Glu Lys Tyr Asp Leu
                645                 650                 655

Thr Arg Pro Val Asp Pro His Arg Val Glu Ala Glu Tyr Gly Asn Gln
                660                 665                 670

Gly Val Asn Ile Lys Gly Val Ala Arg Glu Gly Phe Gly Trp Val Asn
            675                 680                 685

Ala Ser Tyr Glu Val Gly Leu Thr Phe Cys Asn Ser His Met Arg Arg
        690                 695                 700

Ala Leu Gly Ala Cys Thr Thr Pro Asp Val Phe Phe Ala Gly Ile Lys
705                 710                 715                 720

Glu Glu Ser Leu Pro Ala Phe Glu Asn Leu Ser Ile His Lys Asn
                725                 730                 735

<210> SEQ ID NO 10
<211> LENGTH: 744
<212> TYPE: PRT
<213> ORGANISM: Neurospora crassa

<400> SEQUENCE: 10

Met Thr Ser Gln Pro Ser Ser Gly Lys Gly Arg Gly Arg Asn Leu Ser
1               5                   10                  15

Ile Asp Glu Tyr Asn Val Tyr Asp Asp Ala Lys Thr Tyr Tyr Thr Thr
            20                  25                  30

Glu Asp Arg His His Asn His Arg Ala Gly Ala Arg Thr Arg Thr Tyr
        35                  40                  45

Ser Gln Asn Ser Leu Phe Lys Gln Phe Glu Arg Leu Gly Leu Gln Lys
    50                  55                  60

Glu Pro Tyr Arg Arg Gly Ser His Asp Glu Ser Thr Ile Pro Gln Ser
65                  70                  75                  80

Arg Arg Phe Leu Ile Gln Val Glu Pro Thr Leu Gln Ser Leu Gln Ser
                85                  90                  95

Gln Glu Asp Thr Asp Gly Asn Met Gln Ile Thr Ile Glu Asp Asn Gly
            100                 105                 110

Pro Lys Val Leu Ser Leu Arg Thr Ala Ala Ser Asn Gly Tyr Asn Arg
        115                 120                 125

Phe Asp Ile Arg Gly Thr Tyr Met Leu Ser Asn Leu Leu Gln Glu Leu
    130                 135                 140

Tyr Leu Ala Lys Glu Tyr Gly Arg Lys Gln Ile Ile Leu Asp Glu Ala
145                 150                 155                 160

Arg Leu Asn Glu Asn Pro Val Asn Arg Leu Ser Arg Leu Ile Lys Asp
                165                 170                 175

His Phe Trp Glu Gly Leu Thr Arg Arg Ile Asp Ala Ser Ser Ile Glu
```

-continued

```
                180                 185                 190
Ile Ala Ala Arg Asp Pro Lys Asp Trp Thr Asp Pro Arg Pro Arg
            195                 200                 205
Ile Tyr Ile Pro Arg Gly Ala Pro Glu Gln His Glu Tyr Tyr Thr Lys
        210                 215                 220
Val Ala Leu Asp Arg Pro Glu Leu Arg Leu Asp Val Gln Tyr Leu Pro
225                 230                 235                 240
Glu Lys Ile Thr Pro Glu Ile Val Arg Asp Met Asn Ala Lys Pro Gly
                245                 250                 255
Leu Leu Ala Val Asp Met Glu Val Val Asp Pro Lys Thr Gly Glu
            260                 265                 270
Lys Thr Leu Arg Gly Arg Pro Phe Val Val Pro Gly Gly Arg Phe Asn
        275                 280                 285
Glu Leu Tyr Gly Trp Asp Ser Tyr Met Glu Ser Leu Gly Leu Leu Val
            290                 295                 300
Asn Asp Arg Val Asp Leu Ala Lys Ser Met Val Gln Asn Phe Cys Phe
305                 310                 315                 320
Cys Ile Lys His Tyr Gly Lys Ile Leu Asn Ala Thr Arg Ser Tyr Tyr
                325                 330                 335
Leu Cys Arg Ser Gln Pro Pro Phe Leu Thr Asp Met Thr Leu Arg Val
            340                 345                 350
Tyr Asp Lys Ile Lys His Glu Pro Gly Ala Leu Glu Phe Leu Arg Gln
            355                 360                 365
Ser Leu Leu Ala Ala Ile Lys Glu Tyr Tyr Ser Val Trp Thr Ala Glu
        370                 375                 380
Pro Arg Leu Asp Pro Val Thr Gly Leu Ser Arg Tyr Arg Pro Glu Gly
385                 390                 395                 400
Leu Gly Val Pro Pro Glu Thr Glu Ala Gly His Phe Ile His Ile Leu
                405                 410                 415
Glu Pro Tyr Ala Lys Lys His Asn Met Ser Phe Asp Glu Phe Val Tyr
                420                 425                 430
Ala Tyr Asn His Gly Glu Ile Lys Glu Pro Thr Leu Asp Asp Tyr Phe
            435                 440                 445
Met His Asp Arg Ala Val Arg Glu Ser Gly His Asp Thr Thr Tyr Arg
450                 455                 460
Phe Glu Gly Ile Cys Ala Asp Leu Ala Thr Ile Asp Leu Asn Ser Leu
465                 470                 475                 480
Leu Phe Lys Tyr Glu Thr Asp Ile Ala Arg Thr Ile Arg Asn Val Phe
            485                 490                 495
His Asp Lys Phe Glu Val Pro Asp Asp Trp Leu Ala Thr Asn Asn Pro
            500                 505                 510
Ala Ala Ser Lys Leu Glu Thr Ser Ala Met Trp Asp Arg Ala Lys
            515                 520                 525
Arg Arg Lys Leu Ala Ile Asp Lys Tyr Leu Trp Asn Glu Ala Gly
        530                 535                 540
Met Tyr Phe Asp Tyr Asn Thr Ala Thr Arg Lys Gln Cys Asn Tyr Glu
545                 550                 555                 560
Ser Ala Thr Thr Phe Trp Ala Leu Trp Ala Gly Val Ser Asn Pro Lys
                565                 570                 575
Gln Ala Ala Ala Met Val Thr Lys Ala Leu Pro Lys Leu Glu Ala Phe
            580                 585                 590
Gly Gly Leu Leu Ser Gly Thr Lys Glu Ser Arg Gly Glu Ile Gly Leu
            595                 600                 605
```

-continued

```
Glu Arg Pro Asn Arg Gln Trp Asp Tyr Pro Tyr Gly Trp Ala Pro Gln
    610                 615                 620

Gln Ile Leu Ala Trp Thr Gly Leu Tyr Arg Tyr Gly Phe Asn Glu Glu
625                 630                 635                 640

Ala Glu Arg Leu Ala Tyr Lys Trp Leu Phe Met Ile Thr Lys Ala Phe
                645                 650                 655

Val Asp Phe Asn Gly Val Val Glu Lys Tyr Asp Val Thr Arg Pro
            660                 665                 670

Ile Asp Pro His Arg Val Asp Ala Glu Tyr Gly Asn Gln Gly Leu Asp
        675                 680                 685

Phe Lys Gly Val Ala Lys Glu Gly Phe Gly Trp Val Asn Ala Ser Tyr
    690                 695                 700

Val Tyr Gly Leu Gln Ile Val Asn Ala His Met Arg Arg Ala Leu Gly
705                 710                 715                 720

Thr Leu Thr Pro Tyr Glu Thr Phe Met Lys Ala Val Glu Glu Asn Arg
                725                 730                 735

Asn Lys Ala Leu Ser Glu Leu Val
            740

<210> SEQ ID NO 11
<211> LENGTH: 907
<212> TYPE: PRT
<213> ORGANISM: Candida albicans

<400> SEQUENCE: 11

Met Phe Thr Lys Asn His Arg Arg Met Ser Ser Thr Ser Ser Asp Asp
1               5                   10                  15

Asp Pro Phe Asp Val Ala Glu Lys Tyr Tyr Gly Glu Glu Arg Lys Lys
            20                  25                  30

Lys Leu Asn Arg Val Arg Thr Phe Ser Ala Phe Glu Ser Thr Lys Tyr
        35                  40                  45

Gly Ala Gly Pro Ile Ser Pro Leu Arg Pro Thr Tyr Glu Pro Pro
    50                  55                  60

Val Ile Lys Glu Thr Ser Glu Pro Leu Ser Ser Ser Ser Thr Ser
65                  70                  75                  80

Ser Pro Pro Thr Leu Thr Pro Gln Thr Ser Gln Val Gln Phe Asn Leu
                85                  90                  95

Gly Val Gly Lys Thr Lys Asn Gly Ser Ala Ile His Ser Asp Ser Glu
            100                 105                 110

Glu Glu Glu Asp Glu Asp Pro Val Ser Asn Thr Lys Lys Gly Glu
        115                 120                 125

Ala Asp Glu Lys Asp Pro Phe Asp Thr Thr Asp Ser Lys Leu Glu Asn
    130                 135                 140

Glu Asn Ser Thr Pro Ser Ser Ile Thr Gly Lys Glu Ile Ile Pro His
145                 150                 155                 160

Pro Thr Gly Phe Arg Gly Ser Ser Glu Glu Ser Ala Ile Arg Arg Lys
                165                 170                 175

Pro Ser Ile Ile Pro Ile Tyr His Asp Asn Ile Ser Gln Glu Ser Val
            180                 185                 190

Ile Arg Asn Ala Asn Thr Pro Thr Thr Tyr Asn Arg Glu Lys Phe His
        195                 200                 205

Leu Arg Arg Gly Ser Leu Asp Glu Ser Thr Phe Ile Arg Pro Lys Lys
    210                 215                 220

Tyr Tyr Ile Asn Asp Val Gln Gly Thr Leu Arg Glu Leu Leu Ala Asn
```

```
            225                 230                 235                 240
Glu Asp Thr Asp Asn Asn Cys Gln Ile Thr Ile Glu Asp Thr Gly Pro
                    245                 250                 255

Lys Val Leu Arg Leu Gly Thr Ala Asn Ser Leu Gly Ile Asn Gln Ser
            260                 265                 270

Ser Ile Arg Gly Thr Tyr Arg Leu Ser Asn Leu Leu Gln Glu Leu Thr
            275                 280                 285

Ile Ala Ser Arg Phe Gly Arg His Gln Ile Val Leu Asp Glu Ala Arg
            290                 295                 300

Leu Ser Glu Asn Pro Val Asp Arg Met Lys Arg Leu Ile Ser Thr Ser
305                 310                 315                 320

Phe Trp Asn Asn Leu Thr Arg Ile Ile Thr Lys Glu Asn Ile Val Asp
                    325                 330                 335

Met Ala Lys Asp Thr Lys Ile Lys Glu Ser Trp Ile Asp Gln Gly
                340                 345                 350

Lys Leu His Glu Asn Gln Glu Ser His Arg Ile Tyr Val Pro Tyr Asn
            355                 360                 365

Arg Lys Asp Gln Tyr Glu Phe Phe Gln Leu Ile Lys Lys Gln Arg Ser
            370                 375                 380

Asp Ile Gln Leu Asp Val Gln Tyr Leu Pro Gln Lys Ile Asp Ala Asp
385                 390                 395                 400

Tyr Ile Lys Ser Ile Asn Lys Lys Pro Gly Leu Leu Ser Ile Ala Thr
                    405                 410                 415

Arg Pro Asp Pro Gln Ala Pro Asp Ser Gly Ser Leu Ile Ser Trp Pro
                420                 425                 430

Tyr Val Val Pro Gly Gly Arg Phe Asn Glu Leu Tyr Gly Trp Asp Ser
            435                 440                 445

Tyr Met Glu Thr Leu Gly Leu Leu Thr Asp Val Lys Ile Asp Pro Ser
            450                 455                 460

Gly Asn Pro Arg Asn Leu Arg His Leu Glu Leu Ala Arg Gly Met Ala
465                 470                 475                 480

Glu Asn Phe Ile Tyr Glu Ile His His Tyr Gly Lys Ile Leu Asn Ala
                    485                 490                 495

Asn Arg Ser Tyr Tyr Leu Gly Arg Ser Gln Pro Pro Phe Leu Thr Asp
                500                 505                 510

Met Ala Leu Arg Ile Phe Asn Lys Thr Ile Glu Val Thr Pro Glu Leu
            515                 520                 525

Met Asp Glu Ala Ile Asp Phe Leu Lys Arg Ala Thr Leu Ala Ala Ile
530                 535                 540

Lys Glu Tyr Glu Thr Ile Trp Cys Ala His Pro Arg Leu Asp Asp Lys
545                 550                 555                 560

Thr Gly Leu Ser Cys Tyr His Pro Glu Gly Lys Gly Ile Pro Pro Glu
                    565                 570                 575

Thr Glu Pro Thr His Phe Asn Ala Leu Leu Lys Pro Tyr Leu Ala Lys
                580                 585                 590

Tyr Asn Asp Ile Asp Gln Leu Asp Phe Ile Glu Lys Tyr Asn Ser Gly
            595                 600                 605

Glu Ile Lys Glu Pro Leu Asp Glu Tyr Phe Leu His Asp Arg Ala
            610                 615                 620

Val Arg Glu Ser Gly His Asp Thr Ser Tyr Arg Leu Glu Gly Lys Cys
625                 630                 635                 640

Ala Tyr Leu Ala Thr Val Asp Leu Asn Ser Leu Leu Tyr Lys Tyr Glu
                    645                 650                 655
```

```
Asn Asp Ile Ala Phe Ile Leu Gln Ser Phe Asn Asp Asn Leu Gln
            660                 665                 670

Asp Pro Tyr Asp Asn Asn Ser Asn Lys Ile His Ser Lys Ile
        675                 680                 685

Trp Leu Glu Arg Ser His Gln Arg Lys Leu Asn Val Asp Lys Tyr Leu
    690                 695                 700

Trp Asn Glu Gln Asp Gly Ile Tyr Tyr Asp Tyr Asn Val Lys Leu Gln
705                 710                 715                 720

Gln Gln Thr Asn Tyr Glu Ser Ala Thr Thr Phe Trp Pro Leu Tyr Ala
                725                 730                 735

Lys Leu Ala Ser Ser Asn Gln Ala Ala Lys Leu Ile Asp Gln Ser Leu
                740                 745                 750

His Lys Phe Glu Glu His Gly Gly Leu Val Ala Gly Thr Leu Lys Ser
            755                 760                 765

Arg Gly Glu Val Gly Leu Thr Arg Pro Ser Arg Gln Trp Asp Tyr Pro
        770                 775                 780

Phe Gly Trp Ala Pro Gln Gln Ile Leu Ala Trp Ile Gly Leu Val Asn
785                 790                 795                 800

Tyr Gly Tyr Asp Gly Ile Ala Arg Arg Leu Ala Tyr Arg Trp Leu Phe
                805                 810                 815

Met Met Thr Lys Ser Phe Val Asp Tyr Asn Gly Val Ile Val Glu Lys
                820                 825                 830

Tyr Asn Val Thr Lys Gly Ala Val Pro His Arg Val Asp Ala Glu Tyr
            835                 840                 845

Gly Asn Gln Gly Leu Asp Phe Lys Gly Val Ala Thr Glu Gly Phe Gly
        850                 855                 860

Trp Val Asn Ala Ser Tyr Val Phe Gly Leu Thr Phe Leu Asn Leu Tyr
865                 870                 875                 880

Ala Gln Arg Ala Leu Gly Ser Leu Thr Pro Pro Glu Ile Phe Leu Arg
                885                 890                 895

Asn Met His Pro Glu Gln Arg Lys Gln Tyr Lys
                900                 905

<210> SEQ ID NO 12
<211> LENGTH: 1100
<212> TYPE: PRT
<213> ORGANISM: Debaryomyces hansenii

<400> SEQUENCE: 12

Met Glu Tyr Asp Ser Ile Gly Glu Arg Phe Lys His Arg Thr Ile Ser
1               5                   10                  15

Lys Ile Asp Tyr Cys Asn Ile Phe Ile His Lys Phe Cys Lys Arg Gln
                20                  25                  30

Ile Val Ile Lys Thr Met Val Val Leu Asn Phe Ile Leu Ile Phe Val
            35                  40                  45

Leu Tyr Ser Tyr Tyr His Gly Ile Thr Tyr Ala Leu Pro Phe Thr Ile
        50                  55                  60

Lys Asp Ile Asp Ile Asp Asp Ser Phe Asn Asp Ser Thr Val Ser Phe
65                  70                  75                  80

Glu Thr Ile Glu Asn Asn Lys Lys Gln Leu Ser Leu Ile Asn Ser
                85                  90                  95

Arg Glu Asn Lys Glu Ile Phe Leu Gln Leu Gln Asn Ser Gly Ser Ala
            100                 105                 110

Tyr Tyr Asp Pro Thr Ser Asn Thr Val Gly Thr Ala Glu Phe Pro Thr
```

```
            115                 120                 125
Tyr Asn Gln Tyr Gln Arg Gln Ala Tyr Val Ser Asn Gly Tyr Ile Gly
130                 135                 140

Ser Arg Ile Pro Asn Leu Gly Gln Gly Phe Thr Phe Asp Gln Leu Ser
145                 150                 155                 160

Asp Ser Pro Asp Ala Val Glu Asp Leu Ser Asn Gly Trp Pro Leu
                165                 170                 175

Phe Asn Glu Arg Phe Ser Gly Ser Phe Ile Gly Gly Phe Tyr Asp Ile
                180                 185                 190

Gln Lys Asn Thr Thr Glu Thr Asn Phe Pro Glu Leu Ile Glu Lys Gly
                195                 200                 205

Tyr Glu Ser Ile Leu Ser Ala Val Pro Gln Trp Thr Thr Leu Thr Leu
210                 215                 220

Ser Thr Val Lys Asn Gly Lys Thr Leu Ser Leu Asp Pro Ser Leu Ser
225                 230                 235                 240

Arg Asp Ser Gln Gly Asp Ile Ser Asn Tyr Ala Gln Asn Leu Ser Leu
                245                 250                 255

Ser Asn Gly Ile Val Thr Thr Glu Phe Thr Trp Leu Glu Ser Ile Gln
                260                 265                 270

Val His Phe Glu Val Ala His Arg Ser Asn Ile Asn Leu Gly Ile
                275                 280                 285

Val Asn Leu Arg Ile Val Asn Leu Asp Asn Ser Thr Val Asp Leu Lys
                290                 295                 300

Val Glu Asp Lys Leu Asp Phe Ala Ser Thr Gln Arg Cys Gln Leu Ser
305                 310                 315                 320

Glu Val Gly Ser Asp Glu Gly Ile Phe Ile His Phe Gln Pro Asn
                325                 330                 335

Glu Ile Asp Tyr Val Asn Gly Ala Ile Tyr Ser Thr Leu Gln Tyr Asp
                340                 345                 350

Glu Met Ser Ser Asn Ala Ile Ser Arg Gly Ser Thr Asn Asp Thr Ser
                355                 360                 365

Thr Gln Lys Leu Asp Ile Ser Val Glu Pro Ser Lys Ser Phe Lys Ile
370                 375                 380

Ser Lys Leu Val Gly Ile Val Ser Ser Asp Leu Asp Pro Glu Lys Tyr
385                 390                 395                 400

Lys Ser His Asn Thr Val Asn Asp Phe Ala Lys Glu Val Ala Thr Lys
                405                 410                 415

Gln Lys Asp Ser Val Ser Lys Leu Ile Lys Ser His Lys Val Gly Trp
                420                 425                 430

Ala Arg Thr Phe Glu Ser Ser Asn Ser Ile Thr Phe Ser Gly Asp Pro
                435                 440                 445

Leu Leu Thr Leu Ala Ser Arg Ala Ser Ile Tyr His Leu Asn Ala Asn
                450                 455                 460

Thr Arg Pro Gly Ala Gln Gly Val Thr Ala Ala Leu Pro Val Gly Gly
465                 470                 475                 480

Leu Ser Ser Asp Ser Tyr Gly Gly Met Val Phe Trp Asp Thr Asp Leu
                485                 490                 495

Trp Met Leu Asn Gly Leu Leu Pro Phe Asn Pro Asp His Ala Lys Ser
                500                 505                 510

Ile Val Asn Tyr Arg Ile His Thr His Glu Gln Ala Ile Lys Asn Val
                515                 520                 525

Pro Asn Asn Glu Ser Gly Ala Val Tyr Ser Trp Thr Ser Gly Arg Phe
530                 535                 540
```

-continued

```
Gly Asn Cys Thr Ser Thr Gly Pro Cys Leu Asp Tyr Glu Tyr His Ile
545                 550                 555                 560

Asn Val Ala Val Ala Met Ala Ala Trp Glu Val Tyr Leu Ser Gly Ala
            565                 570                 575

Ala Asp Asp Tyr Leu Asp Ser Val Ala Tyr Pro Leu Ile Asn Asp
            580                 585                 590

Ala Ala Thr Phe Leu Ala Asp Tyr Val Lys Tyr Asn Glu Ser Leu Ala
            595                 600                 605

Gln Tyr Val Ser His Asn Met Thr Asp Pro Asp Glu Tyr Ala Asn His
            610                 615                 620

Val Asp Asn Ala Ala Tyr Thr Asn Ala Gly Ile Ser Leu Leu Met Lys
625                 630                 635                 640

Trp Ala Ile Thr Ile Ser Asn His Leu Gly Lys Pro Val Pro Ser Lys
                645                 650                 655

Tyr Thr Asp Ile Ala Gly Ser Met His Ile Pro Thr Ser Asp Asn His
                660                 665                 670

Asp Asn Ile Thr Leu Glu Tyr Thr Gly Met Asn Ser Ser Val Gly Ile
            675                 680                 685

Lys Gln Ala Asp Val Ile Met Met Thr Tyr Pro Leu Gly Asn Glu Leu
690                 695                 700

Ile Ser Asp Asp Gln Ala Tyr Thr Asn Met Glu Phe Tyr Ser Met Lys
705                 710                 715                 720

Gln Val Ser Tyr Gly Pro Ala Met Thr Phe Pro Ile Phe Ser Ile Val
                725                 730                 735

Ala Ser Asn Leu Ser Pro Ser Gly Cys Ala Ser Gln Ser Tyr Leu His
                740                 745                 750

Lys Ala Val Gln Pro Phe Leu Arg Gly Pro Phe Ala Gln Phe Ser Glu
                755                 760                 765

Gln Asn Asn Asp Asn Phe Leu Thr Asn Gly Gly Thr His Pro Ala Phe
                770                 775                 780

Pro Phe Met Thr Ala His Gly Gly Phe Leu Gln Ala Ile Leu Gln Gly
785                 790                 795                 800

Leu Thr Gly Leu Arg Phe Asp Phe Asp Leu Asp Asp Arg Asn Lys Leu
                805                 810                 815

Ser Arg Met Leu Thr Leu Asp Pro Ile Ser Leu Pro Cys Leu Gly Asn
                820                 825                 830

Gly Val Gln Phe Asp Ser Ile Lys Tyr Met Asn Gln Ser Ile Ser Leu
                835                 840                 845

Ala Ile Asn Glu Thr Ser Phe Ile Ile Lys His Asn Gly Pro Ile Ala
                850                 855                 860

Gly Gly Asp Ser Asp Ser Ile Arg Ile Ser Leu Ala Lys Arg Asn Pro
865                 870                 875                 880

Lys Ser Gly Val Tyr Thr Leu Asp Lys Gly Glu Leu Val Phe Pro
                885                 890                 895

Leu Phe Val Pro Thr Ala Gly Ser Gln Leu Ser Val Ser Glu Cys Ala
                900                 905                 910

Ser Ala Lys Phe Ile Asn Ile Thr Glu Ser Ala Tyr Gly Asp Ala Thr
                915                 920                 925

Val Ser Val Asn Asp Gly Asp Asn Thr Thr His Trp Gln Ser Lys Tyr
                930                 935                 940

Asn Asp Thr Thr Ala Lys Ile Leu Val Asp Leu Lys Gln Ser Arg Asn
945                 950                 955                 960
```

```
Leu Thr Ser Gly Ala Ile Asn Trp Gly Asp Arg Pro Lys Ser Trp
            965                 970                 975

Ser Leu Ser Ala Phe Gly Ser Glu Glu Gln Ser Lys Ile Asn Asp Leu
            980                 985                 990

Asn Asp Val Ile Asp Phe Leu Ser Lys Val Asn Phe Gly Asn Asp Leu
            995                 1000                1005

Tyr Lys Lys Tyr Gln Phe Ile Asp Ala Gly Thr Ile Tyr Asp Gln
            1010                1015                1020

Asp Asp Val Phe Thr Thr Ile Val Ser Glu Glu Val Asp Ile Ser
            1025                1030                1035

Ala Pro Phe Asp Pro Lys Asp Tyr Ala Glu Val Lys Ile Pro Ser
            1040                1045                1050

Arg His Asn Thr Thr Ser Phe Asn Ile Glu Gln Gly Leu Gly Ala
            1055                1060                1065

Arg Phe Leu Leu Ile Glu Val Thr Asp Ile His Asp Thr Glu Pro
            1070                1075                1080

Ile Asp Asp Glu Thr Gly Gly Ala Lys Leu Tyr Glu Val Glu Phe
            1085                1090                1095

Phe Glu
    1100

<210> SEQ ID NO 13
<211> LENGTH: 1212
<212> TYPE: PRT
<213> ORGANISM: Candida glabrata

<400> SEQUENCE: 13

Met Gly Phe Lys Asp Lys Ile Leu Phe Trp Lys Asp Glu Val Gln Tyr
1               5                   10                  15

Arg Thr Leu Ala Val Ala Asp Gln Val Ala Asn Arg Phe Leu His Ser
                20                  25                  30

Phe Glu Asn Val Tyr Gln Gly Asp Glu Ser Val Glu Asp Ala Asp Ser
            35                  40                  45

Arg Pro Val Gly Leu Thr Asn Glu Thr Leu Ser His Ser Ser Asp Phe
        50                  55                  60

Phe Val Leu Pro Glu Glu Arg Ile Ser Thr Arg Val Lys Ile Arg Arg
65                  70                  75                  80

Gln Asn Ile Leu Asn Thr Thr Leu Ile Leu Gly Met Leu Ile Ala Leu
                85                  90                  95

Val Ile Trp Thr Ala Ile Leu Ser Thr Asn Ser Tyr Phe Ser Ser Ser
                100                 105                 110

Leu Ala Ser Ala Ser Pro Leu Phe Asn Lys Glu Gly Arg Val Val Arg
            115                 120                 125

Pro Met Arg Glu Ser Asn Leu Gly Leu His Ala Asp Pro Gln Thr Arg
        130                 135                 140

Lys Ser Ser Lys Thr Leu Tyr Asp Leu Leu Ser Asp Phe Asp Asn Ala
145                 150                 155                 160

Phe Tyr Asp Asp Glu Asn Met Ile Leu Gly Ser Leu Ala Phe Gly Glu
                165                 170                 175

Asn Thr Tyr Ser Arg Gln Pro Tyr Val Ala Asn Gly Tyr Ile Gly Ser
            180                 185                 190

Arg Ile Pro Asn Ile Gly Phe Gly Tyr Ala Leu Asp Thr Leu Asn Leu
        195                 200                 205

Tyr Ala Asp Ala Pro Gly Ala Leu Asn Asn Gly Trp Pro Leu Arg Asn
    210                 215                 220
```

```
Arg Arg Phe Ala Gly Ser Phe Val Ser Asp Phe Tyr Ser Leu Gln Ala
225                 230                 235                 240

Lys Leu Asn Ser Thr Asn Phe Pro Glu Leu Asp Glu Lys Gly Tyr Thr
            245                 250                 255

Thr Val Ile Ser Ser Ile Pro Glu Trp Thr Asp Leu Gln Phe Thr Val
                260                 265                 270

Asp Leu Asn Gly Thr Lys Trp Phe Asn Pro Gln Ser Val Leu Ile Asp
        275                 280                 285

Asp Val Ile Asn Tyr Asn Gln Asn Leu Ser Met Lys Asp Gly Ile Val
        290                 295                 300

Ser Thr Asn Met Asp Trp Leu Asn Gly Met Ile Asn Ile Lys Ser Glu
305                 310                 315                 320

Val Trp Ala His Arg Lys Ile His Ser Leu Gly Ile Thr Arg Leu Glu
                325                 330                 335

Ile Ser Leu Asn Leu Asp Ala Leu Pro Asp Glu Phe Thr Glu Leu Pro
            340                 345                 350

Val Thr Val Tyr Asp Ile Ile Asp Leu Asn Thr Ser His Arg Thr Thr
        355                 360                 365

Leu Tyr Glu Lys Gly Gln Asp Glu Asp Asn Lys Ala Ile Tyr Met Ile
370                 375                 380

Val Asn Pro Asp Asn Val Pro Tyr Ser Asn Ala Val Val Tyr Ser Thr
385                 390                 395                 400

Cys Thr Ile Lys Gly Thr Glu Asn Asn Phe Ser Pro Tyr Asn Phe Thr
                405                 410                 415

Ser Asp Asp Arg Ile Ala Arg Asn Tyr Met Thr Asn Leu Thr Glu Glu
            420                 425                 430

Asn Pro Lys Val Val Ile Tyr Lys Tyr Thr Ser Val Val Ser Ser Glu
        435                 440                 445

Tyr Asn Asn Asp Glu Pro Asn Pro Asn Val Asn Leu Lys Phe Ala Ser
        450                 455                 460

Asn Ile Ala Asn Thr Ala Lys Gly Asn Tyr Lys Ser Leu Leu Ser Asn
465                 470                 475                 480

His Lys Arg Ala Trp Tyr Asp Leu Tyr Asn Asp Ala Phe Ile Glu Ile
                485                 490                 495

Pro Ser Asp Ser Leu Leu Glu Met Thr Ala Arg Ser Ser Leu Phe His
            500                 505                 510

Leu Leu Ala Asn Thr Arg Gln Tyr Asn Val Ser Thr Thr Arg Gly Leu
        515                 520                 525

Pro Val Gly Val Gly Gly Leu Ser Ser Asp Ser Tyr Gly Gly Met Val
        530                 535                 540

Phe Trp Asp Ala Asp Val Trp Met Ala Pro Ala Leu Leu Pro Phe Phe
545                 550                 555                 560

Pro Asn Ile Ala Met Asn Met Asn Asn Tyr Arg Asn Ala Thr His Gln
                565                 570                 575

Gln Ala Ile Glu Asn Ala Lys Gln Tyr Asn Tyr Pro Gly Ala Val Tyr
            580                 585                 590

Pro Trp Thr Ser Gly Arg Tyr Ala Asn Cys Thr Ser Thr Gly Pro Cys
        595                 600                 605

Ile Asp Tyr Glu Tyr His Ile Asn Val Asp Ile Ala Leu Ala Ser Phe
        610                 615                 620

Ser Ile Tyr Met Asn Gly Ala Glu Gly Ala Asp Glu Asp Tyr Leu Arg
625                 630                 635                 640
```

-continued

Phe Thr Thr Trp Pro Met Val Lys Asp Ala Val Phe Lys Ala
            645             650             655
Tyr Val Lys Tyr Asn Glu Thr Leu Gly Glu Tyr Glu Tyr Asn Leu
        660             665             670
Thr Asp Pro Asp Glu Phe Ala Asn His Val Asn Asn Gly Ala Phe Thr
            675             680             685
Asn Ala Gly Ile Lys Thr Leu Leu Lys Trp Ala Thr Asp Ile Gly Thr
    690             695             700
His Leu Gly Glu Glu Val Asp Pro Lys Trp Met Glu Ile Ala Asp Asn
705             710             715             720
Ile His Ile Pro Arg Ser Asp Ser Asn Ile Thr Leu Glu Tyr Ser Gly
            725             730             735
Met Asn Ser Ser Val Glu Ile Lys Gln Ala Asp Val Thr Leu Met Val
            740             745             750
Tyr Pro Leu Gly Tyr Ile Asn Asp Glu Ser Ile Leu Asn Asn Ala Ile
            755             760             765
Lys Asp Leu Tyr Tyr Ser Glu Arg Gln Ser Ala Ser Gly Pro Ala
    770             775             780
Met Thr Tyr Pro Val Phe Val Ala Ala Ala Ser Leu Leu Asn His
785             790             795             800
Gly Ser Ser Ser Gln Ser Tyr Leu Tyr Lys Ser Val Leu Pro Tyr Leu
            805             810             815
Arg Ser Pro Phe Ala Gln Phe Ser Gln Ser Asp Asp Asn Phe Leu
            820             825             830
Thr Asn Gly Leu Thr Gln Pro Ala Phe Pro Phe Leu Thr Ala Asn Gly
            835             840             845
Gly Phe Leu Gln Ser Ile Leu Phe Gly Leu Thr Gly Leu Arg Tyr Ser
    850             855             860
Tyr Glu Val Thr Pro Arg Thr Lys Lys Ile Ser Arg Leu Leu Lys Phe
865             870             875             880
Asp Pro Val Lys Leu Pro Leu Leu Pro Gly Gly Ile Ala Ile Arg Asn
            885             890             895
Phe Lys Tyr Met Gly Gln Val Leu Asp Ile Ile Ile Asp Asn Asn
            900             905             910
Gly Thr Ile Ala His Lys Gly Gly Asp Lys Pro Ile Arg Ile Lys Val
    915             920             925
Pro Asn Arg Asp Ile Leu His Asp Arg Asn Ile Thr Ser Ala Leu Tyr
            930             935             940
Ser Lys Arg Asp Asp Leu Ser Ala Thr Asp Tyr Tyr Gly Thr
945             950             955             960
Tyr Phe Thr Leu Tyr Pro Asn Glu Glu Leu Val Ile Pro Leu Tyr Asp
            965             970             975
Thr Lys Leu Asn Ile Asp Gly Asn Ile Ala Glu Ser Lys Gln Ile Thr
            980             985             990
Asn Leu Thr Ala Gly Val Pro Gly Asp Val Gly Phe Ser Ala Leu Asp
            995             1000            1005
Gly Asn Asn Tyr Thr His Trp Gln Pro Phe Asp Lys Ser Asp Asn
        1010            1015            1020
Ala Lys Leu Leu Ile Asp Leu Gly Phe Asn Ser Thr His Val Ile
        1025            1030            1035
Lys Lys Gly Ile Ile Leu Trp Gly Gln Arg Pro Ala Lys Asn Ile
        1040            1045            1050
Ser Leu Ser Val Leu Pro His Ser Glu Arg Ile Glu Gln Leu Phe

```
                    1055                    1060                    1065

Ala  Asn  Ile  Thr  Asp  Leu  Leu  Glu  Thr  Ser  Ser  Ile  Thr  Lys  Gly
               1070                    1075                    1080

Gly  Leu  Pro  Leu  Asn  Gln  Met  Leu  Gly  Gln  Thr  Gln  Ser  Asn  Val
          1085                    1090                    1095

Thr  Ala  Glu  Ile  Asp  Asp  Asp  Ile  Leu  Ala  Leu  Leu  Asn  Trp  Lys
     1100                    1105                    1110

Gly  Asp  Asp  Leu  Asp  Gln  Leu  Ile  Pro  Tyr  Leu  Pro  Asp  Met  His
1115                    1120                    1125

Leu  Leu  Gln  Glu  Lys  Phe  Ile  Pro  Ile  Leu  Lys  Asp  Tyr  Pro  Ile
     1130                    1135                    1140

Lys  Pro  Asn  Gln  Arg  Tyr  Tyr  Glu  Ile  Ile  Asp  Asp  Asp  Ile
          1145                    1150                    1155

Ile  Lys  Leu  Leu  Pro  Ser  Asn  Thr  Thr  Glu  Phe  Thr  Ile  Asp  Tyr
     1160                    1165                    1170

Asn  Ser  Ile  Pro  Gly  Gly  Glu  Lys  Arg  Ala  Arg  Tyr  Val  Val  Leu
          1175                    1180                    1185

Thr  Val  His  Gly  Thr  Tyr  Asp  Asp  Asp  Asp  Leu  Lys  Gly  Ala
     1190                    1195                    1200

Thr  Ile  Arg  Glu  Ile  Val  Leu  Gln  Glu
     1205                    1210

<210> SEQ ID NO 14
<211> LENGTH: 754
<212> TYPE: PRT
<213> ORGANISM: Kluyveromyces lactis

<400> SEQUENCE: 14

Met  Asp  Gly  Lys  Val  Asn  Asn  Asn  Pro  Pro  Arg  Ser  Arg  His  Arg  Arg
1                   5                       10                      15

Thr  Ser  Ser  Leu  Glu  Glu  Val  Val  Asp  Pro  Phe  Ser  Thr  Pro  Asp  Val
               20                      25                      30

Tyr  Tyr  Gly  Pro  Lys  Ser  Asp  Pro  Ser  Lys  Leu  Leu  Ser  Lys  Asn  Arg
          35                      40                      45

Phe  Thr  Arg  Thr  Arg  Thr  Phe  Ser  Val  Ala  Glu  Pro  Gly  Gly  Gly  Lys
     50                      55                      60

Gly  His  Ser  Ser  Tyr  Thr  Ser  Pro  Tyr  Phe  Asp  Thr  Thr  Val  Pro
65                      70                      75                      80

Leu  Arg  Arg  Arg  Gly  Ser  Glu  Asp  Asp  Ser  Tyr  Ser  Ala  Ser  Gln  Gly
               85                      90                      95

Gln  Arg  Arg  Phe  Tyr  Ile  Glu  Asp  Val  Asp  Lys  Thr  Leu  Lys  Glu  Leu
          100                     105                     110

Leu  Ala  Ser  Glu  Asp  Thr  Asp  Gly  Asn  Tyr  Gln  Ile  Thr  Ile  Glu  Asp
          115                     120                     125

Thr  Gly  Pro  Lys  Val  Ile  Arg  Val  Gly  Thr  Val  Asn  Ser  Asn  Gly  Tyr
     130                     135                     140

Lys  His  Val  His  Ile  Arg  Gly  Thr  Tyr  Met  Leu  Ser  Asn  Leu  Leu  Gln
145                     150                     155                     160

Glu  Leu  Thr  Leu  Ala  Lys  Leu  Phe  Asn  Arg  Lys  Gln  Val  Ile  Leu  Asp
               165                     170                     175

Glu  Ala  Arg  Leu  Asn  Glu  Asn  Pro  Val  Asn  Arg  Met  Thr  Arg  Leu  Ile
          180                     185                     190

Ser  Gly  Gln  Phe  Trp  Lys  Ser  Leu  Thr  Arg  Arg  Ile  Asp  Ser  Asn  Asn
          195                     200                     205
```

```
Ile Ala Lys Ile Ala Tyr Asp Thr Lys Ile Asp Thr Pro Lys Ala Lys
            210                 215                 220

Asn Pro Arg Ile Tyr Val Pro Tyr Asn Cys Gln Asp Glu Tyr Gln Gln
225                 230                 235                 240

Leu Val Gln Trp Ser Glu Met Asp Pro Ser Leu Gln Leu Glu Val Asn
                245                 250                 255

Tyr Leu Pro Lys Asp Ile Thr Pro Glu Phe Val Lys Ser Leu Asn Asp
            260                 265                 270

Lys Pro Gly Leu Leu Cys Leu Ala Met Glu Ser His Met Asp Pro Val
            275                 280                 285

Thr Gly Glu Glu Thr Trp Val Gly Phe Pro Tyr Ala Val Pro Gly Gly
290                 295                 300

Arg Phe Asn Glu Leu Tyr Gly Trp Asp Ser Tyr Phe Met Ala Leu Gly
305                 310                 315                 320

Leu Leu Glu Ser Asn Lys Leu Asp Val Ala Arg Gly Met Val Glu His
                325                 330                 335

Phe Ile Phe Glu Ile Asp His Tyr Gly Lys Ile Leu Asn Ala Asn Arg
            340                 345                 350

Ser Tyr Tyr Leu Cys Arg Ser Gln Pro Pro Phe Leu Thr Asp Met Ala
            355                 360                 365

Leu Gln Val Cys Arg Lys Met Gly Gly Asp Lys Asn Pro Val Ala Val
370                 375                 380

Asp Leu Leu Arg Arg Ala Phe Lys Ala Ala Ile Lys Glu Tyr Leu Thr
385                 390                 395                 400

Val Trp Thr Ala Ser Pro Arg Leu Asp Glu Lys Thr Gly Leu Ser Cys
                405                 410                 415

Tyr His Pro Asp Gly Ile Gly Ile Pro Pro Glu Thr Glu Pro Gly His
            420                 425                 430

Phe Asp Ser Ile Leu Arg Lys Tyr Ala Glu Lys Tyr Asn Val Ser Ile
            435                 440                 445

Pro Glu Phe Arg Asp Leu Tyr Asn Ser Gln Lys Val His Glu Pro Asp
            450                 455                 460

Leu Asp Val Phe Phe Leu His Asp Arg Gly Val Arg Glu Ser Gly His
465                 470                 475                 480

Asp Thr Thr Tyr Arg Phe Glu Asn Val Cys Ala Tyr Leu Ala Thr Ile
                485                 490                 495

Asp Leu Asn Ser Leu Leu Tyr Lys Tyr Glu Val Asp Ile Ala Tyr Val
            500                 505                 510

Ile Lys Lys Tyr Phe Gly Asp Asn Phe Glu Gly Leu Pro Glu Gly His
            515                 520                 525

Arg Thr Ser Asn Asp Trp Glu Lys Leu Ala Glu Val Arg Lys Glu Arg
530                 535                 540

Ile Asp Lys Tyr Leu Trp Asp Glu Glu Thr Gly Phe Tyr Tyr Asp Tyr
545                 550                 555                 560

Asn Val Lys Thr Glu Lys Arg Thr Ser Tyr Glu Ser Val Thr Thr Phe
                565                 570                 575

Trp Ala Leu Trp Ala Gly Met Ser Ser Gln Glu Gln Ala Gln Arg Met
            580                 585                 590

Val Glu Asn Ala Leu Pro Lys Leu Glu Glu Phe Gly Gly Leu Val Ala
            595                 600                 605

Cys Thr Ala Arg Ser Arg Gly Glu Leu Ser Leu Asp Arg Pro Thr Arg
610                 615                 620

Gln Trp Asp Tyr Pro Phe Gly Trp Ala Pro His Gln Ile Leu Val Trp
```

```
                625                 630                 635                 640
Asp Gly Leu Val Arg Tyr Gly Tyr Glu Asn His Thr Arg Arg Leu Ala
                    645                 650                 655

Tyr Arg Trp Leu Phe Leu Met Thr Lys Ala Phe Val Asp Tyr Asn Gly
            660                 665                 670

Ile Val Val Glu Lys Tyr Asp Val Thr Arg Gly Thr Asp Pro His Arg
                675                 680                 685

Val Asp Ala Glu Tyr Gly Asn Gln Gly Ala Asp Phe Lys Gly Val Ala
            690                 695                 700

Thr Glu Gly Phe Gly Trp Val Asn Ser Ser Tyr Leu Leu Gly Met Lys
705                 710                 715                 720

Tyr Met Asn Asn Phe Ala Arg Arg Ala Leu Gly Thr Cys Val Thr Pro
                725                 730                 735

Lys Val Phe Phe Gly Arg Leu Pro Pro Lys Glu Lys Lys Lys Tyr Gly
                740                 745                 750

Leu Glu

<210> SEQ ID NO 15
<211> LENGTH: 1066
<212> TYPE: PRT
<213> ORGANISM: Rasamsonia emersonii

<400> SEQUENCE: 15

Met Gln Ser Lys Leu Leu Ser Leu Leu Leu Ser Leu Pro Ala Ser
1               5                   10                  15

Cys Leu Pro Leu Glu Glu Arg Val Ala Gln Val Val Arg Ala Tyr Ser
                20                  25                  30

Ser Pro His Gly Leu Gln Val Arg Asp Gly Lys Pro Ala Asn Ala Ser
            35                  40                  45

Gln Thr Tyr Glu Thr Arg Phe Pro Gly Val Thr Trp Asp Gln His Asn
    50                  55                  60

Trp Arg Leu Thr Ser Thr Val Leu Asp Gln Gly His Tyr Gln Ser Arg
65                  70                  75                  80

Gly Ser Ile Ala Asn Gly Tyr Val Gly Ile Asn Val Ala Ser Ala Gly
                85                  90                  95

Pro Phe Phe Glu Leu Asp Thr Pro Val Gly Gly Asp Val Ile Asn Gly
                100                 105                 110

Trp Pro Leu Phe Ser Arg Arg Gln Thr Phe Ala Thr Ile Ala Gly Phe
            115                 120                 125

Tyr Asp Glu Gln Pro Arg Thr Asn Gly Thr Asn Phe Pro Trp Leu Tyr
    130                 135                 140

Gln Tyr Gly Gly Glu Ser Val Ile Ser Gly Val Pro His Trp Ser Gly
145                 150                 155                 160

Leu Val Leu Asp Leu Gly Asp Gly Thr Tyr Leu Asp Ala Thr Val Asp
                165                 170                 175

Asn Thr Thr Ile Ser Asp Tyr Ser Thr Val Tyr Asp Tyr Lys Ala Gly
                180                 185                 190

Ile Leu Ser Trp Ser Tyr Thr Trp Thr Pro Thr Gly Asn Lys Gly Ser
            195                 200                 205

Phe Lys Ile Asn Tyr Ser Leu Phe Ala His Lys Leu Tyr Val Asn Gln
    210                 215                 220

Ala Val Val Arg Leu Asp Ile Thr Pro Ser Thr Asn Thr Asn Ala Thr
225                 230                 235                 240

Val Val Asn Val Ile Asp Gly Tyr Ser Ala Val Pro Thr Asp Phe Val
```

```
            245                 250                 255
Gly Ser Gly Lys Asp Gly Ser Ile Tyr Ser Ala Val Arg Pro Trp Gly
            260                 265                 270
Ile Asn Asn Val Thr Ala Tyr Ile Tyr Thr Val Leu Asp Gly Ser Asn
            275                 280                 285
Gly Val Asp Leu Ser Ser Ala Ala Ile Val Ser Asn Lys Pro Tyr Ile
            290                 295                 300
His Thr Asn Asp Ser Ser Ile Ala Gln Ser Val Asn Val Gly Phe Arg
305                 310                 315                 320
Ser Gly Lys Thr Val Ser Ile Thr Lys Leu Val Gly Ala Ala Ser Ser
                325                 330                 335
Asp Ala Phe Pro Asn Pro Gln Gln Thr Ala Lys Glu Ala Ala Leu Thr
                340                 345                 350
Ala Lys Lys Lys Gly Tyr Glu Ala Leu Leu Arg Ser His Val Lys Glu
                355                 360                 365
Trp Ala Ala Val Met Pro Asp Asp Ser Val Asp Asp Phe Thr Phe Pro
            370                 375                 380
Glu Asn Gly Thr Leu Pro Gln Asp Pro Phe Ile Ile Glu Ser Ala Ile
385                 390                 395                 400
Thr Ala Val Val Asn Pro Tyr Tyr Leu Leu Gln Asn Thr Val Ser Glu
                    405                 410                 415
Asn Ala Leu Lys Glu Ile Ser Asn Ala Pro Ala Asn Glu Trp Ser Ile
                420                 425                 430
Ser Val Gly Gly Leu Thr Ser Asp Ser Tyr Pro Gly Phe His Phe Leu
                435                 440                 445
Gly Arg Gln Ile Cys Gly Met His Leu Gly Leu Val Val Phe Ser Pro
            450                 455                 460
Lys Gln Pro Arg Gly Ile Pro Gln Ile Thr Gly Lys Pro Ser Thr Ser
465                 470                 475                 480
Lys Pro Ala Lys Thr Leu Arg Leu Ala Phe Thr Ser Ser Lys Asn Lys
                485                 490                 495
Thr Trp Phe Ser Asp Ser Ala Ala Val Tyr Pro Trp Thr Ser Gly Arg
                500                 505                 510
Tyr Gly Asn Cys Thr Gly Thr Gly Pro Cys Trp Asp Tyr Glu Tyr His
                515                 520                 525
Leu Asn Gly Asp Ile Gly Leu Ser Leu Ile Asn Gln Trp Val Thr Ser
            530                 535                 540
Gly Asp Thr Lys Thr Phe Gln Glu Ser Tyr Phe Pro Ile Tyr Asp Ser
545                 550                 555                 560
Ile Ala Thr Leu Tyr Ala Asp Leu Leu Arg Leu Asn Gly Ser His Trp
                565                 570                 575
Thr Leu Thr Asn Met Thr Asp Pro Asp Glu Tyr Ala Asn Pro Val Asn
            580                 585                 590
Ala Gly Gly Tyr Thr Met Leu Leu Ile Ala Gln Thr Leu Phe Tyr Ala
            595                 600                 605
Asn Ser Phe Arg Gln Gln Phe Gly Ile Ala Lys Asn Thr Thr Trp Thr
            610                 615                 620
Asp Met Ala Ser Asn Ile Leu Leu Arg Glu Asn Asp Val Thr Leu
625                 630                 635                 640
Glu Tyr Thr Thr Met Asn Asn Ser Val Ala Val Lys Gln Ala Asp Val
                    645                 650                 655
Val Leu Val Thr Tyr Pro Leu Asp Tyr Ser Thr Asn Tyr Ser Ser Ser
                660                 665                 670
```

```
Asp Ala Leu Asn Asp Leu Asp Tyr Tyr Ala Leu Lys Gln Ser Pro Asp
            675                 680                 685

Gly Pro Gly Met Thr Tyr Ala Ile Phe Ser Ile Val Ala Asn Glu Val
690                 695                 700

Ser Pro Ser Gly Cys Ser Val Tyr Thr Tyr Ala Gln Tyr Ser Tyr Asp
705                 710                 715                 720

Pro Tyr Val Arg Ala Pro Phe Phe Gln Phe Ser Glu Gln Leu Ile Asp
                725                 730                 735

Asp Tyr Thr Leu Asn Gly Gly Thr His Pro Ala Tyr Pro Phe Leu Thr
            740                 745                 750

Gly His Gly Gly Ala Asn Gln Val Val Ile Phe Gly Tyr Leu Gly Leu
            755                 760                 765

Arg Leu Leu Pro Asp Asp Ala Ile His Ile Asp Pro Asn Leu Pro Pro
770                 775                 780

Gln Val Pro His Val Lys Tyr Arg Thr Phe Tyr Trp Arg Gly Trp Pro
785                 790                 795                 800

Ile Gln Ala Ser Ser Asn Tyr Thr His Phe Thr Ile Ser Arg Ala Ala
                805                 810                 815

His Val Gln Pro Leu Asp Thr Ala Asp Gln Arg Phe Ala Lys Thr Ala
            820                 825                 830

Ile Pro Val Gln Val Gly Ser Gly Lys Asn Val Thr Val Tyr Gln Leu
            835                 840                 845

Pro Leu Lys Gly Gln Leu Thr Val Pro Asn His Gln Val Gly Ser Thr
850                 855                 860

Leu Thr Val Pro Gly Asn Leu Ala Gln Cys Gln Pro Val Gln Ser Gln
865                 870                 875                 880

Asn Ser Tyr Glu Pro Gly Gln Tyr Pro Met Ala Ala Val Asp Gly Ala
                885                 890                 895

Ala Ser Thr Lys Trp Gln Pro Ser Phe Ala Ala Asn Thr Ser Ser Leu
            900                 905                 910

Thr Val Ser Leu Pro Ala Ser Glu Ser Gly Ala Met Val Ser Gly Phe
            915                 920                 925

Tyr Phe Asp Trp Ala Gln Ala Pro Pro Val Lys Ala Thr Val Val Phe
930                 935                 940

His Asn Asp Thr Ser Asp Asp Pro Leu Ala Thr Ser Ser Asn Gly Gln
945                 950                 955                 960

Ser Leu Ser Arg Ile Leu Ala Thr Leu Pro Phe Leu Val Leu Thr Thr
                965                 970                 975

Pro Glu Ala Thr Arg Ala Asp Thr Ile Met Phe Arg Gly Gly Asn Thr
            980                 985                 990

Thr Asn Val Thr Leu Ala Gln Pro Val Pro Gly Ala Thr Val Arg His
            995                 1000                1005

Phe Cys Ile Ser Pro Ala Ile Lys Arg Ser Ala Ser Gln Val Arg
    1010                1015                1020

Pro Arg Thr Ala Arg Ala Arg Arg Leu Gln Ser Gly Arg Phe Trp
    1025                1030                1035

Arg Thr Thr Leu Arg Ser Asn Ser Arg Ser Glu Arg Phe Arg Trp
    1040                1045                1050

Ser Val Ser Ser Pro Ala Leu Ala Gly Leu His Ala Arg
    1055                1060                1065

<210> SEQ ID NO 16
<211> LENGTH: 738
```

```
<212> TYPE: PRT
<213> ORGANISM: Ashbya gossypii

<400> SEQUENCE: 16
```

| | | | | | | | | | | | | | | |
|---|---|---|---|---|---|---|---|---|---|---|---|---|---|---|
|Met|Leu|Gln|Gly|Met|Pro|Lys|Arg|Ser|Gly|Ser|Ile|Ser|Glu|Leu|His|
|1| | | |5| | | | |10| | | | |15| |

| | | | | | | | | | | | | |
|---|---|---|---|---|---|---|---|---|---|---|---|---|
|Asp|Pro|Phe|Ser|Ser|Pro|Asp|Val|Tyr|Tyr|Gly|Pro|Ala|Thr|Asp|Pro|
| | | |20| | | | |25| | | | |30| | |

Arg Arg Gln Lys Gln Pro Asn Lys Tyr Ser Arg Thr Arg Thr Met Ser
            35                  40                  45

Ile Ile Glu Asn Val Ser Thr Phe Lys Ser Ala Gly Lys Gln Tyr Asn
 50                  55                  60

Ile Arg Arg Arg Gly Ser Glu Asp Asp Ser Met Leu Ala Ser Ser Gly
 65                  70                  75                  80

His Arg Lys Phe Tyr Ile Lys Asp Val Asp Lys Thr Leu Glu Glu Leu
                85                  90                  95

Leu Glu Ser Glu Asp Thr Asp Gly Asn Tyr Gln Ile Thr Ile Glu Asp
               100                 105                 110

Arg Gly Pro Lys Thr Leu Arg Val Gly Thr Ala Asn Ser Asn Gly Phe
               115                 120                 125

Arg His Val Gln Ile Arg Gly Thr Tyr Met Leu Ser Asn Leu Leu Gln
               130                 135                 140

Glu Leu Thr Ile Ala Lys Asn Phe Gly Arg Lys Gln Val Ile Leu Asp
145                 150                 155                 160

Glu Ala Arg Leu Asn Glu Asp Pro Val Asn Arg Leu Thr Arg Leu Ile
                165                 170                 175

Thr His Gln Phe Trp Asp Ser Leu Thr Arg Arg Ile Asp Tyr Asn Ser
                180                 185                 190

Ile Ala Ala Ile Ala Ala Asp Thr Lys Val Asp Thr Pro Gly Ala Lys
                195                 200                 205

Val Pro Arg Ile Tyr Val Pro His Gly Cys Pro Glu Gln Tyr Glu Tyr
                210                 215                 220

Phe Ile Glu Cys Ser Gln Leu Asn Pro Ser Leu Asn Leu Glu Val Lys
225                 230                 235                 240

Tyr Leu Pro Asp Val Ile Thr Pro Glu His Val Gln Ser Leu Asn Glu
                245                 250                 255

Ser Pro Gly Leu Leu Ala Leu Ala Met Glu Ser His Arg Asp Pro Ile
                260                 265                 270

Thr Gly Glu Ser Thr Leu Val Gly Phe Pro Tyr Val Val Pro Gly Gly
                275                 280                 285

Arg Phe Asn Glu Leu Tyr Gly Trp Asp Ser Tyr Leu Met Ala Leu Gly
                290                 295                 300

Leu Leu Asp Cys Asn Lys Val Asp Ile Ala Arg Gly Met Val Glu His
305                 310                 315                 320

Phe Ile Phe Glu Ile Glu His Tyr Gly Lys Ile Leu Asn Ala Asn Arg
                325                 330                 335

Ser Tyr Tyr Leu Cys Arg Ser Gln Pro Pro Phe Leu Thr Asp Met Ala
                340                 345                 350

Leu Lys Val Phe Glu Lys Phe Gly Gly Asp Gln Asn Pro Thr Ala Val
                355                 360                 365

Asp Phe Leu Lys Arg Ala Phe Ile Ala Ala Ile Lys Glu Tyr Lys Ser
                370                 375                 380

Val Trp Met Ala Glu Pro Arg Tyr Asp Lys Thr Thr Gly Leu Ser Cys
385                 390                 395                 400

```
Tyr His Pro Asp Gly Ile Gly Phe Pro Pro Glu Thr Glu Pro Asp His
            405                 410                 415

Phe Asp Ala Ile Cys Arg Lys Phe Ala Glu Lys His Asn Val Thr Ile
            420                 425                 430

Pro Glu Phe Arg Cys Met Tyr Asp Ala Gly Glu Val His Glu Pro Glu
            435                 440                 445

Leu Asp Glu Phe Phe Leu His Asp Arg Ala Val Arg Glu Ser Gly His
            450                 455                 460

Asp Thr Ser Tyr Arg Leu Glu Asn Val Cys Ala Tyr Leu Ala Thr Ile
465                 470                 475                 480

Asp Leu Asn Ser Leu Leu Tyr Lys Tyr Glu Lys Asp Ile Ala Tyr Val
            485                 490                 495

Val Ser Lys Tyr Phe Asp Asp Ser Ile Thr Asp Tyr Ala Gly Glu Thr
            500                 505                 510

Thr Thr Ser Ser His Trp Glu Ala Leu Ala Asp Ile Arg Lys Gln Arg
            515                 520                 525

Ile Thr Lys Tyr Leu Trp Asp Glu Glu Thr Gly Phe Phe Tyr Asp Tyr
            530                 535                 540

Asn Val His Ile Gly Lys Arg Thr Ser Tyr Asp Ser Ala Thr Thr Phe
545                 550                 555                 560

Trp Ala Met Trp Ala Gly Leu Ala Thr Gln Glu Gln Ala Asn Ala Met
            565                 570                 575

Val Glu Lys Ala Leu Pro Arg Leu Glu Met Leu Gly Gly Leu Val Ala
            580                 585                 590

Cys Thr Glu Glu Ser Arg Gly Glu Ile Thr Met Asn Arg Pro Ser Arg
            595                 600                 605

Gln Trp Asp Tyr Pro Tyr Gly Trp Ala Pro His Gln Met Leu Ala Trp
            610                 615                 620

Thr Gly Leu Asp Asn Tyr Gly Phe Thr Gly Val Ala Arg Arg Leu Ala
625                 630                 635                 640

Tyr Arg Trp Leu Phe Leu Met Thr Lys Ala Phe Val Asp Tyr Asn Gly
            645                 650                 655

Ile Val Val Glu Lys Tyr Asp Val Thr Arg Gly Thr Asp Pro His Arg
            660                 665                 670

Val Asp Ala Glu Tyr Gly Asn Gln Gly Ala Asp Phe Lys Gly Val Ala
            675                 680                 685

Thr Glu Gly Phe Gly Trp Val Asn Ser Ser Tyr Ile Leu Gly Leu Lys
            690                 695                 700

Phe Met Asn Thr Tyr Ala Lys Arg Ala Leu Ala Asn Cys Thr Val Pro
705                 710                 715                 720

Asp Ile Phe Phe Lys His Met Lys Pro Glu Glu Lys Ala Arg Tyr Ala
            725                 730                 735

Leu Ile

<210> SEQ ID NO 17
<211> LENGTH: 698
<212> TYPE: PRT
<213> ORGANISM: Magnaporthe oryzae

<400> SEQUENCE: 17

Met Ser Pro Leu Trp Lys Thr Ala Ala Ile Ala Val Ala Ala Ser
1               5                   10                  15

Gly Ser Leu Val Asn Ala Val Tyr Ile Asn Gly Ser Ile Ile Thr Pro
            20                  25                  30
```

```
Cys Asp Ser Leu Ile Tyr Cys Arg Gly Glu Leu Leu Lys Glu Val Glu
         35                  40                  45

Leu Ala His Pro Phe Ala Asp Ser Lys Thr Phe Val Asp Met Pro Thr
 50                  55                  60

Ile Lys Pro Val Asp Glu Val Ile Glu Ala Phe Asn Lys Leu Gln Lys
 65                  70                  75                  80

Pro Leu Ser Asn Asn Thr Glu Leu Gln Asp Phe Leu Arg Glu Asn Phe
                 85                  90                  95

Ala Gln Ala Gly Gly Glu Leu Glu Glu Val Pro Asn Ser Glu Leu Glu
                100                 105                 110

Thr Asp Pro Val Phe Leu Asp Lys Leu Asp Asp Thr Val Ile Arg Glu
            115                 120                 125

Phe Val Glu Lys Val Ile Asp Ile Trp Pro Ser Leu Thr Arg Arg Tyr
        130                 135                 140

Lys Gly Pro Ser Asn Cys Glu Ala Cys Ala Asp Ser Phe Ile Pro Val
145                 150                 155                 160

Asn Arg Thr Phe Val Val Ala Gly Gly Arg Phe Arg Glu Pro Tyr Tyr
                165                 170                 175

Trp Asp Ser Tyr Trp Ile Leu Glu Gly Leu Leu Arg Thr Gly Gly Ala
            180                 185                 190

Phe Thr Asn Ile Ser Lys Asn Thr Val Glu Asn Phe Leu Asp Leu Val
        195                 200                 205

Glu Thr Ile Gly Phe Val Pro Asn Gly Ala Arg Ile Tyr Tyr Lys Asn
    210                 215                 220

Arg Ser Gln Pro Pro Leu Leu Ser Gln Met Val Arg Ile Tyr Val Glu
225                 230                 235                 240

His Thr Asn Asp Thr Ser Ile Leu Gly Arg Ala Val Pro Leu Leu Ile
                245                 250                 255

Lys Glu His Glu Phe Phe Ile Asn Asn Arg Ser Ile Asp Val Glu Ala
            260                 265                 270

Ser Asn Gly Lys Thr Tyr Arg Leu Gln Arg Tyr Ala Val Thr Asn Thr
        275                 280                 285

Gln Pro Arg Pro Glu Ser Tyr Arg Glu Asp Tyr Ile Thr Ala Ser Asn
    290                 295                 300

Arg Ser Tyr Tyr Ser Pro Ser Gly Ile Ile Tyr Pro Glu Ser His Gln
305                 310                 315                 320

Leu Asn Glu Ser Glu Lys Ala Val Leu Tyr Ser His Leu Ala Ser Gly
                325                 330                 335

Ala Glu Ser Gly Trp Asp Tyr Thr Ser Arg Trp Leu Ser Thr Pro Ser
            340                 345                 350

Asp Ala Val Arg Asp Asn Tyr Phe Pro Leu Arg Ser Leu Asn Thr Asn
        355                 360                 365

Asn Ile Val Pro Val Asp Leu Asn Ser Ile Leu Tyr Ala Asn Glu Val
    370                 375                 380

Ala Ile Ala Glu Phe Leu Asn Arg Thr Gly Asn Ser Thr Gly Ala Ser
385                 390                 395                 400

Asp Trp Met Asp Leu Ala Lys Gln Arg Ser Glu Ala Met Tyr Ala Leu
                405                 410                 415

Met Trp Asn Glu Thr Leu Trp Ser Tyr Phe Asp Tyr Asn Met Thr Ser
            420                 425                 430

Lys Thr Gln Asn Arg Phe Ile Pro Val Asp Glu Asp Ala Val Ser Ile
        435                 440                 445
```

```
Glu Thr Asn Asn Ala Pro Ala Gly Gln Gln Val Phe Phe His Val Ala
    450                 455                 460

Gln Tyr Tyr Pro Phe Trp Thr Gly Ala Ala Pro Arg Ser Leu Lys Asn
465                 470                 475                 480

Asn Pro Leu Ala Val Leu Arg Ala Tyr Glu Arg Ile Asp Ala Tyr Leu
                485                 490                 495

Asp Ile Lys Arg Gly Ala Ile Pro Ala Thr Asn Leu Lys Thr Gly Gln
            500                 505                 510

Gln Trp Asp Glu Pro Asn Val Trp Pro Leu Met His Ile Leu Met
        515                 520                 525

Glu Gly Leu Thr Arg Val Pro Ala Thr Phe Gly Glu Asp Val Ala
    530                 535                 540

Trp Thr Glu Ile Gln Asp Leu Ala Leu Arg Leu Gly Gln Arg Tyr Leu
545                 550                 555                 560

Asp Ser Thr Phe Cys Thr Trp Tyr Ala Thr Gly Gly Ser Thr Ser Glu
                565                 570                 575

Thr Pro Gln Leu Gln Gly Leu Asn Ala Glu Asp Lys Gly Ile Met Phe
            580                 585                 590

Glu Lys Tyr Gly Asp Asn Ser Thr Asn Val Ala Gly Ser Gly Gly Glu
        595                 600                 605

Tyr Glu Val Val Glu Gly Phe Gly Trp Thr Asn Gly Val Leu Met Trp
    610                 615                 620

Val Ala Asp Thr Phe Asn Asn Lys Leu Thr Arg Pro Asp Cys Gly Asn
625                 630                 635                 640

Ile Thr Ala Ala Asn Val His Ser Asp Gly Ser Gln Ala Arg Lys Arg
                645                 650                 655

Gly Glu Met Trp Ser Ala Leu Glu Met His Pro Tyr Asp Ala Ala Trp
            660                 665                 670

Thr Lys Glu Phe Gly Ala Arg Lys Val Arg Arg Asp Lys Ala Glu Ala
        675                 680                 685

Arg Ala Leu Gly Asn Val Met Gly Gly Val
    690                 695

<210> SEQ ID NO 18
<211> LENGTH: 528
<212> TYPE: PRT
<213> ORGANISM: Thermus thermophiles

<400> SEQUENCE: 18

Met Trp Trp Lys Glu Ala Val Ile Tyr Gln Val Tyr Pro Arg Ser Phe
1               5                   10                  15

Gln Asp Thr Asn Gly Asp Gly Val Gly Asp Leu Glu Gly Val Arg Arg
                20                  25                  30

Arg Leu Pro Tyr Leu Lys Ser Leu Gly Val Asp Ala Leu Trp Leu Ser
            35                  40                  45

Pro Phe Tyr Lys Ser Pro Met Lys Asp Phe Gly Tyr Asp Val Ala Asp
        50                  55                  60

Tyr Cys Asp Val Asp Pro Val Phe Gly Thr Leu Gln Asp Phe Asp Arg
65                  70                  75                  80

Leu Leu Glu Glu Ala His Ala Leu Gly Leu Lys Val Leu Val Asp Leu
                85                  90                  95

Val Pro Asn His Thr Ser Ser Glu His Pro Trp Phe Leu Glu Ser Arg
            100                 105                 110

Ala Ser Arg Asn Ser Pro Lys Arg Asp Trp Tyr Ile Trp Lys Asp Pro
        115                 120                 125
```

Ala Pro Asp Gly Gly Pro Pro Asn Asn Trp Gln Ser Phe Gly Gly
130                 135                 140

Pro Ala Trp Thr Leu Asp Glu Ala Thr Gly Gln Tyr Tyr Leu His Gln
145                 150                 155                 160

Phe Leu Pro Glu Gln Pro Asp Leu Asn Trp Arg Asn Pro Glu Val Arg
                165                 170                 175

Glu Ala Ile Tyr Glu Val Met Arg Phe Trp Leu Arg Arg Gly Val Asp
            180                 185                 190

Gly Phe Arg Val Asp Val Leu Trp Leu Leu Ala Glu Asp Leu Leu Phe
        195                 200                 205

Arg Asp Glu Pro Gly Asn Pro Asp Trp Arg Pro Gly Met Trp Asp Arg
210                 215                 220

Gly Arg His Leu His Ile Phe Thr Glu Asp Gln Pro Glu Thr Tyr Ala
225                 230                 235                 240

Tyr Val Arg Glu Met Arg Gln Val Leu Asp Glu Phe Ser Glu Pro Gly
                245                 250                 255

Arg Glu Arg Val Met Val Gly Glu Ile Tyr Leu Pro Tyr Pro Gln Leu
            260                 265                 270

Val Arg Tyr Tyr Gln Ala Gly Cys His Leu Pro Phe Asn Phe His Leu
        275                 280                 285

Ile Phe Arg Gly Leu Pro Asp Trp Arg Pro Glu Asn Leu Ala Arg Ile
290                 295                 300

Val Glu Glu Tyr Glu Ser Leu Leu Thr Arg Trp Asp Trp Pro Asn Trp
305                 310                 315                 320

Val Leu Gly Asn His Asp Gln Pro Arg Leu Ala Ser Arg Leu Gly Glu
                325                 330                 335

Ala Gln Ala Arg Val Ala Ala Met Leu Leu Phe Thr Leu Arg Gly Thr
            340                 345                 350

Pro Thr Trp Tyr Tyr Gly Asp Glu Ile Gly Met Lys Asn Gly Glu Ile
        355                 360                 365

Pro Pro Glu Lys Val Gln Asp Pro Ala Ala Leu Arg Gln Lys Asp Arg
370                 375                 380

Leu Gly Glu His Asn Leu Pro Pro Gly Arg Asp Pro Glu Arg Thr Pro
385                 390                 395                 400

Met Gln Trp Asp Asp Thr Pro Phe Ala Gly Phe Ser Thr Val Glu Pro
                405                 410                 415

Trp Leu Pro Val Asn Pro Asp Tyr Lys Thr Arg Asn Val Ala Ala Gln
            420                 425                 430

Glu Gln Asp Pro Arg Ser Met Leu His Leu Val Arg Leu Ile Ala
        435                 440                 445

Leu Arg Lys Asp Pro Asp Leu Leu Tyr Gly Ala Tyr Arg Thr Tyr Arg
450                 455                 460

Ala Arg Glu Gly Val Tyr Ala Tyr Leu Arg Gly Glu Gly Trp Leu Val
465                 470                 475                 480

Ala Leu Asn Leu Thr Glu Lys Glu Lys Ala Leu Glu Leu Pro Arg Gly
                485                 490                 495

Gly Arg Val Val Leu Ser Thr His Leu Asp Arg Glu Glu Arg Val Gly
            500                 505                 510

Glu Arg Leu Phe Leu Arg Pro Asp Glu Gly Val Ala Val Arg Leu Asp
        515                 520                 525

<210> SEQ ID NO 19
<211> LENGTH: 36

```
<212> TYPE: DNA
<213> ORGANISM: Artificial Sequence
<220> FEATURE:
<223> OTHER INFORMATION: Primer Oligonucleotide

<400> SEQUENCE: 19
gcagaggatt acttggacat taacggttct cctatc                                    36

<210> SEQ ID NO 20
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 20
ggacgaggca agctaaacag atctctagac ctaagttcta tgtcttaata agtctgtatg          60

<210> SEQ ID NO 21
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 21
tactcacata cagacttatt aagacataga acttaggtct agagatctgt ttagcttgcc          60

<210> SEQ ID NO 22
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 22
gaatagacga tcgtctcatt tgcatcgggt tcagagacta catgatagtc caaagaaaag          60

<210> SEQ ID NO 23
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 23
ccgtttcttt tctttggact atcatgtagt ctctgaaccc gatgcaaatg agacgatcgt          60

<210> SEQ ID NO 24
<211> LENGTH: 36
<212> TYPE: DNA
<213> ORGANISM: Artificial Sequence
<220> FEATURE:
<223> OTHER INFORMATION: Primer Oligonucleotide

<400> SEQUENCE: 24
gcaagaggct cctccactgg cattttcacg atttgg                                    36

<210> SEQ ID NO 25
<211> LENGTH: 35
<212> TYPE: DNA
<213> ORGANISM: Artificial Sequence
<220> FEATURE:
<223> OTHER INFORMATION: Primer Oligonucleotide

<400> SEQUENCE: 25
```

```
gctgtgcagc agggtattct actacgtgtt agctt                         35
```

\<210\> SEQ ID NO 26
\<211\> LENGTH: 60
\<212\> TYPE: DNA
\<213\> ORGANISM: Artificial Sequence
\<220\> FEATURE:
\<223\> OTHER INFORMATION: Primer Oligonucleotide

\<400\> SEQUENCE: 26

```
ggacgaggca agctaaacag atctctagac ctattcggca cagaaatagt gacaggcagt   60
```

\<210\> SEQ ID NO 27
\<211\> LENGTH: 60
\<212\> TYPE: DNA
\<213\> ORGANISM: Artificial Sequence
\<220\> FEATURE:
\<223\> OTHER INFORMATION: Primer Oligonucleotide

\<400\> SEQUENCE: 27

```
aataacactg cctgtcacta tttctgtgcc gataggtct agagatctgt ttagcttgcc    60
```

\<210\> SEQ ID NO 28
\<211\> LENGTH: 60
\<212\> TYPE: DNA
\<213\> ORGANISM: Artificial Sequence
\<220\> FEATURE:
\<223\> OTHER INFORMATION: Primer Oligonucleotide

\<400\> SEQUENCE: 28

```
tctagtcata accatttcgt taaaagggt gttgagacta catgatagtc caaagaaaag    60
```

\<210\> SEQ ID NO 29
\<211\> LENGTH: 60
\<212\> TYPE: DNA
\<213\> ORGANISM: Artificial Sequence
\<220\> FEATURE:
\<223\> OTHER INFORMATION: Primer Oligonucleotide

\<400\> SEQUENCE: 29

```
ccgtttcttt tctttggact atcatgtagt ctcaacaccc ttttaacga aatggttatg    60
```

\<210\> SEQ ID NO 30
\<211\> LENGTH: 31
\<212\> TYPE: DNA
\<213\> ORGANISM: Artificial Sequence
\<220\> FEATURE:
\<223\> OTHER INFORMATION: Primer Oligonucleotide

\<400\> SEQUENCE: 30

```
cgtagatcga ccttgcctgg aatcccaggt t                              31
```

\<210\> SEQ ID NO 31
\<211\> LENGTH: 32
\<212\> TYPE: DNA
\<213\> ORGANISM: Artificial Sequence
\<220\> FEATURE:
\<223\> OTHER INFORMATION: Primer Oligonucleotide

\<400\> SEQUENCE: 31

```
ctcgttggta gggtccacac catagacttc ag                             32
```

\<210\> SEQ ID NO 32
\<211\> LENGTH: 35
\<212\> TYPE: DNA
\<213\> ORGANISM: Artificial Sequence

```
<220> FEATURE:
<223> OTHER INFORMATION: Primer Oligonucleotide

<400> SEQUENCE: 32
tagctatgaa atttttaact ctttaagctg gctct                                35

<210> SEQ ID NO 33
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 33
gatgagagcc agcttaaaga gttaaaaatt tcatagctag ggcgccataa ccaaggtatc     60

<210> SEQ ID NO 34
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 34
ccaacaaaga aacccaagta gccaagtttt gagacaacat gtttagttaa ttatagttcg     60

<210> SEQ ID NO 35
<211> LENGTH: 54
<212> TYPE: DNA
<213> ORGANISM: Artificial Sequence
<220> FEATURE:
<223> OTHER INFORMATION: Primer Oligonucleotide

<400> SEQUENCE: 35
gaatatacgg tcaacgaact ataattaact aaacatgttg tctcaaaact tggc           54

<210> SEQ ID NO 36
<211> LENGTH: 58
<212> TYPE: DNA
<213> ORGANISM: Artificial Sequence
<220> FEATURE:
<223> OTHER INFORMATION: Primer Oligonucleotide

<400> SEQUENCE: 36
caaagacttt cataaaaagt ttgggtgcgt aacacgctat caagcgttga attgtctg       58

<210> SEQ ID NO 37
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 37
gctttgaacg acagaagata cagacaattc aacgcttgat agcgtgttac gcacccaaac    60

<210> SEQ ID NO 38
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 38
tatataaaat taaatacgta aatacagcgt gctgcgtgct atgaggaaga aatccaaatc    60
```

<210> SEQ ID NO 39
<211> LENGTH: 35
<212> TYPE: DNA
<213> ORGANISM: Artificial Sequence
<220> FEATURE:
<223> OTHER INFORMATION: Primer Oligonucleotide

<400> SEQUENCE: 39
agcacgcagc acgctgtatt tacgtattta atttt                    35

<210> SEQ ID NO 40
<211> LENGTH: 35
<212> TYPE: DNA
<213> ORGANISM: Artificial Sequence
<220> FEATURE:
<223> OTHER INFORMATION: Primer Oligonucleotide

<400> SEQUENCE: 40
gtagtgctgt ctgaacagaa taaatgcgtt cttgg                    35

<210> SEQ ID NO 41
<211> LENGTH: 30
<212> TYPE: DNA
<213> ORGANISM: Artificial Sequence
<220> FEATURE:
<223> OTHER INFORMATION: Primer Oligonucleotide

<400> SEQUENCE: 41
ctgactcgtt ggtggggtcc acaccataga                          30

<210> SEQ ID NO 42
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 42
gattggcggt ctatagatac cttggttatg gcgccctagc tatgaaattt ttaactcttc    60

<210> SEQ ID NO 43
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 43
gagagccagc tttttgaaga gttaaaaatt tcatagctag ggcgccataa ccaaggtatc    60

<210> SEQ ID NO 44
<211> LENGTH: 20
<212> TYPE: DNA
<213> ORGANISM: Artificial Sequence
<220> FEATURE:
<223> OTHER INFORMATION: Primer Oligonucleotide

<400> SEQUENCE: 44
gtttagttaa ttatagttcg                                     20

<210> SEQ ID NO 45
<211> LENGTH: 60
<212> TYPE: DNA
<213> ORGANISM: Artificial Sequence
<220> FEATURE:
<223> OTHER INFORMATION: PrimerOligonucleotide

```
<400> SEQUENCE: 45
tttttagaat atacggtcaa cgaactataa ttaactaaac atgagattca agtccgtttt        60

<210> SEQ ID NO 46
<211> LENGTH: 60
<212> TYPE: DNA
<213> ORGANISM: Artificial Sequence
<220> FEATURE:
<223> OTHER INFORMATION: PrimerOligonucleotide

<400> SEQUENCE: 46
aatgaaaaaa aaagtggtag attgggctac gtaaattcga ttacaacaaa ggaactggtt        60

<210> SEQ ID NO 47
<211> LENGTH: 21
<212> TYPE: DNA
<213> ORGANISM: Artificial Sequence
<220> FEATURE:
<223> OTHER INFORMATION: Primer Oligonucleotide

<400> SEQUENCE: 47
tcgaatttac gtagcccaat c                                                 21

<210> SEQ ID NO 48
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 48
tatataaaat taaatacgta aatacagcgt gctgcgtgct caaatgacgt caaaagaagt        60

<210> SEQ ID NO 49
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 49
cataggctca tataatactt cttttgacgt catttgagca cgcagcacgc tgtatttacg        60

<210> SEQ ID NO 50
<211> LENGTH: 32
<212> TYPE: DNA
<213> ORGANISM: Artificial Sequence
<220> FEATURE:
<223> OTHER INFORMATION: Primer Oligonucleotide

<400> SEQUENCE: 50
gtagtgctgt ctgaacagaa taaatgcgtt ct                                     32

<210> SEQ ID NO 51
<211> LENGTH: 33
<212> TYPE: DNA
<213> ORGANISM: Artificial Sequence
<220> FEATURE:
<223> OTHER INFORMATION: Primer Oligonucleotide

<400> SEQUENCE: 51
cacctacaga gaaacaaatt cctactggca ccc                                    33

<210> SEQ ID NO 52
```

<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 52
ttggcggtct atagatacct tggttatggc gcccgtcgac aactaaactg gaatgtgagg    60

<210> SEQ ID NO 53
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 53
acttttgttg ttccctcaca ttccagtttta gttgtcgacg ggcgccataa ccaaggtatc    60

<210> SEQ ID NO 54
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 54
ccaacaaaga aacccaagta gccaagtttt gagacaacat gtttagttaa ttatagttcg    60

<210> SEQ ID NO 55
<211> LENGTH: 59
<212> TYPE: DNA
<213> ORGANISM: Artificial Sequence
<220> FEATURE:
<223> OTHER INFORMATION: Primer Oligonucleotide

<400> SEQUENCE: 55
gaatatacgg tcaacgaact ataattaact aaacatgttg tctcaaaact tggctactt     59

<210> SEQ ID NO 56
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 56
aaatgaaaaa aaaagtggta gattgggcta cgtaaattcg atcaagcgtt gaattgtctg    60

<210> SEQ ID NO 57
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 57
gctttgaacg acagaagata cagacaattc aacgcttgat cgaatttacg tagcccaatc    60

<210> SEQ ID NO 58
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 58

```
attttgaggg aagggggaag attgtagtac ttttcgagaa caaatgacgt caaaagaagt    60

<210> SEQ ID NO 59
<211> LENGTH: 60
<212> TYPE: DNA
<213> ORGANISM: Artificial Sequence
<220> FEATURE:
<223> OTHER INFORMATION: Primer Oligonucleotide

<400> SEQUENCE: 59
taggctcata taatacttct tttgacgtca tttgttctcg aaaagtacta caatcttccc    60

<210> SEQ ID NO 60
<211> LENGTH: 44
<212> TYPE: DNA
<213> ORGANISM: Artificial Sequence
<220> FEATURE:
<223> OTHER INFORMATION: Primer Oligonucleotide

<400> SEQUENCE: 60
gaacttctgc ctttgaacaa tttcccaaac aattttcatt ggtc                     44
```

US 11,634,734 B2

LIMITING YEAST-PRODUCED TREHALOSE IN FERMENTATION

CROSS-REFERENCE TO RELATED APPLICATIONS AND DOCUMENTS

This application claims priority from U.S. provisional patent application 62/251,885 filed on Nov. 6, 2015. This application is filed concurrently with a sequence listing in an electronic format. The content of the priority application and the sequence listing is herewith incorporated in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 580127_418C3_SEQUENCE_LISTING.txt. The text file is 145 KB, was created on Feb. 8, 2021, and is being submitted electronically via EFS-Web.

TECHNOLOGICAL FIELD

This disclosure relates to the use of recombinant yeast host cells for limiting the production and/or secretion of trehalose during fermentation, such as, for example, an alcoholic fermentation. The use of the recombinant yeast host cells can increase the production of one or more fermentation product, such as, for example, ethanol.

BACKGROUND

*Saccharomyces cerevisiae* is the primary biocatalyst used in the commercial production of fuel ethanol. This organism is proficient in fermenting glucose to ethanol, often to concentrations greater than 20% w/v. However, *S. cerevisiae* lacks the ability to hydrolyze polysaccharides and therefore may require the exogenous addition of enzymes to convert complex sugars to glucose. Several *S. cerevisiae* strains have been genetically engineered to express alpha(α)-amylase and/or glucoamylase (see for example, WO 2011/153516 and WO 2012/138942) and the use of such strains increases the overall yield while representing a substantial cost savings.

One potential for yield improvements is targeting the breakdown of residual fermentable sugars. For example, a typical corn ethanol fermentation will have approximately 4 g/L of residual disaccharide sugars (also referred to as degree of polymerization 2 or DP2), comprised of maltose, isomaltose and the majority being trehalose (Giffen 2012). These disaccharides represent a potential of an additional 4 g/L ethanol.

Trehalose is a non-reducing disaccharide composed of two glucose molecules linked at the 1-carbon, forming an α-α bond. In yeasts, trehalose can act as carbohydrate storage, but more importantly, it has been well characterized to act as a stress protectant against desiccation, high temperatures, ethanol toxicity, and acidic conditions by stabilizing biological membranes and native proteins (Elbein et al. 2003; Singer and Lindquist 1998). Intracellular trehalose is well-regulated in yeast based on an equilibrium between synthesis and degradation. It is obtained by catalyzing the combination of a uridine-diphosphate-glucose moiety to a glucose-6-phosphate to form trehalose-6-phosphate (see FIG. 1). The phosphate group is then removed to form trehalose. The primary pathway is facilitated by a protein complex encoded by four genes: the trehalose-6-phosphate synthase (TPS1 encoded by the tps1 gene), trehalose-6-phosphate phosphatase (TPS2 encoded by the tps2 gene) and two regulatory proteins, TPS3 and TSL1. Trehalose can be catabolized into two glucose molecules by either the cytoplasmic trehalase enzyme, NTH1, or the tethered, extracellular trehalase, ATH1. Under certain conditions, trehalose can also be excreted from the yeast.

The trehalose biosynthetic pathway has also been proposed to be a primary regulator of glycolysis by creating a futile cycle. As glucose is phosphorylated by hexokinase (HXK), the intracellular free organic phosphate levels are quickly depleted which is required for downstream processes and other metabolic processes (see FIG. 1). Conversion of glucose-6-phosphate into trehalose not only removes the sugar from glycolysis, creating a buffer, but the pathway also regenerates inorganic phosphate. Another primary control of glycolysis is the inhibition of HXK2 by trehalose-6-phosphate, thereby further slowing the glycolysis flux.

Numerous manipulations of the trehalose pathway in *S. cerevisiae* have been reported. Attempts at trehalose manipulations as a means of targeting ethanol yield increases have primarily focused on over-expression of the pathway, particularly with TPS1/TPS2 (Cao et al. 2014; Guo et al. 2011; An et al. 2011). Ge et al. (2013) successfully improved ethanol titers on pure glucose with the over-expression of the TSL1 component, which has also been implicated in glucose signaling. Deletion of the biosynthetic pathway has proved more challenging. As reviewed by Thevelein and Hohmann (1995), attempts to remove the TPS1 function have led to the decreased ability to grow on readily fermentable carbon sources due to the aforementioned control of glycolysis. Functional analysis of the TPS complex has been extensively studied using knockout approaches (Bell et al. 1998), but none have targeted deletion of the key biosynthetic genes as a means of improving ethanol yields nor have they targeted relevant fuel ethanol processes.

It would be highly desirable to be provided with methods of using recombinant yeast host cells which are capable of modulating the production and/or the excretion of trehalose and/or trehalose breakdown while being capable of fermenting a medium and producing a fermentation product.

BRIEF SUMMARY

The present disclosure relates to the use of recombinant yeasts capable of limiting the accumulation of trehalose during fermentation in order to increase the production of another fermentation product during fermentation. The recombinant yeast host cells comprises at least two genetic modifications. The first genetic modification allows for reducing the production of one or more native enzymes that function to produce glycerol or regulating glycerol synthesis and/or allowing the production of an heterologous glucoamylase. The second genetic modification allows for reducing the production of one or more native enzymes that function to produce or regulating trehalose synthesis and/or allowing the expression of an heterologous trehalase.

In a first aspect, the present disclosure provides a recombinant yeast host cell comprising: (i) a first genetic modification for reducing the production of one or more native enzymes that function to produce glycerol or regulating glycerol synthesis and/or allowing the production of an heterologous glucoamylase; and (ii) a second genetic modification for reducing the production of one or more native enzymes that function to produce trehalose or regulating trehalose synthesis and/or allowing the expression of an heterologous trehalase. In an embodiment, the recombinant yeast host cell has the second genetic modification allowing the expression of the heterologous trehalase. In an embodiment, the recombinant yeast host cell has the first genetic modification for reducing the production of the one or more native enzymes that function to produce glycerol and the second genetic modification for reducing the production of the one or more native enzymes that function to produce trehalose or regulating trehalose synthesis. In another embodiment, the recombinant yeast host cell has the first modification for reducing the production of the one or more native enzymes that function to produce glycerol or regulating glycerol synthesis and the second modification allowing the production of the heterologous trehalase. In yet another embodiment, the recombinant yeast host cell has the first genetic modification allowing the production of the heterologous glucoamylase and the second genetic modification for reducing the production of the one or more native enzymes that function to produce trehalose or regulating trehalose synthesis. In still another embodiment, the recombinant yeast host cell has the first genetic modification allowing the production of the heterologous glucoamylase and the second genetic modification allowing the production of the heterologous trehalase. In a further embodiment, the recombinant yeast host cell comprises a further (third) genetic modification for reducing the production of the one or more native enzymes that function to catabolize formate. In such embodiment, the recombinant yeast host cell can, for example, lack the ability to produce a FDH1 polypeptide and/or a FDH2 polypeptide. In an embodiment, the recombinant yeast host cell comprises a further (fourth) genetic modification to reduce the production of the one or more native enzymes that function to produce glycerol (e.g., decreases or inhibits in the expression of the a GPD1 polypeptide and/or a GPD2 polypeptide) or regulating glycerol synthesis (e.g., decreases or inhibits the expression of a FPS1 polypeptide and/or increases the expression of a STL1 polypeptide). In another embodiment, the recombinant yeast host cell comprises a further (fifth) genetic modification allowing the expression of heterologous glucoamylase. In an embodiment, the heterologous glucoamylase is from the genus *Saccharomycopsis* sp., such as, for example, from the species *Saccharomycopsis fibuligera*. In yet a further embodiment, the heterologous glucoamylase has or consists of the amino acid sequence of SEQ ID NO: 3, is a variant of the amino acid sequence of SEQ ID NO: 3 or is a fragment of the amino acid sequence of SEQ ID NO: 3. In another embodiment, the second genetic mutation causes a reduction in the expression level or prevents the expression of the one or more native enzymes that function to produce trehalose or regulating trehalose synthesis, such as, for example, the TPS2 polypeptide or a polypeptide encoded by a tps2 ortholog. In a further embodiment, the heterologous trehalase is an acid trehalase. In a further embodiment, the acid trehalase is from the genus *Aspergillus* sp., for example, from the species *Aspergillus fumigatus* or the species *Aspergillus nidulans*. In an embodiment, the acid trehalase has the amino acid sequence of SEQ ID NO: 1, is a variant of the amino acid sequence of SEQ ID NO: 1 or is a fragment of the amino acid sequence of SEQ ID NO: 1. In yet another embodiment, the acid trehalase has the amino acid sequence of SEQ ID NO: 2, is a variant of the amino acid sequence of SEQ ID NO: 2 or is a fragment of the amino acid sequence of SEQ ID NO: 2. In still another embodiment, the recombinant yeast host cell is from the genus *Saccharomyces* sp., such as, for example, from the species *Saccharomyces cerevisiae*.

In a second aspect, the present disclosure provides a method of limiting the accumulation of extracellular trehalose during a fermentation. Broadly, the method comprises fermenting a medium with at least one recombinant yeast host cell described herein. In an embodiment, the method can also include adding an heterologous trehalase to the medium.

In a third aspect, the present disclosure provides a method of increasing the production of a fermentation product during a fermentation, said method comprising fermenting a medium with at least one recombinant yeast host cell described herein. In an embodiment, the method can also include adding an heterologous acid trehalase to the medium. In a further embodiment, the fermentation product is ethanol. In yet another embodiment, the medium comprises starch which can be optionally be provided in a gelatinized or a raw form. In yet another embodiment, the medium can be derived from corn. In another embodiment, the medium comprises maltodextrin.

BRIEF DESCRIPTION OF THE DRAWINGS

Having thus generally described the nature of the invention, reference will now be made to the accompanying drawings, showing by way of illustration, a preferred embodiment thereof, and in which.

DETAILED DESCRIPTION

Figure 1:
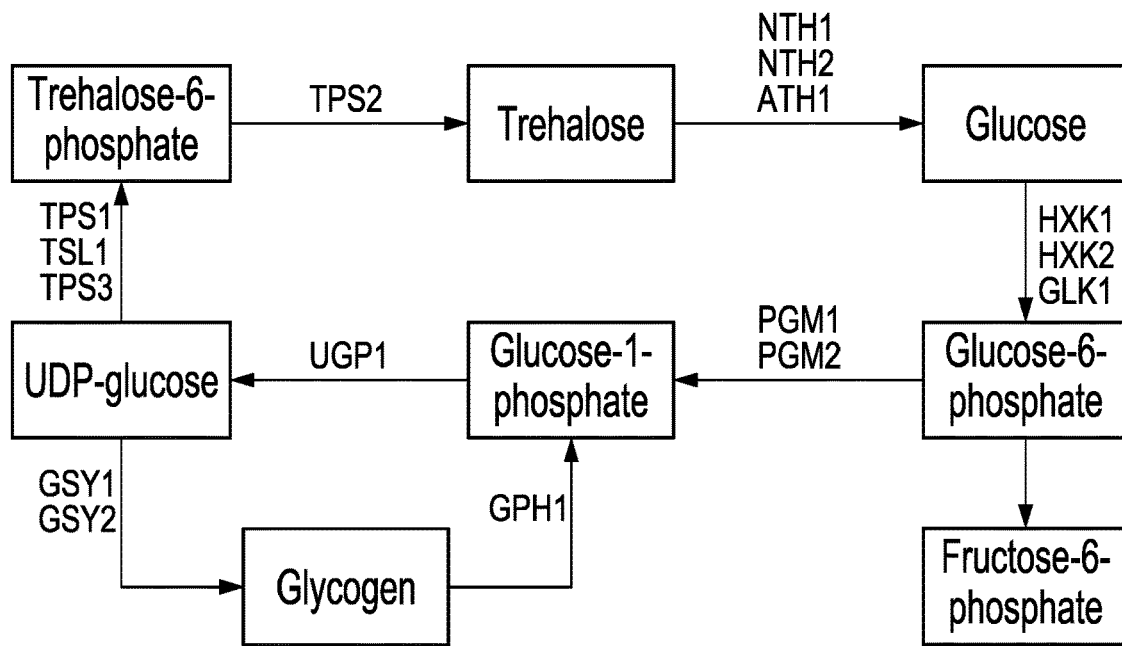
FIG. 1 illustrates the trehalose synthesis pathway. Abbreviations: HXK=hexokinase; GLK=glucokinase; PGM=phosphoglucomutase; UGP1=UDP-glucose pyrophosphorylase; GSY=glycogen synthase; GPH=Glycogen phosphorylase; TPS1=trehalose-6-phosphate synthase; TPS3=trehalose-6-phosphate synthase; TSL1=trehalose synthase long chain; TPS2=trehalose-6-phosphate phosphatase; NTH=neutral trehalase; ATH1=acid trehalase.

The present disclosure relates to the use of recombinant yeast host cells capable of limiting the production, accumulation or excretion of trehalose during fermentation. The recombinant yeast host cell comprising at least two distinct genetic modifications (also referred to as genetic mutations). The genetic modifications are preferably made using genetic engineering techniques. Firstly, the recombinant yeast host cells can be modified to reduce or inhibit the production of one or more native enzymes that function to produce glycerol or regulating glycerol synthesis. Alternatively or in combination, the recombinant yeast host cells can be modified to produce an heterologous glucoamylase. Secondly, the recombinant yeast host cells can be modified to reduce or inhibit the production of one or more native enzymes that function to produce trehalose or regulating trehalose synthesis. Alternatively or in combination, the recombinant yeast host cells can be modified to produce an heterologous trehalase. The use of such recombinant yeast host cells, in some conditions, limits the level of trehalose during fermentation to a maximum of 1.0 g/L.

Recombinant Yeast Host Cells

The present disclosure concerns recombinant yeast host cells that have been genetically engineered to include at least two genetic modifications. The genetic modifications can be made in one or both copies of the targeted gene(s). In the context of the present disclosure, when recombinant yeast cell is qualified as being "genetically engineered", it is understood to mean that it has been manipulated to either add at least one or more heterologous or exogenous nucleic acid residue and/or removed at least one endogenous (or native) nucleic acid residue. The genetic manipulations did not occur in nature and are the results of in vitro manipulations of the yeast.

In the context of the present disclosure, the recombinant host cell is a yeast. Suitable yeast host cells can be, for example, from the genus *Saccharomyces, Kluyveromyces, Arxula, Debaryomyces, Candida, Pichia, Phaffia, Schizosaccharomyces, Hansenula, Kloeckera, Schwanniomyces* or *Yarrowia*. Suitable yeast species can include, for example, *S. cerevisiae, S. bulderi, S. barnetti, S. exiguus, S. uvarum, S. diastaticus, K. lactis, K. marxianus* or *K. fragilis*. In some embodiments, the yeast is selected from the group consisting of *Saccharomyces cerevisiae, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*. In some embodiment, the host cell can be an oleaginous yeast cell. For example, the oleaginous yeast host cell can be from the genus *Blakeslea, Candida, Cryptococcus, Cunninghamella, Lipomyces, Mortierella, Mucor, Phycomyces, Pythium, Rhodosporidum, Rhodotorula, Trichosporon* or *Yarrowia*. In some alternative embodiment, the host cell can be an oleaginous microalgae host cell (e.g., for example, from the genus *Thraustochytrium* or *Schizochytrium*). In an embodiment, the recombinant yeast host cell is from the genus *Saccharomyces* and, in some embodiments, from the species *Saccharomyces cerevisiae*.

The first modification of the recombinant yeast host cell can be a genetic modification leading to the reduction in the production, and in an embodiment to the inhibition in the production, of one or more native enzymes that function to produce glycerol or regulating glycerol synthesis. As used in the context of the present disclosure, the expression "reducing the production of one or more native enzymes that function to produce glycerol or regulating glycerol synthesis" refers to a genetic modification which limits or impedes the expression of genes associated with one or more native polypeptides (in some embodiments enzymes) that function to produce glycerol or regulating glycerol synthesis, when compared to a corresponding yeast strain which does not bear the first genetic modification. In some instances, the first genetic modification reduces but still allows the production of one or more native polypeptides that function to produce glycerol or regulating glycerol synthesis. In other instances, the first genetic modification inhibits the production of one or more native enzymes that function to produce glycerol or regulating glycerol synthesis. In some embodiments, the recombinant yeast host cells bear a plurality of first genetic modifications, wherein at least one reduces the production of one or more native polypeptides and at least another inhibits the production of one or more native polypeptides. As used in the context of the present disclosure, the expression "native polypeptides that function to produce glycerol or regulating glycerol synthesis" refers to polypeptides which are endogenously found in the recombinant yeast host cell. Native enzymes that function to produce glycerol include, but are not limited to, the GPD1 and the GPD2 polypeptide (also referred to as GPD1 and GPD2 respectively). Native enzymes that function to regulating glycerol synthesis include, but are not limited to, the FPS1 polypeptide as well as the STL1 polypeptide. The FPS1 polypeptide is a glycerol exporter and the STL1 polypeptide functions to import glycerol in the recombinant yeast host cell. By either reducing or inhibiting the expression of the FPS1 polypeptide and/or increasing the expression of the STL1 polypeptide, it is possible to control, to some extent, glycerol synthesis. In an embodiment, the recombinant yeast host cell bears a genetic modification in at least one of the gpd1 gene (encoding the GPD1 polypeptide), the gpd2 gene (encoding the GPD2 polypeptide), the fps1 gene (encoding the FPS1 polypeptide) or orthologs thereof. In another embodiment, the recombinant yeast host cell bears a genetic modification in at least two of the gpd1 gene (encoding the GPD1 polypeptide), the gpd2 gene (encoding the GPD2 polypeptide), the fps1 gene (encoding the FPS1 polypeptide) or orthologs thereof. In still another embodiment, the recombinant yeast host cell bears a genetic modification in each of the gpd1 gene (encoding the GPD1 polypeptide), the gpd2 gene (encoding the GPD2 polypeptide) and the fps1 gene (encoding the FPS1 polypeptide) or orthologs thereof. Examples of recombinant yeast host cells bearing such genetic modification(s) leading to the reduction in the production of one or more native enzymes that function to produce glycerol or regulating glycerol synthesis are described in WO 2012/138942. Preferably, the recombinant yeast host cell has a genetic modification (such as a genetic deletion or insertion) only in one enzyme that functions to produce glycerol, in the gpd2 gene, which would cause the host cell to have a knocked-out gpd2 gene. In some embodiments, the recombinant yeast host cell can have a genetic modification in the gpd1 gene, the gpd2 gene and the fps1 gene resulting is a recombinant yeast host cell being knock-out for the gpd1 gene, the gpd2 gene and the fps1 gene. In still another embodiment (in combination or alternative to the "first" genetic modification described above), the recombinant yeast host cell can have a genetic modification in the st1 gene (e.g., a duplication for example) for increasing the expression of the STL1 polypeptide.

The first genetic modification can also allow for the production of an heterologous glucoamylase. Many microbes produce an amylase to degrade extracellular starches. In addition to cleaving the last α(1-4) glycosidic linkages at the non-reducing end of amylose and amylopectin, yielding glucose, γ-amylase will cleave α(1-6) glycosidic linkages. The heterologous glucoamylase can be derived from any organism. In an embodiment, the heterologous protein is derived from a γ-amylase, such as, for example, the glucoamylase of Saccharomycoces filbuligera (e.g., encoded by the glu 0111 gene). Examples of recombinant yeast host cells bearing such first genetic modifications are described in WO 2011/153516.

The heterologous glucoamylase can be a variant of a known glucoamylase, for example a variant of the heterologous glucoamylase having the amino acid sequence of SEQ ID NO: 3. The glucoamylase variants have at least 50%, 55%, 60%, 65%, 70%, 75%, 80%, 85%, 90%, 95%, 96%, 97%, 98% or 99% identity to the glucoamylases described herein. A variant comprises at least one amino acid difference when compared to the amino acid sequence of the native glucoamylase. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5. The variant heterologous glucoamylases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide.

A "variant" of the glucoamylase can be a conservative variant or an allelic variant. As used herein, a conservative variant refers to alterations in the amino acid sequence that do not adversely affect the biological functions of the glucoamylase. A substitution, insertion or deletion is said to adversely affect the protein when the altered sequence prevents or disrupts a biological function associated with the glucoamylase (e.g., the hydrolysis of starch). For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the glucoamylase.

The heterologous glucoamylase can be a fragment of a known glucoamylase or fragment of a variant of a known glucoamylase (such as, for example, a fragment of the glucoamylase having the amino acid sequence of SEQ ID NO: 3). Glucoamylase "fragments" have at least at least 100, 200, 300, 400, 500 or more consecutive amino acids of the glucoamylase. A fragment comprises at least one less amino acid residue when compared to the amino acid sequence of the glucoamylase and still possess the enzymatic activity of the full-length glucoamylase. In some embodiments, fragments of the glucoamylases can be employed for producing the corresponding full-length glucoamylase by peptide synthesis. Therefore, the fragments can be employed as intermediates for producing the full-length proteins.

The heterologous nucleic acid molecule encoding the heterologous glucoamylase, variant or fragment can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

In the context of the present disclosure, the recombinant yeast host cell can include at least two "first" genetic modifications, one in leading to the reduction in the production of one or more native enzymes that function to produce glycerol or regulating glycerol synthesis and another one leading to the expression of an heterologous glucoamylase. It is also contemplated that the recombinant yeast host cell can include a single first genetic modification, either for reducing in the production of one or more native enzymes that function to produce glycerol or regulating glycerol synthesis or for expressing an heterologous glucoamylase.

The second genetic modification of the recombinant yeast host cell can lead to the reduction in the production (or the prevention of expression) of one or more native enzymes that function to produce trehalose or regulating trehalose synthesis. As used in the context of the present disclosure, the expression "reducing the production of one or more native enzymes that function to produce trehalose or regulating trehalose synthesis" refers to a genetic modification which limits or impedes the expression of genes associated with one or more native polypeptides (in some embodiments enzymes) that function to produce trehalose or regulating trehalose synthesis, when compared to a corresponding yeast strain which does not bear the second genetic modification. In some instances, the second genetic modification reduces but still allows the production of one or more native polypeptides that function to produce trehalose or regulating trehalose synthesis. In other instances, the second genetic modification inhibits the production of one or more native enzymes that function to produce trehalose or regulating trehalose synthesis. In some embodiments, the recombinant yeast host cells bear a plurality of second genetic modifications, wherein at least one reduces the production of one or more native polypeptides and at least another inhibits the production of one or more native polypeptides. As used in the context of the present disclosure, the expression "native polypeptides that function to produce trehalose or regulating trehalose synthesis" refers to polypeptides which are endogenously found in the recombinant yeast host cell. Native enzymes that function to produce trehalose include, but are not limited to, the TPS1 and TPS2 (both members of the TPS complex). Native enzymes that function to regulating trehalose synthesis include, but are not limited to polypeptides involved in interacting with the TPS complex such as, for example, TPS3 and TSL1 as well as polypeptides responsible for synthesizing precursors of the TPS complex such as, for example, NTH1, NTH2, ATH1, HXK1, HXK2, GLK1, PGM1, PGM2, GPH1, UGP1, GSY1 and GSY2. In an embodiment, the recombinant yeast host cell bears a genetic modification in at least one, two, three or more of the tps1 gene (encoding the TPS1 polypeptide), the tps2 gene (encoding the TPS2 polypeptide), the tps3 gene (encoding the TPS3 polypeptide), the tsl1 gene (encoding the TSL1 polypeptide), the nth1 gene (encoding the NTH1 polypeptide), the nth2 gene (encoding the NTH2 polypeptide), the ath1 gene (encoding the ATH1 polypeptide), the hxk1 gene (encoding the HXK1 polypeptide), the hxk2 gene (encoding the HXK2 polypeptide), the g/k1 gene (encoding the GLK1 polypeptide), the pgm1 gene (encoding the PGM1 polypeptide), the pgm2 gene (encoding the PGM2 polypeptide), the gph1 gene (encoding the GPH1 polypeptide), the ugp1 gene (encoding the UGP1 polypeptide), the gsy1 gene (encoding the GSY1 polypeptide), the gsy2 gene (encoding the GSY2 polypeptide) or orthologs thereof. Preferably, the recombinant yeast host cell has a genetic modification (such as a genetic deletion or insertion) only in one enzyme that functions to produce glycerol, in the tps2 gene, which would cause the host cell to have a knocked-out tps2 gene.

In some circumstances, the second genetic modification can be made to (or, in some instances, limited to) the tps2 gene or to the tps2 gene ortholog. As such, the recombinant yeast host cell can lack the ability to produce a biologically active trehalose-6-phosphate phosphatase (TPS2 polypeptide). The yeast strain can be genetically engineered to impede or prevent the expression of the tps2 gene or to allow the expression of a non-functional TPS2 polypeptide. In an embodiment, the second genetic modification can be limited to the tps2 gene (or its ortholog), its corresponding transcript or its corresponding polypeptide and are intended to either reduce the expression of the gene, reduce the expression and/or stability of the transcript, reduce the expression and/or stability of the polypeptide or reduce the biological activity of the polypeptide. In one embodiment, the open-reading frame of the tps2 gene (or its ortholog) is disrupted specifically by the introduction of an heterologous nucleic acid molecule. In another embodiment, the open-reading frame of the tps2 gene can be deleted (in part or in total).

In some instances, the recombinant yeast host cell can have the ability to produce trehalose-6-phosphate (for example by producing the TPS1 polypeptide). In the context of the present disclosure, the expression "capable of producing trehalose-6-phosphate" refers to a yeast strain which has the ability of expressing a gene or a combination of genes leading to the production of trehalose-6-phosphate. The trehalose-6-phosphate synthase gene (also referred to the tps1 gene) and the activity of the trehalose-6-phosphate synthase (referred to as the TPS1 polypeptide) are important in the production of trehalose-6-phosphate. As such, a recombinant yeast strain capable of producing trehalose-6-phosphate usually has a tps1 gene and is capable of expressing a functional/biologically active TPS1 polypeptide. As it is known in the art, the TPS1 polypeptide is an enzyme involved in the synthesis of trehalose-6-phosphate from UDP-glucose.

Still in the context of the present disclosure, the expression "lacking the ability to produce a biologically active trehalose-6-phosphate phosphatase (TPS2 polypeptide)" refers to a yeast strain which has been genetically engineered to prevent the expression from the tps2 gene or expresses a non-functional trehalose-6-phosphate phosphatase (TPS2 polypeptide). As known in the art, the tps2 gene encodes an enzyme (TPS2 polypeptide) having the ability to recognize trehalose-6-phosphate and cleave the bound between trehalose and the phosphate group. As such, a biologically active or functional TPS2 polypeptide is capable of recognizing trehalose-6-phosphate and cleave the bound between trehalose and the phosphate group. It follows that a biologically inactive or non-functional TPS2 polypeptide cannot recognize trehalose-6-phosphate and/or cleave the bound between trehalose and the phosphate group.

As indicated above, the recombinant yeast host cell can be genetically engineered to impede or prevent the expression of the tps2 gene (or a tps2 gene ortholog) by manipulating the endogenous coding sequence of the nucleic acid sequence of the tps2 gene (or the tps2 gene ortholog). The tps2 gene (also known as hog2 or pfk3) has been specifically described in Saccharomyces cerevisiae and is associated with the Gene ID 851646. In the context of the present disclosure, a "tps2 gene ortholog" is understood to be a gene in a different species that evolved from a common ancestral gene by speciation. In the context of the present invention, a tps2 ortholog retains the same function, e.g. it encodes for an enzyme capable of dephosphorylating trehalose-6-phosphate.

The TPS2 polypeptide has been specifically described in Saccharomyces cerevisiase under GenBank Accession Number CAA98893.1. In the context of the present disclosure, the tps2 gene (or its ortholog) can encode a TPS2 polypeptide having one of the following GenBank Accession Number XP_009255856.1, CEP23739.1, EKJ75382.1, CAA98893.1, P31688.3 GI:1730010, 014145.1, NP_010359.1, DAA11920.1, CAB16285., NP_594975.1, CAA86796.1, AAF80562.1, CAA50025.1, CDM32404.1, BA038481.1, AJV20879.1, AJV20163.1, AJV19466.1, AJV18745.1, AJV18033.1, AJV17324.1, AJV16619.1, AJV15908.1, AJV15200.1, AJV14492.1, AJV13824.1, AJV13114.1, AJV12465.1, AJV11777.1, AJV11078.1, AJV10431.1, AJV09728.1, AJV09023.1, AJV08338.1, AJV07644.1, AJV06938.1, AJV06235.1, AJV05531.1, AJV04812.1, AJV04100.1, AJV03395.1, AJV02725.1, AJV02019.1, AJV01306.1, AJV00594.1, AJU99880.1, AJU99185.1, AJU98485.1, AJU97772.1, AJU97074.1, AJU96370.1, AJU95666.1, AJU94967.1, AJU94268.1, AJU93563.1, AJU92846.1, AJU92131.1, AJU91414.1, AJU90697.1, AJU89979.1, AJU89269.1, AJU88578.1, AJU87873.1, AJU87202.1, AJU86553.1, AJU85852.1, AJU85155.1, AJU84444.1, AJU83731.1, AJU83018.1, AJU82439.1, AJU81736.1, AJU81046.1, AJU80346.1, AJU79746.1, AJU79035.1, AJU78323.1, AJU77611.1, AJU76901.1, AJU76191.1, AJU75483.1, AJU74777.1, AJU74061.1, AJU73348.1, AJU72635.1, AJU71925.1, AJU71213.1, AJU70526.1, AJU69816.1, AJU69121.1, AJU68429.1, AJU67713.1, AJU66996.1, AJU66318.1, AJU65601.1, AJU64885.1, AJU64173.1, AJU63483.1, AJU62784.1, AJU62085.1, AJU61373.1, AJU60685.1, AJU60022.1, AJU59308.1, AJU58621.1, AJU57919.1, AJP37799.1, AHY75069.1, EGW34937.1, ABN67480.2, XP_007372349.1, EWG97048.1, ACB46526.1, XP_001385509.2, ACY82596.1, ACY82595.1, EEU05123.1, EDN60419.1, DAA05785.1, CAC17748.1, XP_013021409.1, XP_013017766.1, KMK60772.1, EPY53152.1, EPX75323.1 GI:528065761, EEB06603.1, XP_002172896.1, KEY78745.1, EXX70387.1, EXX62686.1, EXX62685.1, EXX62684.1, EXX62683.1, GAA85661.1, XP_755036.1 or CAD24957.1.

Various methods are known to those skilled in the art to impede or prevent the expression of the endogenous tps2 gene or the endogenous tps2 gene ortholog. In the context of the present disclosure, a gene which is "endogenous" to a yeast is understood to mean that such gene is natively provided in the organism. For example, a gene encoding a TPS2 polypeptide having phosphatase activity is considered endogenous to yeast has been natively produced by such yeast and is not the result of an in vitro genetic modification. As an another example, a gene is considered to be endogenous to a yeast is considered to have been natively included in or produced by such yeast and was not deliberately introduced by genetic means in the yeast.

In order to impede or prevent the expression of the tps2 gene or its ortholog, the recombinant yeast strain can be genetically engineered to disrupt the open-reading frame of the endogenous tps2 gene or its ortholog by inserting a non-coding sequence or adding one or more nucleic acid residues from the open-reading frame. In such instance, while a section of the tps2 gene or of the tps2 gene ortholog could be expressed (for example, the section of the gene which precedes the insertion or addition) but a functional TPS2 polypeptide could not be produced (due to the presence of a non-coding sequence or an addition interrupting the translation of the full-length TPS2 polypeptide). Alternatively (or in combination), the recombinant yeast strain can be genetically-engineered to remove a part or the totality of the endogenous tps2 gene or ortholog from the yeast's genome. In the context of the present disclosure, a deletion refers to the removal of at least one nucleic acid residue of the tps2 gene. In such instance, while a section of the tps2 gene or its ortholog could be expressed (for example the section (if any) which precedes the deletion) but a functional TPS2 polypeptide could not be produced. In another alternative, the recombinant yeast strain can be genetically-engineered to include one of more nucleic acid residue substitution in the tps2 gene or in the tps2 gene ortholog. The one or more nucleic acid residue substitution can cause the introduction of a stop codon in the open-reading frame of the tps2 gene/ortholog or at least one amino acid substitution in the corresponding polypeptide which will no longer be considered a functional or biologically active TPS2 polypeptide. The recombinant yeast strain can be genetically engineered to impede or prevent the expression of the tps2 gene or its ortholog by manipulating the non-coding sequence (promoter for example) associated with the coding sequence of the tps2 gene. The nucleic acid sequence of the promoter of the tps2 gene can be modified to remove, add and/or substitute at least one nucleic acid residue so as to reduce or prevent the expression of the tps2 gene or its ortholog. The mutation, disruption and/or deletion can be made in one of the copy of the tps2 gene or its ortholog present in the yeast's genome or in both copies of the tps2 gene or its ortholog present in the yeast's genome.

The second genetic modification can be associated with the production of an heterologous trehalase, a trehalase variant or a trehalase fragment (having trehalase activity). In such instance, the genetic manipulation is made to add of an heterologous trehalase-encoding gene (and, optionally, additional non-coding region for facilitating or increasing the expression of the trehalase-encoding gene) and is intended to either provide or increase trehalase activity of the recombinant strain.

As used in the context of the present disclosure, a trehalase is an enzyme capable of hydrolyzing one molecule of trehalose in two molecules of glucose. Trehalases (α,α-trehalose-1-C-glucohydrolase, EC 3.2.1.28) have been reported from many organisms including prokaryotes, plants and animals. At least two-types of trehalases, based on their pH optima, have been characterized: acid trehalases (mostly extracellular, usually associated with the yeast's membrane) and neutral trehalases (usually cytosolic). The recombinant yeast strain of the present disclosure can be genetically engineered to express an acid trehalase, a neutral trehalase or both. In some instances, the heterologous trehalase is produced and transported outside the yeast cell (e.g., extracellular).

The heterologous trehalase(s) expressed by the recombinant yeast strain can be provided from any heterologous organism (yeast, bacteria, plants or animals). The term "heterologous" when used in reference to a nucleic acid molecule (such as a promoter or a coding sequence) or a trehalase refers to a nucleic acid molecule or a trehalase that is not natively found in the host yeast. "Heterologous" also includes a native coding region, or portion thereof, that is removed from the source organism and subsequently reintroduced into the source organism in a form that is different from the corresponding native gene, e.g., not in its natural location in the organism's genome. The heterologous nucleic acid molecule is purposively introduced into the yeast. A "heterologous" nucleic acid molecule or trehalase may be derived from any source, e.g., eukaryotes, prokaryotes, viruses, etc. In an embodiment, the heterologous nucleic acid molecule may be derived from an eukaryote (such as, for example, another yeast) or a prokaryote (such as, for example, a bacteria). The term "heterologous" as used herein also refers to an element (nucleic acid or protein) that is derived from a source other than the endogenous source. Thus, for example, a heterologous element could be derived from a different strain of host cell, or from an organism of a different taxonomic group (e.g., different kingdom, phylum, class, order, family genus, or species, or any subgroup within one of these classifications). The term "heterologous" is also used synonymously herein with the term "exogenous".

The heterologous trehalase can be derived from the genus *Aspergillus* and, in some instances, from the species *Aspergillus fumigatus* or *Aspergillus nidulans*. It is possible to use an heterologous trehalase which does not comprise a tethering region and does not have the ability to associate with the surface of the cell producing same. In some embodiments, the heterologous trehalase has or consists of the amino acid sequence of SEQ ID NO: 1 or 2. For example, the recombinant yeast host cell can be genetically manipulated to express one or more heterologous trehalase genes.

The heterologous trehalase can be a variant of a known trehalase, for example a variant of the trehalase having the amino acid sequence of SEQ ID NO: 1 or 2. The trehalase variants have at least 50%, 55%, 60%, 65%, 70%, 75%, 80%, 85%, 90%, 95%, 96%, 97%, 98% or 99% identity to the trehalases described herein. A variant comprises at least one amino acid difference when compared to the amino acid sequence of the native trehalase. The term "percent identity", as known in the art, is a relationship between two or more polypeptide sequences or two or more polynucleotide sequences, as determined by comparing the sequences. The level of identity can be determined conventionally using known computer programs. Identity can be readily calculated by known methods, including but not limited to those described in: Computational Molecular Biology (Lesk, A. M., ed.) Oxford University Press, N Y (1988); Biocomputing: Informatics and Genome Projects (Smith, D. W., ed.) Academic Press, N Y (1993); Computer Analysis of Sequence Data, Part I (Griffin, A. M., and Griffin, H. G., eds.) Humana Press, N J (1994); Sequence Analysis in Molecular Biology (von Heinje, G., ed.) Academic Press (1987); and Sequence Analysis Primer (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences disclosed herein were performed using the Clustal method of alignment (Higgins and Sharp (1989) CABIOS. 5:151-153) with the default parameters (GAP PENALTY=10, GAP LENGTH PEN ALT Y=10). Default parameters for pairwise alignments using the Clustal method were KTUPLB 1, GAP PENALTY=3, WINDOW=5 and DIAGONALS SAVED=5.

The variant heterologous trehalases described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide.

A "variant" of the trehalase can be a conservative variant or an allelic variant. As used herein, a conservative variant refers to alterations in the amino acid sequence that do not adversely affect the biological functions of the trehalase. A substitution, insertion or deletion is said to adversely affect the protein when the altered sequence prevents or disrupts a biological function associated with the trehalase (e.g., the hydrolysis of trehalose into two glucose molecules). For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the trehalase.

The heterologous trehalase can be a fragment of a known trehalase or fragment of a variant of a known trehalase (such as, for example, a fragment of the trehalase having the amino acid sequence of SEQ ID NO: 1 or 2). Trehalase "fragments" have at least at least 100, 200, 300, 400, 500, 600, 700, 800, 900, 1 000 or more consecutive amino acids of the trehalase. A fragment comprises at least one less amino acid residue when compared to the amino acid sequence of the trehalase and still possess the enzymatic activity of the full-length trehalase. In some embodiments, fragments of the trehalases can be employed for producing the corresponding full-length trehalase by peptide synthesis. Therefore, the fragments can be employed as intermediates for producing the full-length proteins.

The heterologous nucleic acid molecule encoding the heterologous trehalase, variant or fragment can be integrated in the genome of the yeast host cell. The term "integrated" as used herein refers to genetic elements that are placed, through molecular biology techniques, into the genome of a host cell. For example, genetic elements can be placed into the chromosomes of the host cell as opposed to in a vector such as a plasmid carried by the host cell. Methods for integrating genetic elements into the genome of a host cell are well known in the art and include homologous recombination. The heterologous nucleic acid molecule can be present in one or more copies in the yeast host cell's genome. Alternatively, the heterologous nucleic acid molecule can be independently replicating from the yeast's genome. In such embodiment, the nucleic acid molecule can be stable and self-replicating.

The present disclosure also provides nucleic acid molecules for modifying the yeast host cell so as to allow the expression of the heterologous trehalase, variant or fragment. The nucleic acid molecule may be DNA (such as complementary DNA, synthetic DNA or genomic DNA) or RNA (which includes synthetic RNA) and can be provided in a single stranded (in either the sense or the antisense strand) or a double stranded form. The contemplated nucleic acid molecules can include alterations in the coding regions, non-coding regions, or both. Examples are nucleic acid molecule variants containing alterations which produce silent substitutions, additions, or deletions, but do not alter the properties or activities of the encoded trehalases, variants or fragments.

In some embodiments, the nucleic acid molecules encoding the heterologous trehalase and/or glucoamylase, fragment or variant are codon-optimized with respect to the intended recipient recombinant yeast host cell. As used herein the term "codon-optimized coding region" means a nucleic acid coding region that has been adapted for expression in the cells of a given organism by replacing at least one, or more than one, codons with one or more codons that are more frequently used in the genes of that organism. In general, highly expressed genes in an organism are biased towards codons that are recognized by the most abundant tRNA species in that organism. One measure of this bias is the "codon adaptation index" or "CAI," which measures the extent to which the codons used to encode each amino acid in a particular gene are those which occur most frequently in a reference set of highly expressed genes from an organism. The CAI of codon optimized sequences described herein corresponds to between about 0.8 and 1.0, between about 0.8 and 0.9, or about 1.0.

The present disclosure also provides nucleic acid molecules that are hybridizable to the complement nucleic acid molecules encoding the heterologous trehalase, the heterologous glucoamylase as well as variants or fragments. A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein. The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acid molecules contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived. For hybridizations with shorter nucleic acids, i.e. e., oligonucleotides, the position of mismatches becomes more important, and the length of the oligonucleotide determines its specificity. In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The nucleic acid molecules comprise a coding region for the heterologous trehalase as well as its variants and fragments. A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. In an embodiment, the coding region can be referred to as an open reading frame. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

The nucleic acid molecules described herein can comprise transcriptional and/or translational control regions. "Transcriptional and translational control regions" are DNA regulatory regions, such as promoters, enhancers, terminators, and the like, that provide for the expression of a coding region in a host cell. In eukaryotic cells, polyadenylation signals are control regions.

The heterologous nucleic acid molecule can be introduced in the yeast host cell using a vector. A "vector," e.g., a "plasmid", "cosmid" or "YAC" (yeast artificial chromosome) refers to an extra chromosomal element and is usually in the form of a circular double-stranded DNA molecule. Such vectors may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

In the heterologous nucleic acid molecule, the promoter and the nucleic acid molecule(s) coding for the heterologous protein(s) are operatively linked to one another. In the context of the present disclosure, the expressions "operatively linked" or "operatively associated" refers to fact that the promoter is physically associated to the nucleotide acid molecule coding for the heterologous protein in a manner that allows, under certain conditions, for expression of the heterologous protein from the nucleic acid molecule. In an embodiment, the promoter can be located upstream (5') of the nucleic acid sequence coding for the heterologous protein. In still another embodiment, the promoter can be located downstream (3') of the nucleic acid sequence coding for the heterologous protein. In the context of the present disclosure, one or more than one promoter can be included in the heterologous nucleic acid molecule. When more than one promoter is included in the heterologous nucleic acid molecule, each of the promoters is operatively linked to the nucleic acid sequence coding for the heterologous protein. The promoters can be located, in view of the nucleic acid molecule coding for the heterologous protein, upstream, downstream as well as both upstream and downstream.

"Promoter" refers to a DNA fragment capable of controlling the expression of a coding sequence or functional RNA. The term "expression," as used herein, refers to the transcription and stable accumulation of sense (mRNA) from the heterologous nucleic acid molecule described herein. Expression may also refer to translation of mRNA into a polypeptide. Promoters may be derived in their entirety from a native gene, or be composed of different elements derived from different promoters found in nature, or even comprise synthetic DNA segments. It is understood by those skilled in the art that different promoters may direct the expression at different stages of development, or in response to different environmental or physiological conditions. Promoters which cause a gene to be expressed in most cells at most times at a substantial similar level are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of the polymerase.

The promoter can be heterologous to the nucleic acid molecule encoding the heterologous protein. The promoter can be heterologous or derived from a strain being from the same genus or species as the recombinant yeast host cell. In an embodiment, the promoter is derived from the same genera or species of the yeast host cell and the heterologous protein is derived from different genera that the yeast host cell.

In the context of the present disclosure, the heterologous protein can be further modified to include a tethering region (so as to allow the localization of the secreted heterologous protein at the external surface of the yeast host cell) and/or fused to another entity (to create a fusion protein). Alternatively, the heterologous protein (such as the heterologous trehalase) can be modified so as to remove its tethering region.

In the context of the present disclosure, the recombinant yeast host cell can include at least two "second" genetic modifications, one in leading to the reduction in the production of one or more native enzymes that function to produce trehalose or regulating trehalose synthesis and another one leading to the expression of an heterologous trehalase.

In some instances, the recombinant yeast host cell can include a further genetic modification for reducing the production of one or more native enzyme that function to catabolize (breakdown) formate. As used in the context of the present disclosure, the expression "native polypeptides that function to catabolize formate" refers to polypeptides which are endogenously found in the recombinant yeast host cell. Native enzymes that function to catabolize formate include, but are not limited to, the FDH1 and the FDH2 polypeptides (also referred to as FDH1 and FDH2 respectively). In an embodiment, the recombinant yeast host cell bears a genetic modification in at least one of the fdh1 gene (encoding the FDH1 polypeptide), the fdh2 gene (encoding the FDH2 polypeptide) or orthologs thereof. In another embodiment, the recombinant yeast host cell bears genetic modifications in both the fdh1 gene (encoding the FDH1 polypeptide) and the fdh2 gene (encoding the FDH2 polypeptide) or orthologs thereof. Examples of recombinant yeast host cells bearing such genetic modification(s) leading to the reduction in the production of one or more native enzymes that function to catabolize formate are described in WO 2012/138942. Preferably, the recombinant yeast host cell has genetic modifications (such as a genetic deletion or insertion) in the fdh1 gene and in the fdh2 gene which would cause the host cell to have knocked-out fdh1 and fdh2 genes.

In some instances, the recombinant yeast host cell can include a further genetic modification allowing the expression of an heterologous glucoamylase. In an embodiment, the heterologous glucoamylase is derived from a γ-amylase, such as, for example, the glucoamylase of *Saccharomycoces filbuligera* (e.g., encoded by the glu 0111 gene). In instances in which the recombinant yeast host cell is intended to be used at elevated temperatures, genetic modifications for increasing the robustness of a genetically-modified recombinant yeast host cell expressing an heterologous glucoamylase are described in PCT/IB2016/055162 filed on Aug. 29, 2016 and herewith incorporated in its entirety.

The recombinant yeast host cell can be further genetically modified to allow for the production of additional heterologous proteins. In an embodiment, the recombinant yeast host cell can be used for the production of an enzyme, and especially an enzyme involved in the cleavage or hydrolysis of its substrate (e.g., a lytic enzyme and, in some embodiments, a saccharolytic enzyme). In still another embodiment, the enzyme can be a glycoside hydrolase. In the context of the present disclosure, the term "glycoside hydrolase" refers to an enzyme involved in carbohydrate digestion, metabolism and/or hydrolysis, including amylases, cellulases, hemicellulases, cellulolytic and amylolytic accessory enzymes, inulinases, levanases, trehalases, pectinases, and pentose sugar utilizing enzymes. In another embodiment, the enzyme can be a protease. In the context of the present disclosure, the term "protease" refers to an enzyme involved in protein digestion, metabolism and/or hydrolysis. In yet another embodiment, the enzyme can be an esterase. In the context of the present disclosure, the term "esterase" refers to an enzyme involved in the hydrolysis of an ester from an acid or an alcohol, including phosphatases such as phytases.

The additional heterologous protein can be an "amylolytic enzyme", an enzyme involved in amylase digestion, metabolism and/or hydrolysis. The term "amylase" refers to an enzyme that breaks starch down into sugar. All amylases are glycoside hydrolases and act on α-1,4-glycosidic bonds. Some amylases, such as γ-amylase (glucoamylase), also act on α-1,6-glycosidic bonds. Amylase enzymes include α-amylase (EC 3.2.1.1), β-amylase (EC 3.2.1.2), and γ-amylase (EC 3.2.1.3). The α-amylases are calcium metalloenzymes, unable to function in the absence of calcium. By acting at random locations along the starch chain, α-amylase breaks down long-chain carbohydrates, ultimately yielding maltotriose and maltose from amylose, or maltose, glucose and "limit dextrin" from amylopectin. Because it can act anywhere on the substrate, α-amylase tends to be faster-acting than β-amylase. In an embodiment, the heterologous protein is derived from a α-amylase such as, for example, from the α-amylase of Bacillus amyloliquefacens. Another form of amylase, β-amylase is also synthesized by bacteria, fungi, and plants. Working from the non-reducing end, β-amylase catalyzes the hydrolysis of the second α-1,4 glycosidic bond, cleaving off two glucose units (maltose) at a time. Another amylolytic enzyme is α-glucosidase that acts on maltose and other short malto-oligosaccharides produced by α-, β-, and γ-amylases, converting them to glucose. Another amylolytic enzyme is pullulanase. Pullulanase is a specific kind of glucanase, an amylolytic exoenzyme, that degrades pullulan. Pullulan is regarded as a chain of maltotriose units linked by alpha-1,6-glycosidic bonds. Pullulanase (EC 3.2.1.41) is also known as pullulan-6-glucanohydrolase (debranching enzyme). Another amylolytic enzyme, isopullulanase, hydrolyses pullulan to isopanose (6-alpha-maltosylglucose). Isopullulanase (EC 3.2.1.57) is also known as pullan 4-glucanohydrolase. An "amylase" can be any enzyme involved in amylase digestion, metabolism and/or hydrolysis, including α-amylase, β-amylase, glucoamylase, pullulanase, isopullulanase, and alpha-glucosidase.

The additional heterologous protein can be a "cellulolytic enzyme", an enzyme involved in cellulose digestion, metabolism and/or hydrolysis. The term "cellulase" refers to a class of enzymes that catalyze cellulolysis (i.e. the hydrolysis) of cellulose. Several different kinds of cellulases are known, which differ structurally and mechanistically. There are general types of cellulases based on the type of reaction catalyzed: endocellulase breaks internal bonds to disrupt the crystalline structure of cellulose and expose individual cellulose polysaccharide chains; exocellulase cleaves 2-4 units from the ends of the exposed chains produced by endocellulase, resulting in the tetrasaccharides or disaccharide such as cellobiose. There are two main types of exocellulases (or cellobiohydrolases, abbreviate CBH)—one type working processively from the reducing end, and one type working processively from the non-reducing end of cellulose; cellobiase or beta-glucosidase hydrolyses the exocellulase product into individual monosaccharides; oxidative cellulases that depolymerize cellulose by radical reactions, as for instance cellobiose dehydrogenase (acceptor); cellulose phosphorylases that depolymerize cellulose using phosphates instead of water. In the most familiar case of cellulase activity, the enzyme complex breaks down cellulose to beta-glucose. A "cellulase" can be any enzyme involved in cellulose digestion, metabolism and/or hydrolysis, including an endoglucanase, glucosidase, cellobiohydrolase, xylanase, glucanase, xylosidase, xylan esterase, arabinofuranosidase, galactosidase, cellobiose phosphorylase, cellodextrin phosphorylase, mannanase, mannosidase, xyloglucanase, endoxylanase, glucuronidase, acetylxylanesterase, arabinofuranohydrolase, swollenin, glucuronyl esterase, expansin, pectinase, and feruoyl esterase protein.

The additional heterologous protein can have "hemicellulolytic activity", an enzyme involved in hemicellulose digestion, metabolism and/or hydrolysis. The term "hemicellulase" refers to a class of enzymes that catalyze the hydrolysis of cellulose. Several different kinds of enzymes are known to have hemicellulolytic activity including, but not limited to, xylanases and mannanases.

The additional heterologous protein can have "xylanolytic activity", an enzyme having the is ability to hydrolyze glycosidic linkages in oligopentoses and polypentoses. The term "xylanase" is the name given to a class of enzymes which degrade the linear polysaccharide beta-1,4-xylan into xylose, thus breaking down hemicellulose, one of the major components of plant cell walls. Xylanases include those enzymes that correspond to Enzyme Commission Number 3.2.1.8. The heterologous protein can also be a "xylose metabolizing enzyme", an enzyme involved in xylose digestion, metabolism and/or hydrolysis, including a xylose isomerase, xylulokinase, xylose reductase, xylose dehydrogenase, xylitol dehydrogenase, xylonate dehydratase, xylose transketolase, and a xylose transaldolase protein. A "pentose sugar utilizing enzyme" can be any enzyme involved in pentose sugar digestion, metabolism and/or hydrolysis, including xylanase, arabinase, arabinoxylanase, arabinosidase, arabinofuranosidase, arabinoxylanase, arabinosidase, and arabinofuranosidase, arabinose isomerase, ribulose-5-phosphate 4-epimerase, xylose isomerase, xylulokinase, xylose reductase, xylose dehydrogenase, xylitol dehydrogenase, xylonate dehydratase, xylose transketolase, and/or xylose transaldolase.

The additional heterologous protein can have "mannanic activity", an enzyme having the is ability to hydrolyze the terminal, non-reducing R-D-mannose residues in β-D-mannosides. Mannanases are capable of breaking down hemicellulose, one of the major components of plant cell walls. Xylanases include those enzymes that correspond to Enzyme Commission Number 3.2.25.

The additional heterologous protein can be a "pectinase", an enzyme, such as pectolyase, pectozyme and polygalacturonase, commonly referred to in brewing as pectic enzymes. These enzymes break down pectin, a polysaccharide substrate that is found in the cell walls of plants.

The additional heterologous protein can have "phytolytic activity", an enzyme catalyzing the conversion of phytic acid into inorganic phosphorus. Phytases (EC 3.2.3) can be belong to the histidine acid phosphatases, β-propeller phytases, purple acid phosphastases or protein tyrosine phosphatase-like phytases family.

The additional heterologous protein can have "proteolytic activity", an enzyme involved in protein digestion, metabolism and/or hydrolysis, including serine proteases, threonine proteases, cysteine proteases, aspartate proteases, glutamic acid proteases and metalloproteases.

When the recombinant yeast host cell expresses an heterologous protein, it can be further modified to increase its robustness at high temperatures. Genetic modifications for increasing the robustness of a genetically-modified recombinant yeast host cell are described in U.S. 62/214,412 filed on Sep. 4, 2015 and herewith incorporated in its entirety.

Methods of Using the Recombinant Yeast Host Cells for Limiting the Accumulation of Trehalose During Fermentation The recombinant yeast host cells described herein can be used to limit and, in some embodiments, prevent the production, accumulation or excretion of trehalose during fermentation. As indicated above, the recombinant yeast host cells have a second genetic modification which either limits the production of endogenous trehalose by the recombinant yeast or hydrolyzes the trehalose that is being endogenously production.

The process comprises combining a substrate to be hydrolyzed (optionally included in a fermentation medium) with the recombinant yeast host cells. In an embodiment, the substrate to be hydrolyzed is a lignocellulosic biomass and, in some embodiments, it comprises starch (in a gelatinized or raw form). In other embodiments, the substrate to be hydrolyzed comprises maltodextrin. In some embodiments, the use of recombinant yeast host cells limits or avoids the need of adding trehalase in a purified form during fermentation to limit the amount of trehalose. This embodiment is advantageous because it can reduce or eliminate the need to supplement the fermentation medium with external source of purified enzymes (e.g., glucoamylase and/or trehalase) while allowing the fermentation of the lignocellulosic biomass into a fermentation product (such as ethanol). However, in some circumstances, it may be advisable to supplement the medium with a trehalase (such as, for example, the trehalase having the amino acid sequence of SEQ ID NO: 1 or 2) in a purified. Such trehalase can be produced in a recombinant fashion in a recombinant yeast host cell.

The recombinant yeast host cells described herein can be used to increase the production of a fermentation product during fermentation. As indicated above, the recombinant yeast host cells have a second genetic modification which either limits the production of endogenous trehalose by the recombinant yeast or hydrolyzes the trehalose that is being endogenously production and such second genetic modifications can improve the yield in one or more fermentation products. The process comprises combining a substrate to be hydrolyzed (optionally included in a fermentation medium) with the recombinant yeast host cells. In an embodiment, the substrate to be hydrolyzed is a lignocellulosic biomass and, in some embodiments, it comprises starch (in a gelatinized or raw form). In some embodiments, the use of recombinant yeast host cells limits or avoids the need of adding trehalase in a purified form during fermentation to limit the amount of trehalose. This embodiment is advantageous because it can reduce or eliminate the need to supplement the fermentation medium with external source of purified enzymes (e.g., glucoamylase and/or trehalase) while allowing the fermentation of the lignocellulosic biomass into a fermentation product (such as ethanol). However, in some circumstances, it may be advisable to supplement the medium with a trehalase (such as, for example, the trehalase having the amino acid sequence of SEQ ID NO: 1 or 2) in a purified. Such trehalase can be produced in a recombinant fashion in a recombinant yeast host cell.

The production of ethanol can be performed at temperatures of at least about 25° C., about 28° C. about 30° C. about 31° C. about 32° C. about 33° C., about 34° C., about 35° C., about 36° C., about 37° C., about 38° C., about 39° C., about 40° C., about 41° C., about 42° C., or about 50° C. In some embodiments, when a thermotolerant yeast cell is used in the process, the process can be conducted at temperatures above about 30° C., about 31° C., about 32° C., about 33° C., about 34° C., about 35° C., about 36° C., about 37° C., about 38° C., about 39° C., about 40° C., about 41° C., about 42° C., or about 50° C.

In some embodiments, the process can be used to produce ethanol at a particular rate. For example, in some embodiments, ethanol is produced at a rate of at least about 0.1 mg per hour per liter, at least about 0.25 mg per hour per liter, at least about 0.5 mg per hour per liter, at least about 0.75 mg per hour per liter, at least about 1.0 mg per hour per liter, at least about 2.0 mg per hour per liter, at least about 5.0 mg per hour per liter, at least about 10 mg per hour per liter, at least about 15 mg per hour per liter, at least about 20.0 mg per hour per liter, at least about 25 mg per hour per liter, at least about 30 mg per hour per liter, at least about 50 mg per hour per liter, at least about 100 mg per hour per liter, at least about 200 mg per hour per liter, or at least about 500 mg per hour per liter.

Ethanol production can be measured using any method known in the art. For example, the quantity of ethanol in fermentation samples can be assessed using HPLC analysis. Many ethanol assay kits are commercially available that use, for example, alcohol oxidase enzyme based assays.

The present invention will be more readily understood by referring to the following examples which are given to illustrate the invention rather than to limit its scope.

Example I—Material and Methods

Figure 8A:
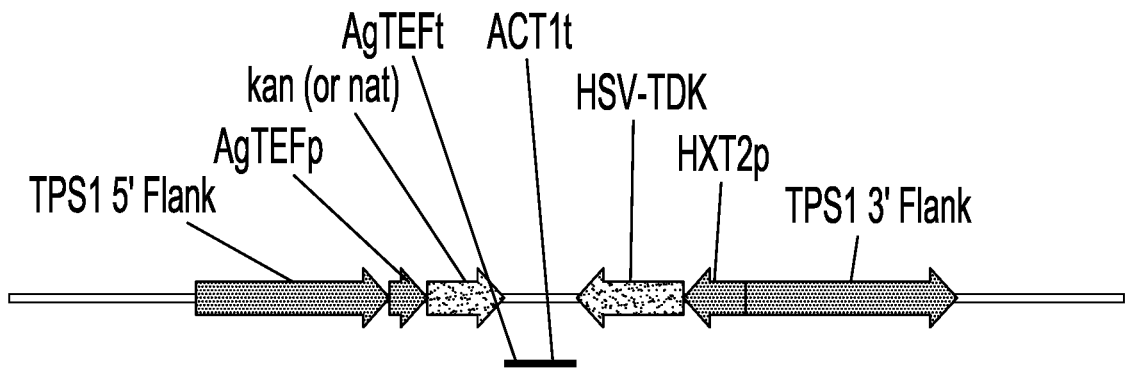
FIG. 8A to 8E illustrate the genetic maps of the different cassettes used to generate some of the recombinant yeast strains of the Examples. (A) Map of the MA613 cassette used for making the M4652 strain. KT-MX and NT-MX cassette used to knock-out the tps1 open reading frame. The cassette contains the positive selection markers kanamycin gene or nourseothricin gene under control of the *Ashbya gossypii* tef promoter and terminator along with the HSV-thymidine kinase negative selection marker under control of the *S. cerevisiae* hxt2 promoter and act1 terminator. (B) Map of the MA614 cassette used for making the M4653 strain. KT-MX and NT-MX cassette used to knock-out the tps2 open reading frame. The cassette contains the positive selection markers kanamycin gene or nourseothricin gene under control of the *Ashbya gossypii* tef promoter and terminator along with the HSV-thymidine kinase negative selection marker under control of the *S. cerevisiae* hxt2 promoter and act1 terminator. (C) Map of the MA1920 cassette for making the M11245 strain and integrating the MP244 trehalase at the FCY1 locus under control of the native *S. cerevisiae* tef2 promoter and adh3 terminator. (D) Map of the MAP516 cassette for making the M10957 strain and for integrating the MP848 trehalase at the FCY1 locus under control of the native *S. cerevisiae* tef2 promoter and idp1 terminator. (E) Map of the MAP811 cassette for making the M12121 and M13913 strains and for integrating MP244 trehalase at the IME1 locus under control of the native *S. cerevisiae* tef2 promoter and idp1 terminator.
Figure 8B:
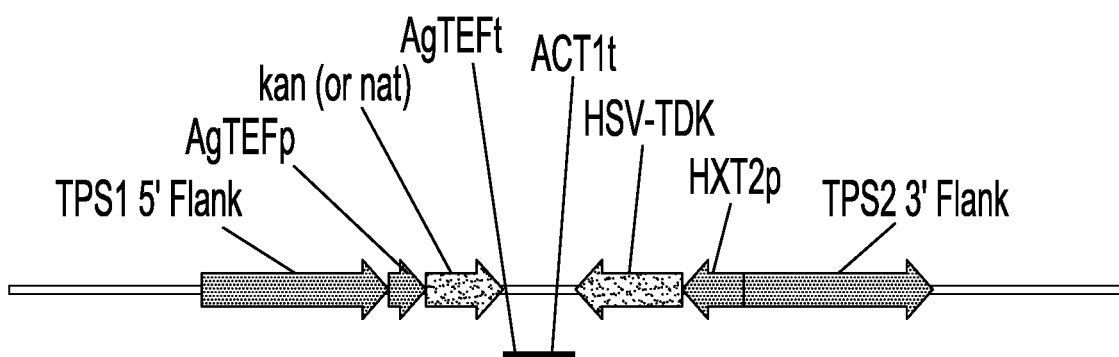
Figure 8C:
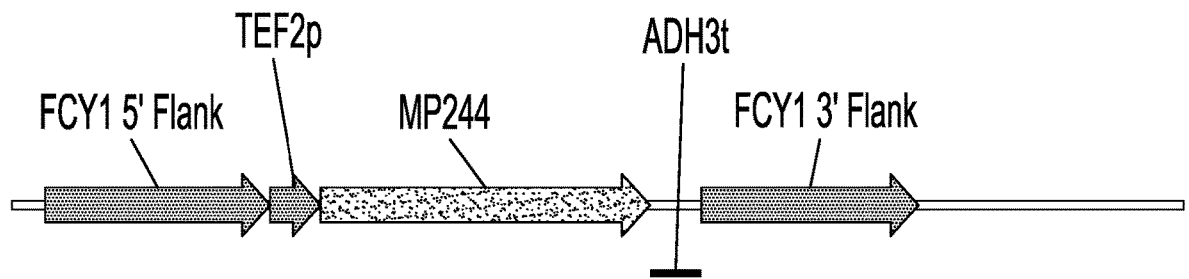
Figure 8D:
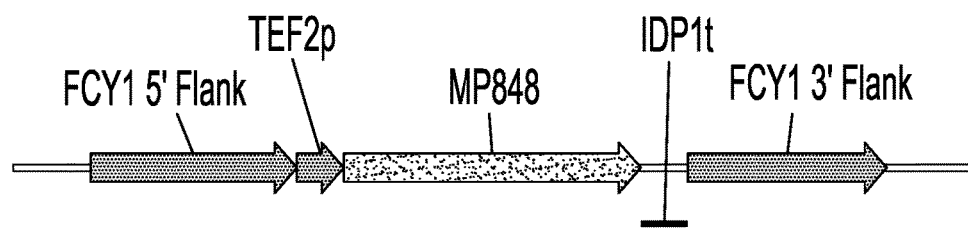
Figure 8E:
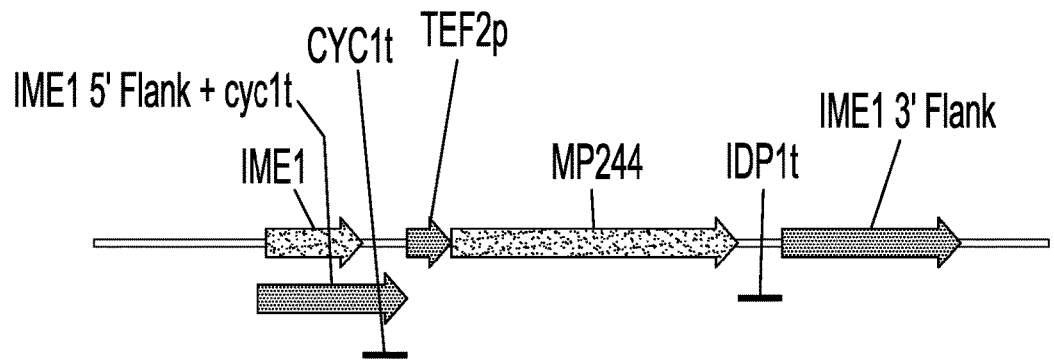

Strain M4652 was constructed using the KT (Kanamycin and HSV-thymidine kinase) and NT (nourseothricin and HSV-thymidine kinase) recyclable MX cassettes (FIG. 8A) targeting a direct integration and removal of the tps1 open reading frame. The KT-max and NT-max cassettes were PCR amplified, along with non-coding 5' and 3' flanks, creating overlapping homologous ends to promote recombination in vivo. The PCR products were transformed into the diploid *Saccharomyces cerevisiae* host strain, M2390, and subsequently selected on YPD containing G418 (200 µg/ml) and cloNat (100 µg/ml) to select for removal of both tps1 alleles. Table 1 below provides the nucleic acid sequence of the primers used to make the MA613 genetic cassette used to create the M4652 strain.

TABLE 1

Nucleic acid sequence of the primers used to make the MA613 genetic cassette used to create the M4652 strain.

| Target | SEQ ID NO: | Sequence |
|---|---|---|
| TPS1 5' Flank | 19 | GCAGAGGATTACTT GGACATTAACGGTT CTCCTATC |
|  | 20 | GGACGAGGCAAGCTA AACAGATCTCTAGAC CTAAGTTCTATGTCT TAATAAGTCTGTATG |

TABLE 1-continued

Nucleic acid sequence of the primers used to make the MA613 genetic cassette used to create the M4652 strain.

| Target | SEQ ID NO: | Sequence |
|---|---|---|
| KT-MX and NT-MX | 21 | TACTCACATACAGAC TTATTAAGACATAGA ACTTAGGTCTAGAGA TCTGTTTAGCTTGCC |
|  | 22 | GAATAGACGATCGTC TCATTTGCATCGGGT TCAGAGACTACATGA TAGTCCAAAGAAAAG |
| TPS2 3' Flank | 23 | CCGTTTCTTTTCTTT GGACTATCATGTAGT CTCTGAACCCGATGC AAATGAGACGATCGT |
|  | 24 | GCAAGAGGCTCCTCC ACTGGCATTTTCACG ATTTGG |

Strain M4653 was constructed using the same method as described in the M4652 engineering. However, the 5' and 3' non-coding flanking regions were designed to target the tps2 region (FIG. 81) for the deletion of the tps2 open reading frame. Table 2 below provides the nucleic acid sequence of the primers used to make the MA614 genetic cassette used to create the M4653 strain.

TABLE 2

Nucleic acid sequence of the primers used to make the MA614 genetic cassette used to create the M4653 strain.

| Target | SEQ ID NO: | Sequence |
|---|---|---|
| TPS2 5' Flank | 25 | GCTGTGCAGCAG GGTATTCTACTA CGTGTTAGCTT |
|  | 26 | GGACGAGGCAAG CTAAACAGATCT CTAGACCTATTC GGCACAGAAATA GTGACAGGCAGT |
| KT-MX and NT-MX | 27 | AATAACACTGCC TGTCACTATTTC TGTGCCGAATAG GTCTAGAGATCT GTTTAGCTTGCC |
|  | 28 | TCTAGTCATAAC CATTTCGTTAAA AAGGGTGTTGAG ACTACATGATAG TCCAAAGAAAAG |
| TPS2 3' Flank | 29 | CCGTTTCTTTTC TTTGGACTATCA TGTAGTCTCAAC ACCCTTTTTAAC GAAATGGTTATG |
|  | 30 | CGTAGATCGACC TTGCCTGGAATC CCAGGTT |

Strain M11245 was engineered to express an heterologous trehalase. The heterologous trehalase gene, MP244 (SEQ ID NO: 1) was codon-optimized for *S. cerevisiae* based on the amino acid sequence from *Aspergillus fumigatus* (GenBank Accession No. XP_748551). The synthesized sequence was used as PCR template to create homologous ends with the *S. cerevisiae* tef2 promoter and adh3 terminator and integrated at then FCY1 loci in the diploid *S. cerevisiae* host strain via homologous recombination in vivo (FIG. 8). Table 3 below provides the nucleic acid sequence of the primers used to make the MA1920 genetic cassette used to create the M11245 strain.

TABLE 3

Nucleic acid sequence of the primers used to make the MA1920 genetic cassette used to create the M11245 strain.

| Target | SEQ ID NO: | Sequence |
|---|---|---|
| FCY1 5' Flank | 31 | CTCGTTGGTAGG GTCCACACCATA GACTTCAG |
|  | 32 | TAGCTATGAAAT TTTTAACTCTTT AAGCTGGCTCT |
| TEF2p | 33 | GATGAGAGCCAG CTTAAAGAGTTA AAAATTTCATAG CTAGGGCGCCAT AACCAAGGTATC |
|  | 34 | CCAACAAAGAAA CCCAAGTAGCCA AGTTTTGAGACA ACATGTTTAGTT AATTATAGTTCG |
| MP244 | 35 | GAATATACGGTC AACGAACTATAA TTAACTAAACAT GTTGTCTCAAAA CTTGGC |
|  | 36 | CAAAGACTTTCA TAAAAGTTTGG GTGCGTAACACG CTATCAAGCGTT GAATTGTCTG |
| ADH3t | 37 | GCTTTGAACGAC AGAAGATACAGA CAATTCAACGCT TGATAGCGTGTT ACGCACCCAAAC |
|  | 38 | TATATAAAATTA AATACGTAAATA CAGCGTGCTGCG TGCTATGAGGAA GAAATCCAAATC |
| FCY1 3' Flank | 39 | AGCACGCAGCAC GCTGTATTTACG TATTTAATTTT |
|  | 40 | GTAGTGCTGTCT GAACAGAATAAA TGCGTTCTTGG |

Strain M10957 was engineered to express an heterologous trehalase. The heterologous trehalase gene, MP848 (SEQ ID NO: 2) was codon-optimized for *S. cerevisiae* based on the amino acid sequence from *Aspergillus nidulans* (GenBank Accession No. P78617). The synthesized sequence was used as PCR template to create homologous ends with the *S. cerevisiae* tef2 promoter and adh3 terminator and integrated at the FCY1 loci in the diploid *S. cerevisiae* host strain via homologous recombination in vivo (FIG. 8). Table 4 below provides the nucleic acid sequence of the primers used to make the MAP516 genetic cassette used to create the M10957 strain.

TABLE 4

Nucleic acid sequence of the primers used to make the MAP516 genetic cassette used to create the M10957 strain.

| Target | SEQ ID NO: | Sequence |
|---|---|---|
| FCY1 5' Flank | 41 | CTGACTCGTTGGTGGGGTCCACACCATAGA |
|  | 42 | GATTGGCGGTCTATAGATACCTTGGTTATGGCGCCCTAGCTATGAAATTTTTAACTCTTC |
| TEF2p | 43 | GAGAGCCAGCTTTTTGAAGAGTTAAAAATTTCATAGCTAGGGCGCCATAACCAAGGTATC |
|  | 44 | GTTTAGTTAATTATAGTTCG |
| MP848 | 45 | TTTTTAGAATATACGGTCAACGAACTATAATTAACTAAACATGAGATTCAAGTCCGTTTT |
|  | 46 | AATGAAAAAAAAAGTGGTAGATTGGGCTACGTAAATTCGATTACAACAAGGAACTGGTT |
| ADH3t | 47 | TCGAATTTACGTAGCCCAATC |
|  | 48 | TATATAAAATTAAATACGTAAATACAGCGTGCTGCGTGCTCAAATGACGTCAAAAGAAGT |
| FCY1 3' Flank | 49 | CATAGGCTCATATAATACTTCTTTTGACGTCATTTGAGCACGCAGCACGCTGTATTTACG |
|  | 50 | GTAGTGCTGTCTGAACAGAATAAATGCGTTCT |

Strain M12121 was constructed using the M11589 background containing the glycerol reduction pathway and heterologous glu011-CO glucoamylase The synthesized sequence was used as PCR template to create homologous ends with the *S. cerevisiae* tef2 promoter and adh3 terminator and integrated at the IME loci in the diploid *S. cerevisiae* host strain via homologous recombination in vivo (FIG. 80). Table 5 below provides the nucleic acid sequence of the primers used to make the MAP811 genetic cassette used to create the M12121 strain.

TABLE 5

Nucleic acid sequence of the primers used to make the MAP811 genetic cassette used to create the M12121 strain.

| Target | SEQ ID NO: | Sequence |
|---|---|---|
| IME1 5' Flank | 51 | CACCTACAGAGAAACAAATTCCTACTGGCACCC |
|  | 52 | TTGGCGGTCTATAGATACCTTGGTTATGGCGCCCGTCGACAACTAAACTGGAATGTGAGG |
| TEF2p | 53 | ACTTTTGTTGTTCCCTCACATTCCAGTTTAGTTGTCGACGGGCGCCATAACCAAGGTATC |
|  | 54 | CCAACAAAGAAACCCAAGTAGCCAAGTTTTGAGACAACATGTTTAGTTAATTATAGTTCG |
| MP244 | 55 | GAATATACGGTCAACGAACTATAATTAACTAAACATGTTGTCTCAAAACTTGGCTACTTG |
|  | 56 | AAATGAAAAAAAAAGTGGTAGATTGGGCTACGTAAATTCGATCAAGCGTTGAATTGTCTG |
| IDP1t | 57 | GCTTTGAACGACAGAAGATACAGACAATTCAACGCTTGATCGAATTTACGTAGCCCAATC |
|  | 58 | ATTTTGAGGGAAGGGGGAAGATTGTAGTACTTTTCGAGAACAAATGACGTCAAAAGAAGT |
| IME1 3' Flank | 59 | TAGGCTCATATAATACTTCTTTTGACGTCATTTGTTCTCGAAAAGTACTACAATCTTCCC |
|  | 60 | GAACTTCTGCCTTTGAACAATTTCCAAACAATTTTCATTGGTC |

Table 6 summarizes the strains used in the Examples.

TABLE 6

Description of the *S. cerevisiae* strains used in the examples.

| Name | Gene inactivated | Gene overexpressed |
|---|---|---|
| M2390 (wild-type) | None | None |
| M4652 | Δtps1 | None |
| M4653 | Δtps2 | None |
| M11245 | None | Gene encoding GeneBank Accession XP_748551 (MP244) |
| M10957 | None | Gene encoding GeneBank Accession P78617 (MP848) |

TABLE 6-continued

Description of the *S. cerevisiae* strains used in the examples.

| Name | Gene inactivated | Gene overexpressed |
|---|---|---|
| M8841 (described in WO2011/153516 and WO2012/138942) | Δgpd2 Δfdh1 Δfdh2 Δfcy1 | Gene encoding *Saccharomycopsis fibuligera* glu0111 (GeneBank Accession CAC83969.1) Gene encoding the PFLA polypeptide (UnitProtKB Accession A1A239) Gene encoding the PFLB polypeptide (UnitProtKB Accession A1A240) Gene encoding the ADHE polypeptide (UnitProtKB Accession A1A067) |
| M11589 | Δgpd2 Δfdh1 Δfdh2 Δfcy1 | *Saccharomycopsis fibuligera* glu0111 (GeneBank Accession CAC83969.1) Gene encoding the PFLA polypeptide (UnitProtKB Accession A1A239) Gene encoding the PFLB polypeptide (UnitProtKB Accession A1A240) Gene encoding the ADHE polypeptide (UnitProtKB Accession A1A067) Gene encoding *Saccharomyces cerevisiae* STL1 (GeneBank Accession NP_010825) |
| M12121 | Δgpd2 Δfdh1 Δfdh2 Δfcy1 | Gene encoding GeneBank Accession XP_748551 (MP244) Gene encoding *Saccharomycopsis fibuligera* glu0111 (GeneBank Accession CAC83969.1) Gene encoding the PFLA polypeptide (UnitProtKB Accession A1A239) Gene encoding the PFLB polypeptide (UnitProtKBAccession A1A240) Gene encoding the ADHE polypeptide (UnitProtKB Accession A1A067) Gene encoding *Saccharomyces cerevisiae* STL1 (GeneBank Accession NP_010825) |
| M13913 | Δgpd2 Δfdh1 Δfdh2 Δfcy1 | Gene encoding GeneBank Accession XP_748551 (MP244) Gene encoding *Saccharomycopsis fibuligera* glu0111 (GeneBank Accession CAC83969.1) Gene encoding the PFLA polypeptide (UniProtKB Accession A1A239) Gene encoding the PFLB polypeptide (UniProtKB Accession A1A240) Gene encoding the ADHE polypeptide (UniProtKB Accession A1A067) |

Figure 7A:
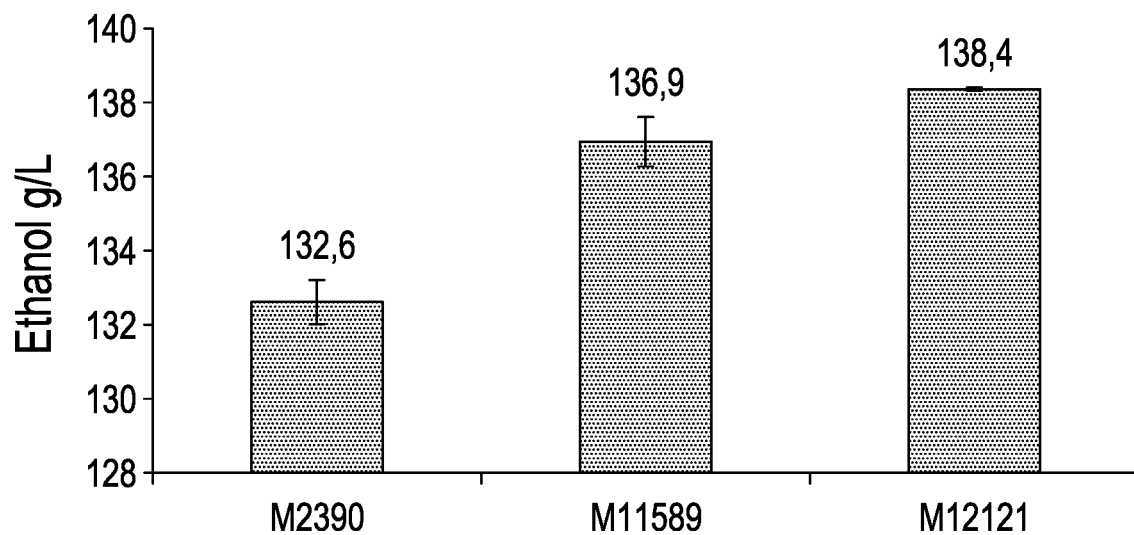
FIGS. 7A and 7B illustrate the effects of fermenting a fermentation medium by a *S. cerevisiae* strain expressing an heterologous glucoamylase and an heterologous trehalase on ethanol production (A) and trehalose concentration (B). Results are shown as ethanol concentration (A, in g/L) or trehalose concentration (B, in g/L) in function of experimental conditions used.

Fermentation using solid corn mash. Conditions for the results presented in FIG. 2: the fermentation was performed using 20% total solids (Ts) liquefied corn mash with the addition of 1000 ppm urea, 0.6 amyloglucosidase unit (AGU)/grams of total solids (gTs) commercial glucoamylase enzyme, 0.1 g/L dry cell weight (DCW) inoculum, with a total fermentation time of 51 h. Temperatures were held at 35° C. for 24 h and lowered to 32° C. for the remainder of the fermentation. Samples were collected and analyzed on HPLC for ethanol titers. Conditions for the results presented in FIG. 5: the fermentation was performed using 25.5% Ts liquefied corn mash with the addition of 500 ppm urea, 0.6 AGU/gTs, commercial glucoamylase for M2390, 0.3 AGU/gTs GA for M8841, and 100 μg/ml of purified MP244, 0.3 g/L dry cell weight (DCW) inoculum, with a total fermentation time of 53 h. Temperatures were held at 35° C. for 24 h and lowered to 32° C. for the remainder of the fermentation. Samples were collected and analyzed on HPLC for ethanol titers and residual trehalose. Conditions for the results presented in FIG. 7: the fermentation was performed using 32% Ts with the addition of 700 ppm urea, 0.48 AGU/gTs commercial glucoamylase for M2390, 0.24 AGU/gTs GA for M11589 and M12121, 0.3 g/L dry cell weight (DCW) inoculum, with a total fermentation time of 48 h. The temperature was held at 33° C. for 24 h and lowered to 31° C. for the remainder of the fermentation. Samples were collected and analyzed on HPLC for ethanol titers and residual trehalose.

Extracellular Trehalose Assay. Residual Trehalose was Measure Using HPLC.

Extracellular trehalase assay. For evaluation of strains expressing secreted heterologous trehalases, a plate based trehalase assay was performed. Strains of interest were 24-72 h in YPD. The cultures were then centrifuged at 3000 rpm to separate the cells from the culture supernatant containing the secreted enzymes. The supernatant is then added to a 1% trehalose solution in 50 mM sodium acetate buffer (pH 5.0). The assay is conducted using a 5:1 trehalose solution:supernatant ratio and incubated at 35° C. for 2 h. The reducing sugars were measured using the dinitrosalicylic acid reagent solution (DNS) method, using a 2:1 DNS:starch assay ratio and boiled at 100° C. for 5 mins. The absorbance is measured at 540 nm.

Intracellular trehalose assay. For evaluation of intracellular trehalose concentrations, strains were grown in YPD at 35° C. Cells were centrifuged at 3000 rpm and the supernatant removed, followed by a repeated water wash. Cultures were normalized to the same OD and 0.25 M sodium carbonate added and incubated at 95° C. for 2 h. Next, 0.2 M sodium acetate pH 5.2 was added, followed by the addition of 1 M acetic acid. A total of 0.5 ml of the slurry was treated with 10 μl of of Megazyme E-trehalase and incubated overnight at 37° C. Glucose was measured using HPLC.

Fermentation using maltodextrin. The fermentation was performed using 260 g/L maltodextrin with the addition of 10 g/L yeast extract, 1 g/L citrate, 500 ppm urea, 0.6 amyloglucosidase unit (AGU)/grams of total solids (gTs) commercial glucoamylase enzyme for the wild type M2390, and 0.3 AGU/gTs for the M8841 and M13913 strains, 0.1 g/L dry cell weight (DCW) inoculum, with a total fermentation time of 54 h. Temperatures were held at 35° C. for 24 h and lowered to 32° C. for the remainder of the fermentation. Samples were collected and analyzed on HPLC for ethanol titers and residual trehalose.

Example II—Elimination of Key Biosynthetic Genes for the Production of Trehalose The material, methods and strains used in this example were presented in Example I.

Figure 2:
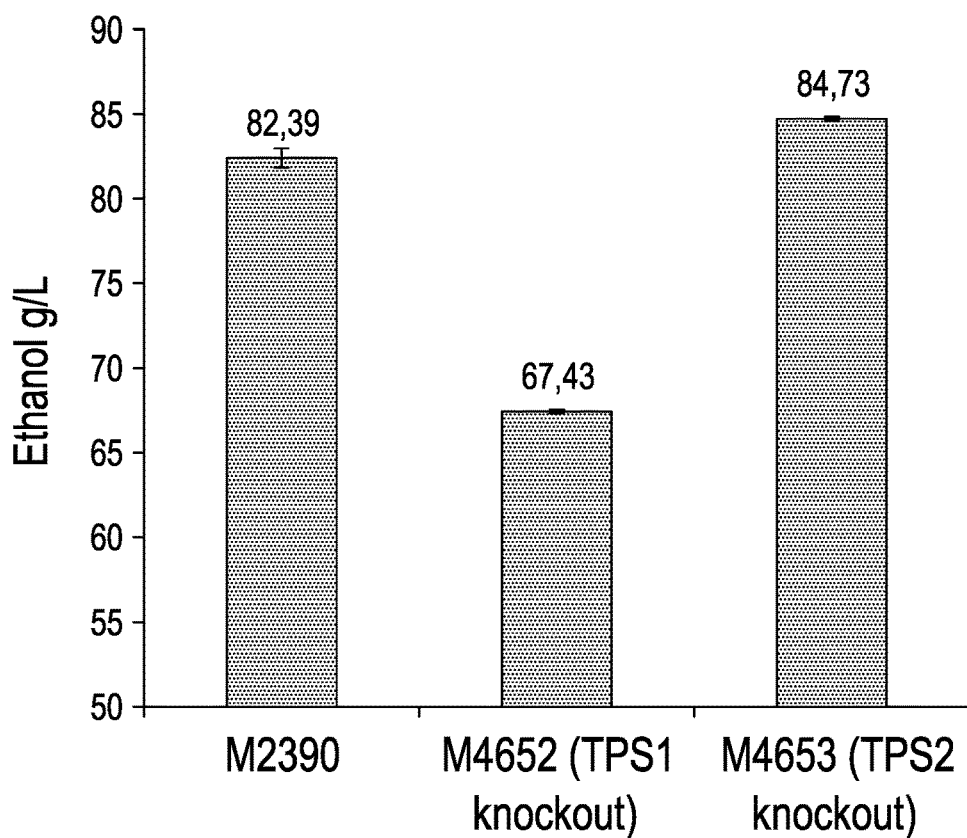
FIG. 2 illustrates the effect of TPS1 (M4652) and TPS2 (M4653) knockouts on ethanol production in 20% corn mash fermentation compared to the conventional parent strain (M2390). Results are shown as ethanol concentration (in g/L) in function of strains used.
Figure 3:
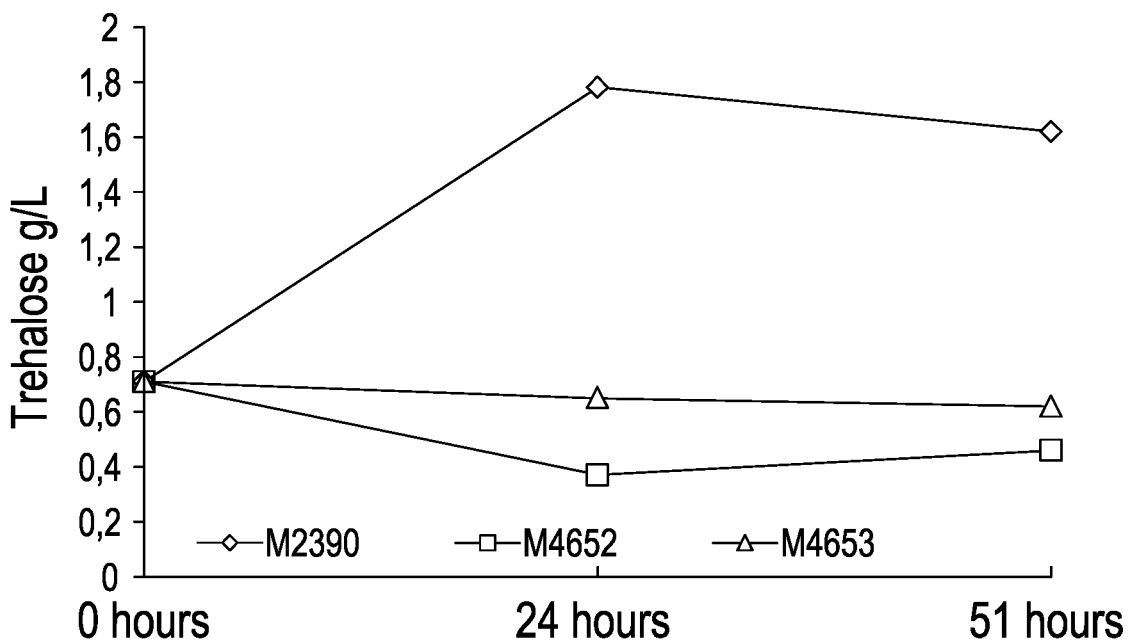
FIG. 3 illustrates the effect of TPS1 (M4652 or ■) and TPS2 (M4653 or ▲) knockouts on trehalose production in 20% corn mash fermentation compared to the conventional parent strain (M2390 or ♦). Results are shown as trehalose concentration (in g/L) in function of strains used.

In order to down regulate/eliminate trehalose production, the native genes responsible for the primary synthetic functions (tps1 and tps2) were individually knocked out in the conventional (wild-type) strain M2390. The M4652 and M4653 strains were then evaluated in corn mash fermentation to characterize ethanol production and residual trehalose. As shown in FIG. 2, the Δtps2 strain (M4653) performed well, providing an additional 2.2 g/L of ethanol production over the conventional strain (M2390), coupled with an 86% reduction in residual trehalose (FIG. 3).

Example III—Expression and Secretion of Heterologous Trehalases Targeting Hydrolysis of Residual Trehalose The material, methods and strains used in this example were presented in Example I.

In order to target the hydrolysis of residual trehalose in an ethanol fermentation, various heterologous trehalases were cloned by integrating 2 copies of the sequence into the conventional yeast host background (M2390) and expressed in *S. cerevisiae*. The screened heterologous trehalase sequences are presented in Table 7.

TABLE 7

Figure 4:
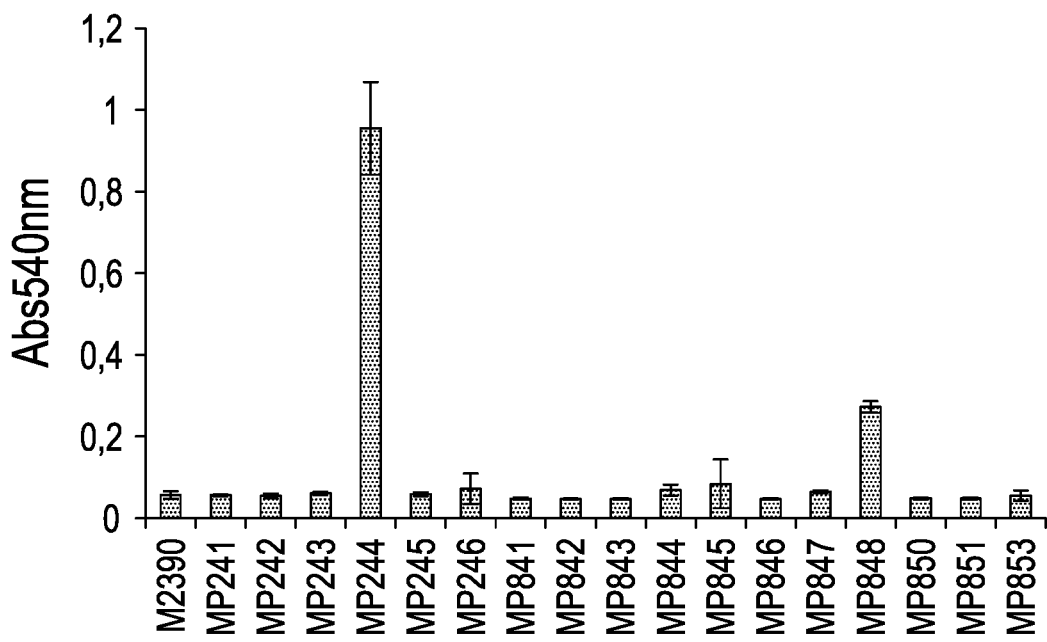
FIG. 4 illustrates the results of a secreted trehalase assay of strains expressing various heterologous trehalases. The results are provided as absorbance at 450 nm in function of strain used. The parental strain M2390 was used as a control. Results are shown were for the following heterologous trehalase MP241 (SEQ ID NO: 4), MP242 (SEQ ID NO: 5), MP243 (SEQ ID NO: 6), MP244 (SEQ ID NO: 1), MP245 (SEQ ID NO: 7), MP246 (SEQ ID NO: 8), MP841 (SEQ ID NO: 9), MP842 (SEQ ID NO: 10), MP843 (SEQ ID NO: 11), MP844 (SEQ ID NO: 12), MP845 (SEQ ID NO: 13), MP846 (SEQ ID NO: 14), MP847 (SEQ ID: 15), MP848 (SEQ ID NO: 2), MP850 (SEQ ID NO: 16), MP851 (SEQ ID NO: 17) and MP853 (SEQ ID NO: 18). MP244 and MP848 were identified as the most active when compared to the parental (negative control) strain M2390.

Amino acid sequence of the heterologous trehalase presented in FIG. 4.

| | Source | Accession # | SEQ ID NO: |
|---|---|---|---|
| MP241 | *Bacillusamyloliquefaciens* | CCG51384 | 4 |
| MP242 | *Debaryomyces hansenii* | CAG87277 | 5 |
| MP243 | *Aspergillus niger* | CAK43526 | 6 |
| MP244 | *Aspergillus fumigatus* | XP_748551 | 1 |
| MP245 | *Trichoderma reesei* | EGR45658 | 7 |
| MP246 | *Kluyveromyceslactis* | CAG99334 | 8 |
| MP841 | *Schizosaccharomyces pombe* | NP_595086 | 9 |
| MP842 | *Neurospora crassa* | XP_960845.1 | 10 |
| MP843 | *Candida albicans* | CAA64476.1 | 11 |
| MP844 | *Debaryomyces hansenii* | XP_459109 | 12 |
| MP845 | *Candida glabrata* | AGG12634 | 13 |
| MP846 | *Kluyveromyces lactis* | P49381 | 14 |
| MP847 | *Rasamsonia emersonii* | AAQ67343 | 15 |
| MP848 | *Aspergillus nidulans* | P78617 | 2 |
| MP850 | *Ashbya gossypii* | NP_984861 | 16 |
| MP851 | *Magnaporthe oryzae* | XP_003714173 | 17 |
| MP853 | *Thermus thermophilus* | YP_004082 | 18 |

The strains were then screened for secreted trehalase activity using a secreted trehalase assay. Results of the secreted trehalase assay are shown in FIG. 4. The MP244 (from *Aspergillus fumigatus*, Accession Number XP_748551 also shown as SEQ ID NO: 1) and MP848 (from *Aspergillus nidulans*, Accession Number P78617 also shown as SEQ ID NO: 2) trehalases exhibited increased trehalase activity.

Figure 5:
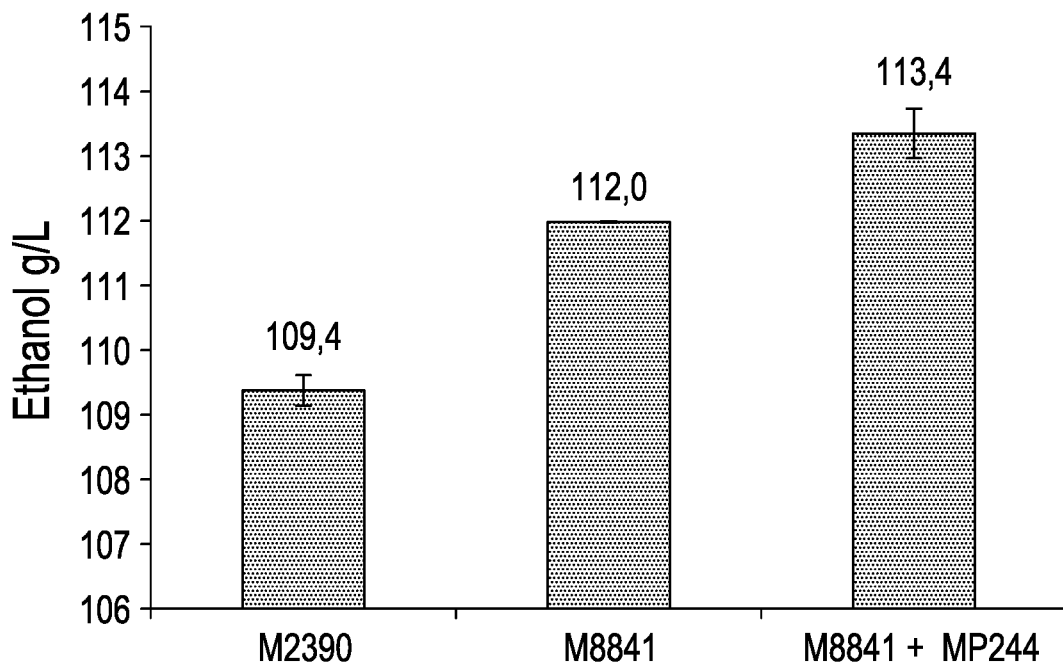
FIG. 5 illustrates the effect of supplementing a fermentation medium with a trehalose on ethanol production. A 25.5% corn mash fermentation was conducted comparing the conventional strain (M2390) to a strain genetically engineered to express a glucoamylase strain (M8841) with and without the addition of purified yeast-made trehalase (MP244). M2390 received a 100% dose of commercial GA, whereas both M8841 treatments received a 50% GA dose. The M8841+MP244 fermentations received 100 μg/ml of purified MP244. Results are shown as ethanol concentration (in g/L) in function of experimental conditions used.
Figure 6:
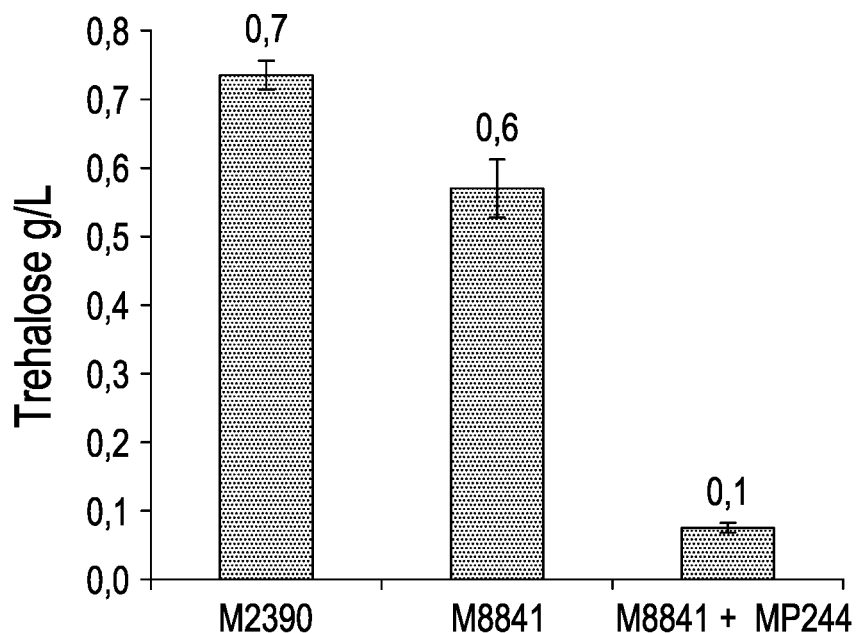
FIG. 6 illustrates the effect of supplementing a fermentation medium with a trehalase on residual trehalose at the end of a 25.5% corn mash fermentation (described in the legend of FIG. 5). Results are shown as trehalose concentration (in g/L) in function of experimental conditions used.

The secreted protein MP244 was His-tagged and purified by FPLC to provide concentrated volumes of yeast-made isolated enzyme. A fermentation was performed using the M8841 strain, in the presence or the absence of 100 μg/mL of purified MP244. The results of such fermentation are shown in FIG. 5. The performance was also compared to the conventional strain (M2390). The addition of the MP244 trehalase provided a 1.25% yield increase over the M8841 strain with no trehalase added. The addition of the MP244 trehalase to the M8841 strain provided a total 3.65% yield increase over the conventional strain M2390. This was correlated with the reduction of residual trehalose measured at the end of fermentation (FIG. 6).

Figure 7B:
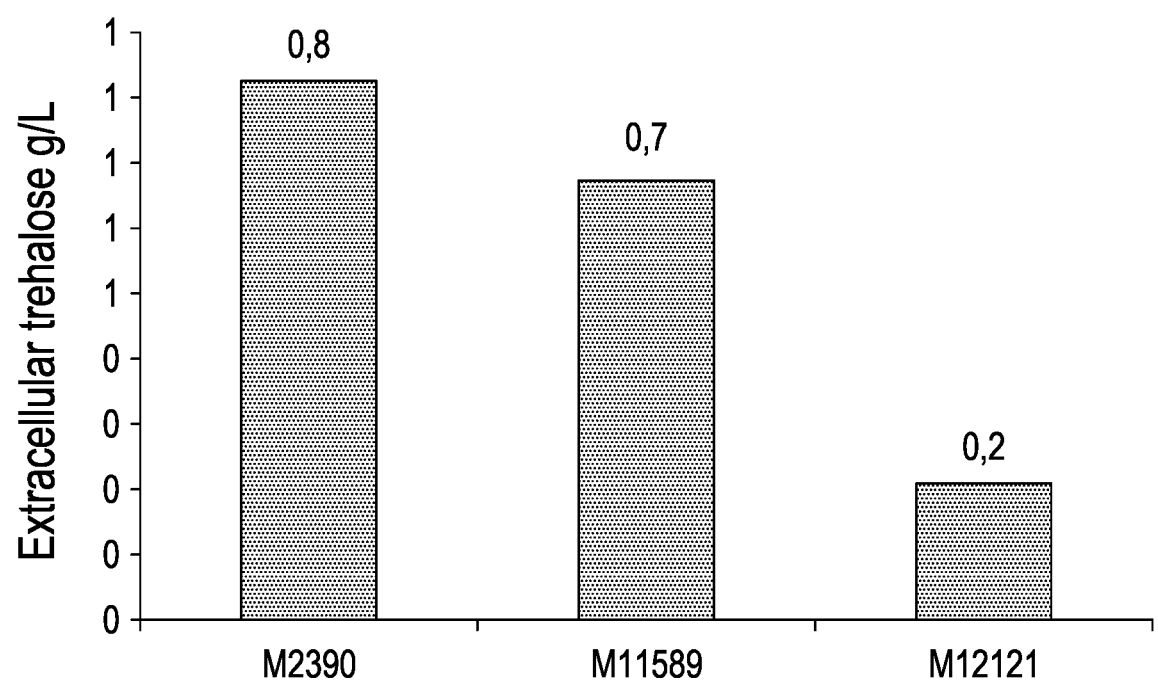

Example IV—Expression of Heterologous Trehalase and Glucoamylase Targeting Ethanol Production The material, methods and strains used in this example were presented in Example I. The heterologous trehalase gene, MP244 (SEQ ID NO: 1) was integrated into the genome of M11589, a strain expressing and secreting the heterologous glu011 glucoamylase from *S. fibuligera* and also possessing the glycerol reduction pathway The resulting strain, M12121 was subjected to a corn mash fermentation and compared to the parent M11589 along with a wild-type strain with no genetic modifications, M2390. As was observed with the exogenous addition of a trehalose, the expression of the MP244 trehalase provided an additional 1.1% yield increase (FIG. 7A) along with a measurable decrease in residual trehalose (FIG. 7B).

Example V—Maltodextrin Fermentation

Some of the material, methods and strains used in this example were presented in Example I.

Figure 9A:
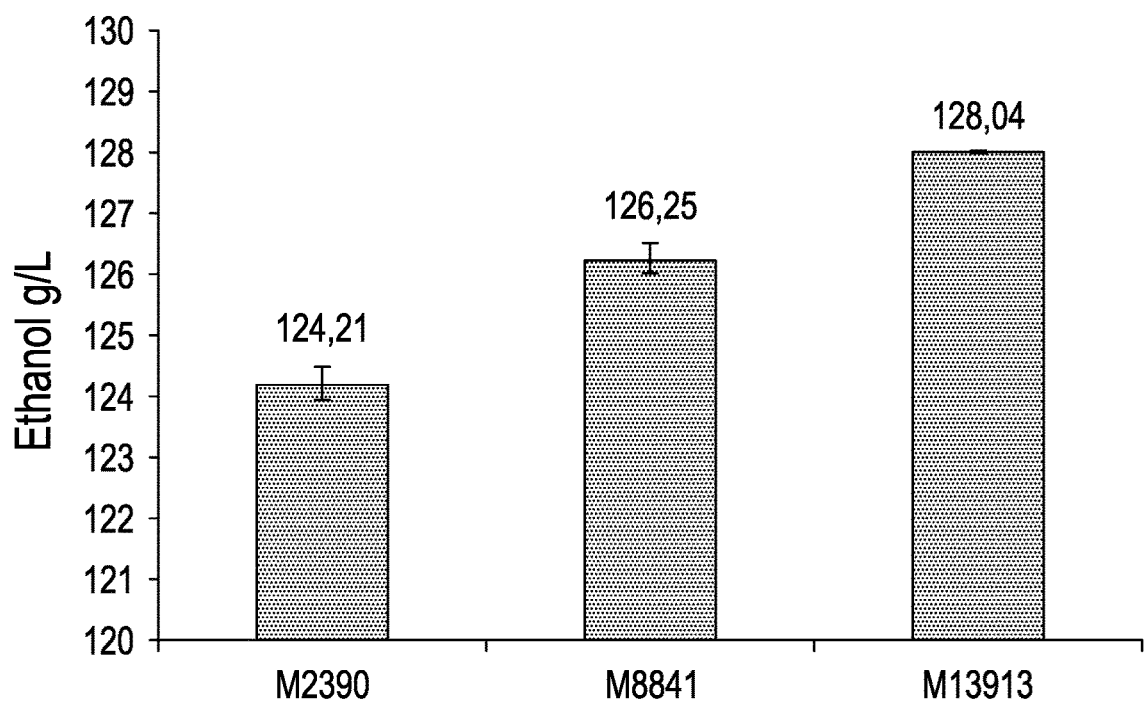
FIGS. 9A and 9B illustrate the effects of a maltodextrin fermentation by a *S. cerevisiae* strain M13913 expressing an heterologous glucoamylase, the glycerol reduction pathway as described in WO 2012/138942 and an heterologous trehalase on ethanol (A) and trehalose (B) concentrations. Results are shown as ethanol concentration (A, in g/L) or trehalose concentration (B, in g/L) in function of experimental conditions used.
Figure 9B:
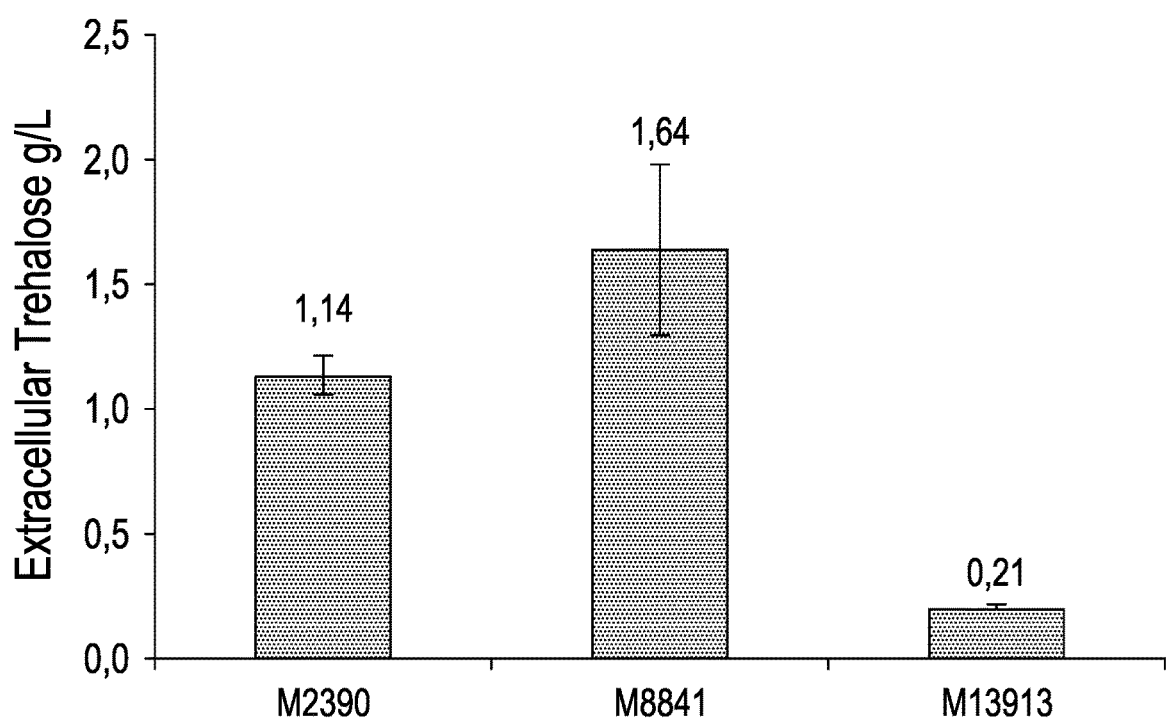

The heterologous trehalase gene, MP244 (SEQ ID NO: 1) was integrated into the genome of M8841, a strain expressing and secreting the heterologous glu011 glucoamylase from *S. fibuligera* and also possessing the glycerol reduction pathway as described in WO 2012/138942. The resulting strain, M13913 was subjected to a 260 g/L maltodextrin fermentation and compared to the parent M8841 along with a wild-type strain with no genetic modifications, M2390. As was observed with the exogenous addition of a trehalose, the expression of the MP244 trehalase provided an additional 1.42% yield increase over the parent strain, M8841, and a total 3.1% yield increase over the wild type strain (FIG. 9A) along with a measurable decrease in residual trehalose (FIG. 9B). While the invention has been described in connection with specific embodiments thereof, it will be understood that the scope of the claims should not be limited by the preferred embodiments set forth in the examples, but should be given the broadest interpretation consistent with the description as a whole.

REFERENCES

WO 2011/153516

WO 2012/138942

An M Z, Tang Y Q, Mitsumasu K, Liu Z S, Shigeru M, Kenji K. Enhanced thermotolerance for ethanol fermentation of *Saccharomyces cerevisiae* strain by overexpression of the gene coding for trehalose-6-phosphate synthase. Biotechnol Lett. 33.7 (2011): 1367-1374.

Bell W., Sun W., Hohmann S., Wera S., Reinders A., De Virgilio C., Wiemken A., Thevelein J M. Composition and Functional Analysis of the *Saccharomyces cerevisiae* Trehalose Synthase Complex. Journal of Bio Chem. 11 (1998): 33311-33319.

Cao T S, Chi Z., Liu G L., Chi Z M. Expression of TPS1 gene from *Saccharomycopsis fibuligera* All in *Saccharomyces* sp. WO enhances trehalose accumulation, ethanol tolerance, and ethanol production. Mol Biotechnol 56.1 (2014): 72-78.

Elbein A D, Pan Y T, Pastuszak I, Carroll D. New insights on trehalose: a multifunctional molecule. Glycobiology. 13.4 (2003): 17-27.

Ge X Y, Xu Y, Chen X. Improve carbon metabolic flux in *Saccharomyces cerevisiae* at high temperature by overexpressed TSL1 gene. J Ind Microbiol Biotechnol. 40 (2013): 345-352.

Giffen N. New Insights into fermentation drop samples: The real story of residual sugars. Fuel Ethanol Workshop and Expo. Minneapolis, Minn. Jun. 5, 2012.

Guo Z P, Zhang L, Ding Z Y, Shi G Y. Minimization of glycerol synthesis in industrial ethanol yeast without influencing its fermentation performance. Metabol Eng 13.1 (2011): 49-59.

Singer M A and Lindquist S. Thermotolerance in *Saccharomyces cerevisiae*: the Yin and Yang of trehalose. Trends Biotechnol. 16.11 (1998): 460-468.

Thevelain J M. and Hohmann S. Trehalose synthase: guard to the gate of glycolysis in yeast? Trends Biochem Sci 20.1 (1995): 3-10.

What is claimed is:

1. A recombinant yeast host cell comprising:
   (i) a first genetic modification for reducing the production of one or more native enzymes that function to produce glycerol, thereby reducing the production of glycerol, wherein the one or more native enzymes that function to produce glycerol is a glycerol-3-phosphate dehydrogenase 1 (GPD1) polypeptide, a polypeptide encoded by a gpd1 gene ortholog, a glycerol-3-phosphate dehydrogenase 2 (GPD2) polypeptide, a polypeptide encoded by a gpd2 gene ortholog, or a combination thereof;
   (ii) a second genetic modification for allowing the production of a heterologous glucoamylase; and
   (iii) a third genetic modification for allowing the expression of a heterologous trehalase.

2. The recombinant yeast host cell of claim 1, wherein the first genetic modification for reducing the production of one or more native enzymes that function to produce glycerol is for reducing the production of a FDP1 suppressor (FPS1) polypeptide or a polypeptide encoded by a fps1 gene ortholog, or a combination thereof.

3. The recombinant yeast host cell of claim 1, wherein the first genetic modification for reducing the production of glycerol one or more native enzymes that function to produce glycerol is for increasing the production of sugar transporter-like (STL1) polypeptide or a polypeptide encoded by a stl 1 gene ortholog, or a combination thereof.

4. The recombinant yeast host cell of claim 1, wherein the heterologous glucoamylase is from *Rhizopus* sp.

5. The recombinant yeast host cell of claim 1, wherein the heterologous trehalase is from *Candida* sp., *Kluyveromyces* sp. or *Magnaporthe* sp.

6. The recombinant yeast host cell of claim 4, wherein the heterologous trehalase is from *Candida* sp., *Kluyveromyces* sp. or *Magnaporthe* sp.

7. The recombinant yeast host cell of claim 1, wherein the heterologous trehalase has the amino acid sequence of SEQ ID NO: 8 or 13, is a variant of the amino acid sequence of SEQ ID NO: 8 or 13 having trehalase activity or is a fragment of the amino acid sequence of SEQ ID NO: 8 or 13 having trehalase activity.

8. The recombinant yeast host cell of claim 4, wherein the heterologous trehalase has the amino acid sequence of SEQ ID NO: 8 or 13, is a variant of the amino acid sequence of SEQ ID NO: 8 or 13 having trehalase activity or is a fragment of the amino acid sequence of SEQ ID NO: 8 or 13 having trehalase activity.

9. The recombinant yeast host cell of claim 1, wherein the recombinant yeast host cell is from the genus *Saccharomyces* sp.

10. The recombinant yeast host cell of claim 9, wherein the recombinant yeast host cell is from the species *Saccharomyces cerevisiae*.

11. The recombinant yeast host cell of claim 4, wherein the recombinant yeast host cell is from the genus *Saccharomyces* sp.

12. The recombinant yeast host cell of claim 11, wherein the recombinant yeast host cell is from the species *Saccharomyces cerevisiae*.

13. The recombinant yeast host cell of claim 7, wherein the recombinant yeast host cell is from the genus *Saccharomyces* sp.

14. The recombinant yeast host cell of claim 13, wherein the recombinant yeast host cell is from the species *Saccharomyces cerevisiae*.

15. A process for converting a substrate into a fermentation product, the process comprising contacting biomass comprising the substrate with the recombinant yeast host cell of claim 1 under conditions to allow conversion of at least a part of the substrate into the fermentation product.

16. The process of claim 15, wherein the substrate comprises corn, starch, maltodextrin or a combination thereof.

17. The process of claim 15, wherein the fermentation product is ethanol.

* * * * *